United States Patent
Cohen et al.

(10) Patent No.: US 11,350,977 B2
(45) Date of Patent: Jun. 7, 2022

(54) MODULAR ELECTROSURGICAL DEVICE

(71) Applicant: Memic Innovative Surgery Ltd., Kfar-Saba (IL)

(72) Inventors: Dvir Cohen, Ramot-Menashe (IL); Yaron Levinson, Tel-Aviv (IL)

(73) Assignee: Memic Innovative Surgery Ltd., Or-Yehuda (IL)

( * ) Notice: Subject to any disclaimer, the term of this patent is extended or adjusted under 35 U.S.C. 154(b) by 370 days.

(21) Appl. No.: 15/915,292

(22) Filed: Mar. 8, 2018

(65) Prior Publication Data
US 2018/0256235 A1 Sep. 13, 2018

Related U.S. Application Data

(60) Provisional application No. 62/583,543, filed on Nov. 9, 2017, provisional application No. 62/468,507, filed on Mar. 8, 2017.

(51) Int. Cl.
*A61B 18/12* (2006.01)
*A61B 18/00* (2006.01)
(Continued)

(52) U.S. Cl.
CPC ........... *A61B 18/00* (2013.01); *A61B 34/30* (2016.02); *A61B 34/35* (2016.02); *A61B 34/74* (2016.02);
(Continued)

(58) Field of Classification Search
CPC ............ A61B 17/00234; A61B 18/00; A61B 2017/00199; A61B 2017/00411; A61B 2018/00208; A61B 2018/00988; A61B 2018/1253; A61B 2018/126; A61B 34/74; A61B 2017/00477; A61B 34/25; A61B 34/30; A61B 34/35; A61B 18/12; A61B 18/1206; A61B 2018/00577; A61B 2018/00589; A61B 2018/00595; A61B 2018/00601; A61B 2018/00607; A61B 2034/742; A61B 90/98;
(Continued)

(56) References Cited

U.S. PATENT DOCUMENTS 5,472,442 A 12/1995 Klicek
5,697,949 A * 12/1997 Giurtino ............ A61B 18/1445
606/205

(Continued)

FOREIGN PATENT DOCUMENTS

CA 2957362 3/2017
EP 2842509 3/2015
(Continued)

OTHER PUBLICATIONS

Official Action dated Jun. 13, 2019 From the US Patent and Trademark Office Re. U.S. Appl. No. 15/915,237. (33 pages).
(Continued)

*Primary Examiner* — Daniel W Fowler

(57) ABSTRACT

A surgical system comprising: a plurality of modular units, each unit comprising: a motor unit; and a surgical mechanical arm actuated by, connected to and supplied with electrosurgical power by the motor unit; and a memory configured to store a selected electrosurgical operational mode for each of the plurality of modular units.

36 Claims, 24 Drawing Sheets

(51) Int. Cl.
*A61B 34/00* (2016.01)
*A61B 34/30* (2016.01)
*A61B 90/98* (2016.01)
*A61B 34/35* (2016.01)
*A61B 17/00* (2006.01)

(52) U.S. Cl.
CPC ........ *A61B 90/98* (2016.02); *A61B 17/00234* (2013.01); *A61B 18/1206* (2013.01); *A61B 34/25* (2016.02); *A61B 2017/00199* (2013.01); *A61B 2017/00411* (2013.01); *A61B 2017/00477* (2013.01); *A61B 2018/00208* (2013.01); *A61B 2018/00577* (2013.01); *A61B 2018/00589* (2013.01); *A61B 2018/00595* (2013.01); *A61B 2018/00601* (2013.01); *A61B 2018/00607* (2013.01); *A61B 2018/00988* (2013.01); *A61B 2018/126* (2013.01); *A61B 2018/1253* (2013.01); *A61B 2034/742* (2016.02)

(58) Field of Classification Search
CPC .......... A61B 2018/00636; A61B 2018/00642; A61B 2018/00648; A61B 2018/00654; A61B 2018/00666; A61B 2018/00672; A61B 2018/00678; A61B 2018/00696; A61B 2018/00702; A61B 2018/00708; A61B 2018/00773; A61B 2018/00779; A61B 2018/00785; A61B 2018/00898
See application file for complete search history.

(56) References Cited

U.S. PATENT DOCUMENTS

| | | | |
|---|---|---|---|
| 5,827,281 A | 10/1998 | Levin | |
| 5,830,231 A | 11/1998 | Geiges, Jr. | |
| 5,931,857 A | 8/1999 | Prieve et al. | |
| 7,442,194 B2 | 10/2008 | Dumbauld et al. | |
| 8,251,989 B1* | 8/2012 | Newton | A61B 18/1233 606/34 |
| 2002/0165541 A1* | 11/2002 | Whitman | A61N 7/02 606/48 |
| 2004/0082946 A1* | 4/2004 | Malis | A61B 18/1206 606/34 |
| 2004/0097913 A1 | 5/2004 | Refior et al. | |
| 2005/0059960 A1 | 3/2005 | Simaan et al. | |
| 2005/0113827 A1* | 5/2005 | Dumbauld | A61B 18/1445 606/45 |
| 2005/0165443 A1 | 7/2005 | Livneh | |
| 2006/0064086 A1 | 3/2006 | Odom | |
| 2007/0005045 A1* | 1/2007 | Mintz | A61B 34/74 606/1 |
| 2008/0015566 A1 | 1/2008 | Livneh | |
| 2008/0132893 A1 | 6/2008 | D'Amelio et al. | |
| 2008/0249523 A1* | 10/2008 | McPherson | A61B 18/1445 606/41 |
| 2010/0011900 A1* | 1/2010 | Burbank | A61B 34/71 74/490.06 |
| 2010/0016852 A1 | 1/2010 | Manzo et al. | |
| 2010/0305564 A1* | 12/2010 | Livneh | A61B 18/1442 606/41 |
| 2011/0196419 A1 | 8/2011 | Cooper | |
| 2011/0218502 A1 | 9/2011 | Iio et al. | |
| 2011/0238065 A1 | 9/2011 | Hunt et al. | |
| 2011/0282339 A1 | 11/2011 | Weizman et al. | |
| 2012/0215220 A1 | 8/2012 | Manzo et al. | |
| 2013/0123783 A1 | 5/2013 | Marczyk et al. | |
| 2013/0178845 A1 | 7/2013 | Smith et al. | |
| 2013/0237986 A1 | 9/2013 | Mueller | |
| 2014/0005653 A1 | 1/2014 | Shelton, IV et al. | |
| 2014/0046340 A1* | 2/2014 | Wilson | A61B 90/30 606/130 |
| 2014/0128886 A1* | 5/2014 | Holop | A61B 34/30 606/130 |
| 2015/0066022 A1 | 3/2015 | Shelton, IV et al. | |
| 2015/0148803 A1 | 5/2015 | Kaneko et al. | |
| 2016/0022356 A1 | 1/2016 | Schostek et al. | |
| 2016/0074120 A1* | 3/2016 | Farritor | A61B 17/2812 606/130 |
| 2016/0151115 A1* | 6/2016 | Karguth | A61B 1/00149 600/102 |
| 2016/0262826 A1 | 9/2016 | Allen, IV | |
| 2017/0035526 A1 | 2/2017 | Farritor et al. | |
| 2017/0119452 A1* | 5/2017 | Ellman | A61B 18/1206 |
| 2017/0172594 A1 | 6/2017 | Allen, IV | |
| 2017/0258539 A1 | 9/2017 | Cohen et al. | |
| 2018/0000549 A1 | 1/2018 | Kopp | |
| 2018/0256241 A1 | 9/2018 | Cohen et al. | |
| 2018/0256246 A1 | 9/2018 | Cohen et al. | |

FOREIGN PATENT DOCUMENTS

| | | |
|---|---|---|
| WO | WO 2011/007351 | 1/2011 |
| WO | WO 2018/163182 | 9/2018 |

OTHER PUBLICATIONS

Official Action dated May 20, 2020 from the US Patent and Trademark Office Re. U.S. Appl. No. 15/915,237. (38 pages).
Official Action dated Jan. 11, 2019 From the US Patent and Trademark Office Re. U.S. Appl. No. 15/915,237. (32 pages).
International Preliminary Report on Patentability dated Sep. 19, 2019 From the International Bureau of WIPO Re. Application No. PCT/IL2018/050273. (11 Pages).
Restriction Official Action dated May 27, 2020 from the US Patent and Trademark Office Re. U.S. Appl. No. 15/915,235. (7 pages).
Applicant-Initiated Interview Summary dated Jul. 24, 2018 From the US Patent and Trademark Office Re. U.S. Appl. No. 15/915,237. (4 pages).
International Search Report and the Written Opinion dated Jul. 5, 2018 From the International Searching Authority Re. Application No. PCT/IL2018/050273. (26 Pages).
Official Action dated Jun. 14, 2018 From the US Patent and Trademark Office Re. U.S. Appl. No. 15/915,237. (22 pages).
Official Action dated Nov. 21, 2019 From the US Patent and Trademark Office Re. U.S. Appl. No. 15/915,237. (38 pages).
Official Action dated Oct. 22, 2020 from the US Patent and Trademark Office Re. U.S. Appl. No. 15/915,235. (31 Pages).
Communication Pursuant to Article 94(3) EPC Dated Nov. 13, 2020 From the European Patent Office Re. Application No. 18764956.1. (4 Pages).
Final Official Action dated Nov. 10, 2020 from the US Patent and Trademark Office Re. U.S. Appl. No. 15/915,237. (38 pages).
Final Official Action dated Apr. 27, 2021 from the US Patent and Trademark Office Re. U.S. Appl. No. 15/915,235. (28 pages).
Interview Summary dated Jan. 13, 2021 from the US Patent and Trademark Office Re. U.S. Appl. No. 15/915,235. (3 pages).
Interview Summary dated Feb. 17, 2021 From the US Patent and Trademark Office Re. U.S. Appl. No. 15/915,237. (3 Pages).
Supplementary Partial European Search Report and the European Search Opinion dated Mar. 5, 2021 From the European Patent Office Re. Application No. 18764956.1. (9 Pages).
Official Action dated May 25, 2021 from the US Patent and Trademark Office Re. U.S. Appl. No. 15/915,237. (47 pages).
Official Action dated Nov. 29, 2021 from the US Patent and Trademark Office Re. U.S. Appl. No. 15/915,235. (27 pages).
Final Official Action dated Feb. 22, 2022 from US Patent and Trademark Office Re. U.S. Appl. No. 15/915,237. (61 pages).

* cited by examiner

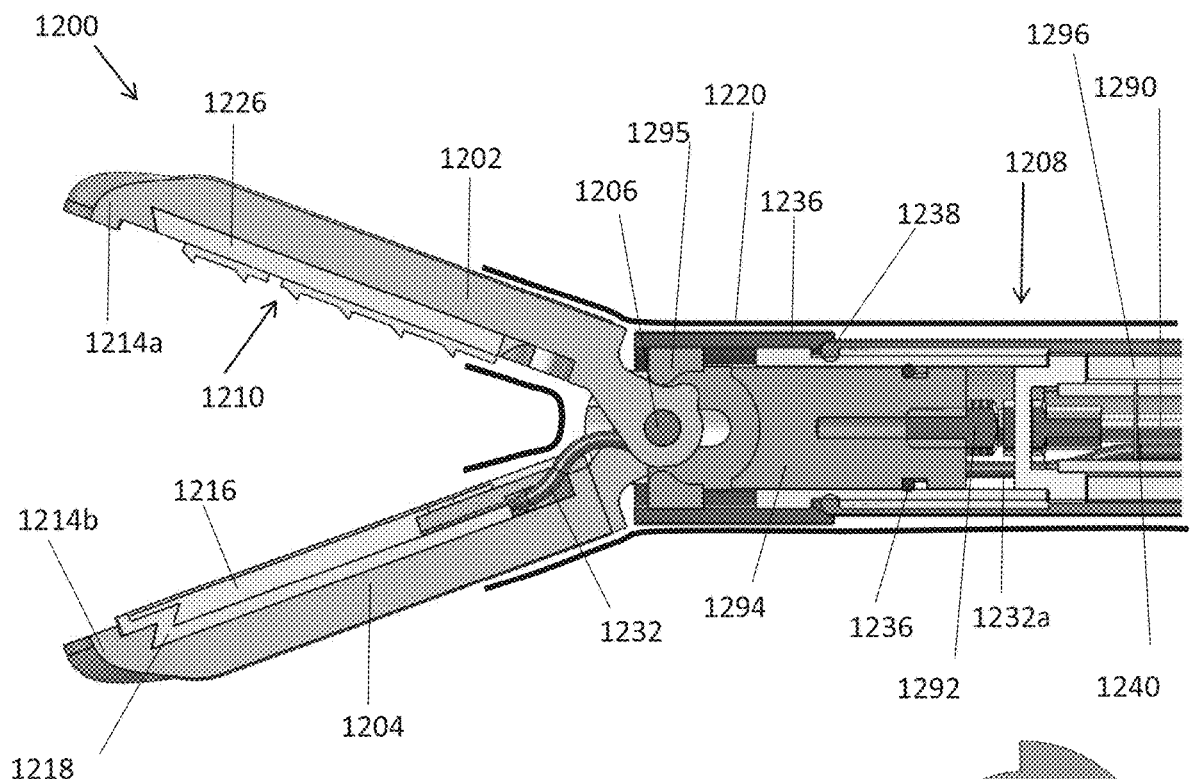
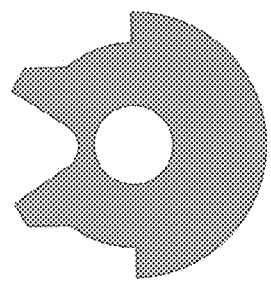
FIG. 12A
FIG. 12C
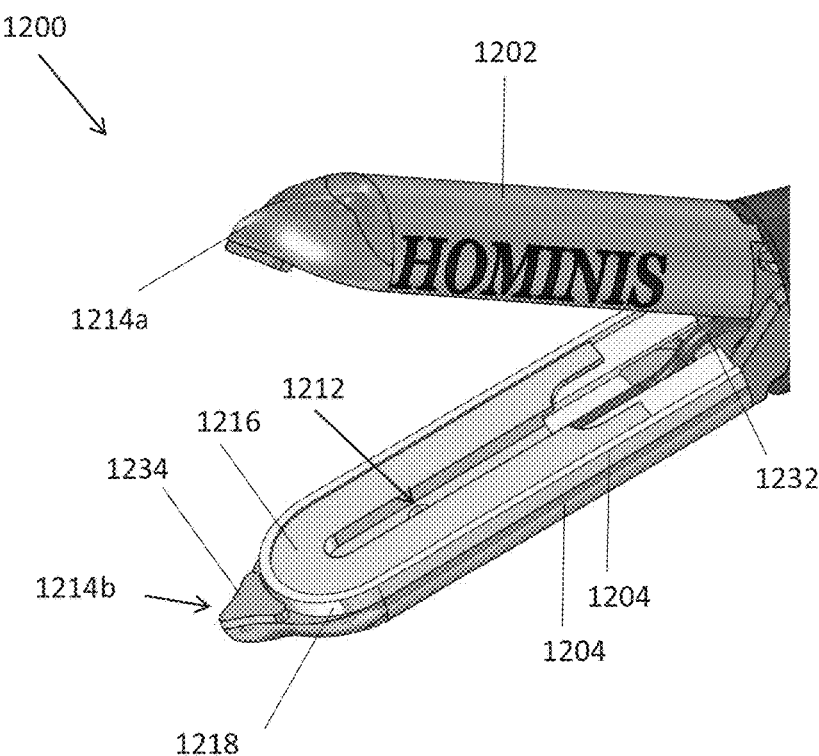
FIG. 12B

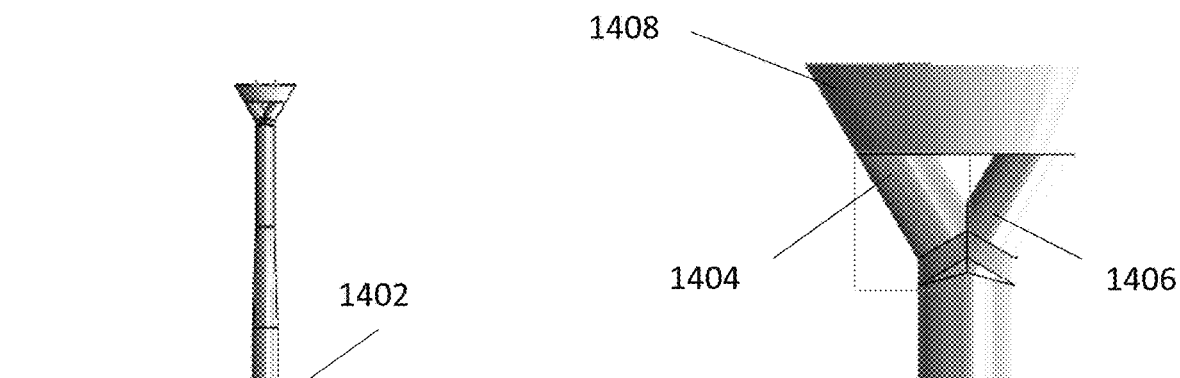
FIG. 14B
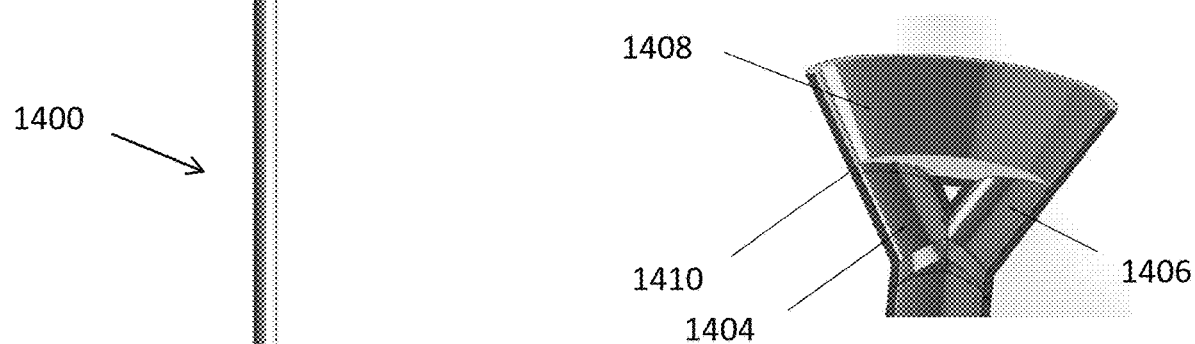
FIG. 14C
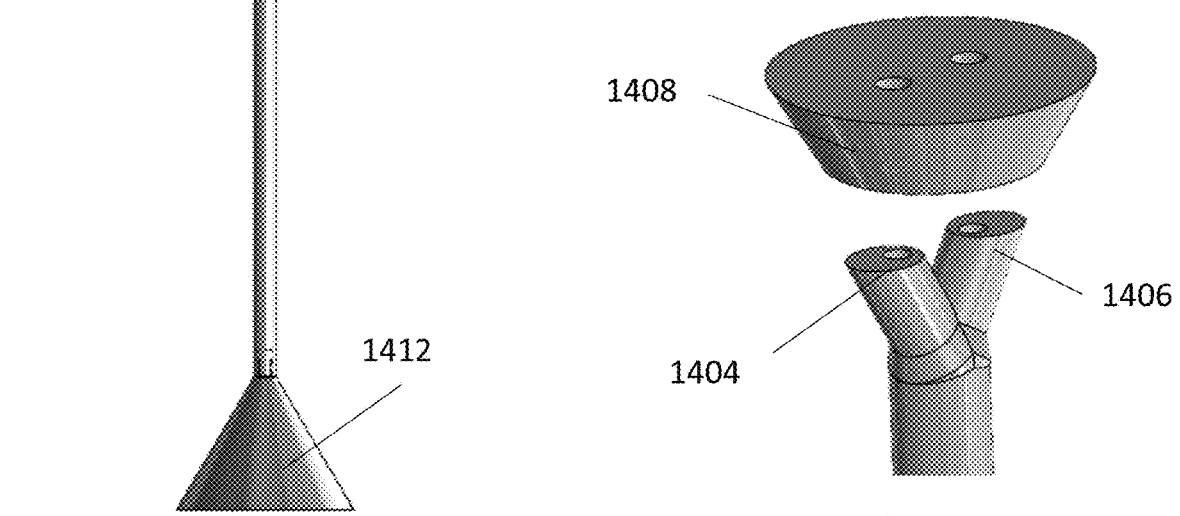
FIG. 14D
FIG. 14A

MODULAR ELECTROSURGICAL DEVICE

RELATED APPLICATIONS

This application claims the benefit of priority under 35 USC § 119(e) of U.S. Provisional Patent Application Nos. 62/583,543 filed on Nov. 9, 2017, and 62/468,507 filed on Mar. 8, 2017.

This application is also related to:

PCT Patent Application No. PCT/IL2015/050893 filed on Sep. 4, 2015,

PCT Patent Application No. PCT/IL2015/050892 filed on Sep. 4, 2015,

PCT Patent Application No. PCT/IL2015/050891 filed on Sep. 4, 2015,

PCT Patent Application No. PCT/IL2016/050976 filed on Sep. 4, 2016 and

U.S. patent application Ser. No. 15/454,123 filed on Mar. 9, 2017.

The contents of the above applications are all incorporated by reference as if fully set forth herein in their entirety.

FIELD AND BACKGROUND OF THE INVENTION

The present invention, in some embodiments thereof, relates to an electro-surgical system and, more particularly, but not exclusively, to a combined monopolar and bipolar electro-surgical system.

Background art includes: U.S. Patent Application Publication No. US2013178845 which discloses "An integrated catheter assembly comprises a bipolar electrode tool and a monopolar electrode tool. The catheter assembly enables an operator to perform both bipolar and monopolar procedures on tissue without having to withdraw the catheter assembly, without having to remove or replace any part of the catheter assembly, and/or without having to insert any additional tools or parts. The catheter assembly may comprise a switching mechanism such that when one of the bipolar electrode tool and monopolar electrode tool is electrically activated, the other of the bipolar electrode tool and monopolar electrode tool cannot be electrically activated. In one embodiment of a method, the operator uses a single catheter assembly for applying bipolar current for tissue electro-therapy and monopolar current for tissue cutting."

U.S. Pat. No. 5,472,442 discloses "An active electrode switches from a monopolar mode extending from a handpiece and a patient return to a bipolar mode with the active and return electrodes extending. An active lead selectively connects the active output and the active electrode. A return lead selectively connects the return electrode and the return output in the monopolar mode or the return terminal when in the bipolar mode. Terminals connect with wiring to the electrodes to complete the circuit for the bipolar mode. One terminal is on the generator and one is in the handpiece to connect to the electrodes and complete the circuit for bipolar. The electrode has a control on the handpiece for the surgeon to change circuitry and to position the electrode for each mode. The return electrode in the monopolar mode is in the handpiece disconnected from its terminal. The return electrode connects to its terminal when extended from the handpiece but for monopolar a pair of patient pads connected to a monitoring circuit test continuity. A method of use has steps of switching the electrode from the monopolar to bipolar, providing the generator with outputs to the electrodes, having terminals for the electrodes when used for bipolar, including an active lead selectively in circuit between the active output and electrode and including a return lead selectively in circuit between the return electrode and output when monopolar or the terminal when bipolar."

European Patent No. EP2842509 discloses "A surgical instrument includes an end effector assembly and a switch assembly. The end effector assembly includes a monopolar assembly and a bipolar assembly. The switch assembly includes first and second bipolar inputs, first and second bipolar outputs, a monopolar input, and a monopolar output. The switch assembly is transitionable between a first condition, wherein the first and second bipolar inputs are coupled to the first and second bipolar outputs, respectively, for supplying energy to the bipolar assembly, and a second condition, wherein the mono polar input and the monopolar output are coupled to one another for supplying energy to the monopolar assembly."

SUMMARY OF THE INVENTION

Following are examples of some embodiments of the invention. Features of one example may be combined with features of one or more other examples, unless expressly prohibited and form additional examples of some embodiments of the invention.

EXAMPLE 1

A surgical mechanical arm comprising:
an electrosurgical tool comprising:
a first tool portion comprising a first surface;
a second tool portion comprising a second surface, where said tool portions are mechanically coupled and configured to move relative to each other to change a separation between said first and second surfaces;
a first elongated element electrically coupled to at least a part of said first tool portion which is electrically isolated from said second tool portion; and
a second elongated element electrically coupled to at least a part of said first tool portion and mechanically coupled to and configured to actuate one or both of said tool portions to change said separation between said first and second surfaces.

EXAMPLE 2

The surgical mechanical arm of Example 1, wherein said tool portions move relative to each other to contact said first and second surfaces and separate said surfaces from contact.

EXAMPLE 3

The surgical mechanical arm of Example 1, wherein said first tool portion is configured to be moved such that said first surface contacts said second surface.

EXAMPLE 4

The surgical mechanical arm of Example 1, wherein said second elongated element actuates said first tool portion by moving said first tool portion towards said second tool portion.

EXAMPLE 5

The surgical mechanical arm of Example 1, wherein said second elongated element actuates said tool portions by moving said first tool portion and said second tool portion towards each other.

EXAMPLE 6

The surgical mechanical arm of Example 1, wherein rotation of said second elongated element about a second elongated element long axis moves said first tool portion such that said first surface moves towards said second surface.

EXAMPLE 7

The surgical mechanical arm of Example 6, wherein said rotation of said second elongated element moves said second tool portion such that said second surface moves towards said first portion.

EXAMPLE 8

The surgical mechanical arm of Example 6, wherein said rotation of said second elongated element moves said first tool portion when one or more portion of said second elongated element is bent.

EXAMPLE 9

The surgical mechanical arm of Example 1, comprising a screw coupled to said second elongated element and said tool portions; wherein rotation of said second elongated element rotates said screw to move said tool portions relative to each other.

EXAMPLE 10

The surgical mechanical arm of Example 9, wherein said first tool portion and said second tool portion are coupled a by a pivot joint and move towards each other by rotation about said pivot joint.

EXAMPLE 11

The surgical mechanical arm of Example 1, wherein said second elongated element is a torque cable.

EXAMPLE 12

The surgical mechanical arm of Example 1, comprising an elongated segment comprising a proximal and a distal end and describing a hollow passageway; wherein said first and said second tool portions are coupled to said distal end of said segment.

EXAMPLE 13

The surgical mechanical arm of Example 12, wherein said segment is electrically connected to said second elongated element.

EXAMPLE 14

The surgical mechanical arm of Example 12, wherein rotation of said segment about a segment long axis rotates said first and said second tool portions about said segment long axis.

EXAMPLE 15

The surgical mechanical arm of Example 12, wherein said first and said second elongated elements extend through said hollow passageway; wherein said second elongated element is coupled to said first and second tool portions at said distal end of said segment.

EXAMPLE 16

The surgical mechanical arm of Example 15, wherein rotation of said segment about a segment long axis rotates said first and said second elongated elements about said segment long axis.

EXAMPLE 17

The surgical mechanical arm of Example 1, wherein said first elongated element comprises a wire covered in an insulator.

EXAMPLE 18

The surgical mechanical arm of Example 17, wherein said first elongated element comprises a litz wire.

EXAMPLE 19

The surgical mechanical arm of Example 1, wherein said first tool portion includes a monopolar tip.

EXAMPLE 20

The electrosurgical tool of Example 19, wherein said monopolar tip has a spatula shape.

EXAMPLE 21

The electrosurgical tool of Example 19, wherein said monopolar tip extends from said first portion by 1-5 mm.

EXAMPLE 22

The electrosurgical tool of Example 19, wherein said monopolar tip is 0.1-2 mm thick.

EXAMPLE 23

The surgical mechanical arm of Example 1, wherein said first elongated element is coupled to a first electrical supply contact and said second elongated element is coupled to second electrical supply contact.

EXAMPLE 24

The surgical mechanical arm of Example 1, comprising an electrically insulating sheath covering at least a portion of said arm.

EXAMPLE 25

The surgical mechanical arm of Example 24, wherein said sheath covers a distal portion of said arm excluding said first and second portions.

EXAMPLE 26

The surgical mechanical arm of Example 1, wherein changing tension applied to said second elongated element mechanically actuates one or both of said portions.

EXAMPLE 27

The electrosurgical tool according to Example 26, wherein said second elongated element is configured to transfer tension applied to a proximal end of said second elongated element to a distal end of said second elongated element, which distal end actuates said first and section portions.

EXAMPLE 28

The electrosurgical tool according to Example 1, wherein said second elongated element is configured to transfer torque applied to a proximal end of said second elongated element to a distal end of said second elongated element, which distal end actuates said first and section portions.

EXAMPLE 29

A surgical system comprising:
an electrosurgical power generator;
at least one surgical mechanical arm comprising a tool configured to operate in at least one bipolar operational mode;
at least one motor unit comprising:
a connector configured to connect said motor unit to said electrosurgical power generator or wherein said electrosurgical power generator is housed within said at least one motor unit; wherein said at least one motor unit comprises:
one or more actuators mechanically coupled to said surgical arm and configured to actuate said surgical arm;
a first electrical conduction pathway electrically connected to said electrosurgical power generator and extending from said motor unit, through a volume defined by said surgical mechanical arm, to said tool; and
a second electrical conduction pathway connected to said electrosurgical power generator and extending from said motor unit to said tool.

EXAMPLE 30

The surgical system of Example 29, wherein said tool is configured to operate in at least one monopolar electrosurgical mode.

EXAMPLE 31

The surgical system of any one of Examples 29-30, wherein said tool is configured to operate in an uncharged mode.

EXAMPLE 32

The surgical system of Example 29, wherein said one or more actuators rotate portions of said surgical arm thereby rotating said first electrical conduction pathway and said second electrical conduction pathway.

EXAMPLE 33

The surgical system of Example 32, wherein said one or more actuators rotate one or more surgical arm gear, which surgical arm gears are configured to actuate portions of the surgical arm.

EXAMPLE 34

The surgical system of Example 33, wherein one or more surgical arm gear isolates said first electrical conduction pathway from said second electrical conduction pathway.

EXAMPLE 35

The surgical system of Example 29,
wherein said first electrical conduction pathway includes a first slip ring disposed within said motor unit; and
wherein said second electrical conduction pathway includes a second slip ring disposed within said motor unit;
wherein said first slip ring and said second slip ring are coupled by a gear, which gear is configured to electrically isolate and to rotate the slip rings.

EXAMPLE 36

The surgical system of Example 35, wherein said first slip ring, said second slip ring and said gear have coaxial axes of rotation.

EXAMPLE 37

The surgical system of Example 33, wherein one or more surgical arm gear isolates said first electrical conduction pathway from said second electrical conduction pathway.

EXAMPLE 38

The surgical system according to any one of Examples 33-37, comprising an elongated portion coupled to said tool;
wherein said gear is coupled to said elongated portion and configured to rotate said elongated portion about an elongated portion long axis thereby rotating said tool.

EXAMPLE 39

The surgical system according to Example 38, wherein said first electrical conduction pathway includes said elongated portion.

EXAMPLE 40

The surgical system according to any one of Examples 38-39, wherein said first electrical conduction pathway includes an elongated element configured to actuate.

EXAMPLE 41

The surgical system according to any one of Examples 38-40, wherein said first electrical conduction pathway includes a tubular portion of an electrosurgical arm.

EXAMPLE 42

The surgical system according to any one of Examples 29-41, wherein said tool is a scissors.

EXAMPLE 43

An electrosurgical tool comprising:
a first portion including a monopolar tip and a first bipolar surface where said monopolar tip and said first bipolar surface are electrically connected;

a second portion mechanically coupled to said first portion;
a second bipolar surface:
attached to said second portion;
electrically isolated from said first bipolar surface and said second portion; and
configured to be brought towards said first bipolar surface;
a first electrical conduction pathway electrically connected to said first and second portions;
a second electrical pathway electrically connected to said second bipolar surface and electrically isolated from said first electrical conduction pathway.

EXAMPLE 44

The electrosurgical tool of Example 43, wherein said tool is sized and shaped for insertion into a body.

EXAMPLE 45

The electrosurgical tool of Example 43, wherein said first electrical conduction pathway includes an elongated element configured to actuate said first and second portions to move said portions in contact with each other.

EXAMPLE 46

The electrosurgical tool of Example 45, wherein said elongated element actuates said first and second portions by rotation about an elongated element long axis.

EXAMPLE 47

The electrosurgical tool of Example 46, wherein said elongated element is coupled to a screw, which is coupled to a connection between said first and said second portions;
wherein rotation of said elongated element linearly moves said screw with respect to said coupling.

EXAMPLE 48

The electrosurgical tool of Example 47, wherein said connection is a pivot connection.

EXAMPLE 49

The electrosurgical tool according to any one of Examples 43-48, wherein said tool is an elongate surgical mechanical arm.

EXAMPLE 50

The electrosurgical tool according to Example 49, wherein said first portion and said second portion are coupled to a distal end of a body of said elongate surgical mechanical arm.

EXAMPLE 51

The electrosurgical tool according to any one of Examples 49-50, wherein an actuator configured to rotate said elongate element is coupled to a proximal portion of said surgical mechanical arm.

EXAMPLE 52

The electrosurgical tool according to any one of Examples 49-51, wherein said first electrical conduction pathway includes a tubular portion of an electrosurgical arm.

EXAMPLE 53

The electrosurgical tool according to any one of Examples 49-52, wherein said monopolar tip has a spatula shape.

EXAMPLE 54

The electrosurgical tool according to any one of Examples 49-53, wherein said monopolar tip extends from said first portion by 1-5 mm.

EXAMPLE 55

The electrosurgical tool according to any one of Examples 49-54, wherein said monopolar tip is 0.1-2 mm thick.

EXAMPLE 56

The electrosurgical tool according to any one of Examples 49-55, wherein at least one of said portions includes a plurality of protrusions sized and shaped to increase friction between said first bipolar surface and said second bipolar surface.

EXAMPLE 57

The electrosurgical tool according to any one of Examples 49-56, comprising an electrically insulating sheath covering at least a portion of said surgical arm.

EXAMPLE 58

The electrosurgical tool according to Example 46, wherein said elongated element is configured to transfer torque applied to a proximal end of said elongated element to a distal end of said elongated element, which distal end actuates said first and section portions.

EXAMPLE 59

The electrosurgical tool according to Example 58, wherein said elongated element is configure to transfer torque when one or more portion of said elongated element is bent.

EXAMPLE 60

The electrosurgical tool according to Example 59, wherein said elongated element is a torque cable.

EXAMPLE 61

A surgical system comprising:
a plurality of modular units, each unit comprising:
a motor unit; and
a surgical mechanical arm actuated by, connected to and supplied with electrosurgical power by said motor unit; and
a memory configured to store a selected electrosurgical operational mode for each of said plurality of modular units.

EXAMPLE 62

The surgical system according to Example 61, wherein possible operational modes include at least one monopolar operational mode and at least one bipolar operational mode

EXAMPLE 63

The surgical system according to Example 61, wherein possible operational modes include at least one monopolar operational mode, at least one bipolar operational mode and an uncharged mode.

EXAMPLE 64

The surgical system according to any one of Examples 61-63, wherein said motor unit comprises circuitry configured to:
recognize said selected electrosurgical operational mode of power supply connected to said motor unit;
send, to a processor, an indication of said selected operational mode, where said processor is configured to store said indication in said memory.

EXAMPLE 65

The surgical system according to any one of Examples 61-64, comprising a user interface configured to:
receive said selected electrosurgical operational mode from a user, for one or more of said modular units;
send an indication of said selected electrosurgical operational mode to a processor, where said processor is configured to store said indication in said memory.

EXAMPLE 66

The surgical system according to any one of Examples 61-65, comprising one or more display configured to display an indication of said selected electrosurgical operational mode for one or more of said modular units.

EXAMPLE 67

The surgical system according to Example 65, wherein said user interface is a touch screen display.

EXAMPLE 68

The surgical system according to Example 67, wherein said touch screen display is configured to display an indication of said selected electrosurgical operational mode for one or more of said modular units.

EXAMPLE 69

The surgical system of Example 66, wherein said one or more display comprises one or more light on each of said motor units.

EXAMPLE 70

The surgical system of Example 61, comprising a processor connected to said memory, wherein one or more of said motor units comprises a relay comprising circuitry is configured to:
receive electrosurgical power supply to said motor unit;
receive a user selection of said electrosurgical mode from said processor;
check that said user selection matches an electrosurgical supply connected to said motor unit; and
enable said electrosurgical supply to said surgical arm if said user selection matches said supply.

EXAMPLE 71

The surgical system according to Example 70, wherein said relay comprises circuitry configured to disable said electrosurgical supply to said surgical arm if said user selection does not match said supply.

EXAMPLE 72

The surgical system according to any one of Examples 70-71, comprising circuitry configured to generate a warning if said user selection does not match said supply.

EXAMPLE 73

The surgical system according to Example 62, wherein said surgical mechanical arm includes a tool configured to operate in said possible operational modes.

EXAMPLE 74

The surgical system according to Example 73, wherein said tool comprises:
a monopolar tip;
a first portion comprising a first bipolar surface;
a second portion comprising a second bipolar surface configured to be in brought into contact with said first bipolar surface.

EXAMPLE 75

The surgical system according to Example 74, wherein said monopolar tip is attached to said first portion, where said monopolar tip and said first bipolar surface are electrically connected;
wherein said second bipolar surface is electrically isolated from said first bipolar surface and said second portion.

EXAMPLE 76

A method of use of an electrosurgical system:
providing a plurality of modular units;
selecting a desired electrosurgical operational mode for at least one of said modular units by one or more of:
connecting an electrosurgical supply to said at least one modular unit;
inputting a desired electrosurgical operational mode for said at least one modular unit at a user interface.

EXAMPLE 77

The method according to Example 76, wherein said connecting comprises connecting said electrosurgical supply to at least one modular unit.

EXAMPLE 78

The method according to any one of Examples 76-77, comprising: detecting an electrosurgical supply type of said electrosurgical supply connected to said at least one modular unit;

comparing, using a processor, said electrosurgical supply type with said desired electrosurgical operational mode; and enabling electrosurgical power supply to said surgical arm of said at least one modular unit if said electrosurgical supply type matches said desired electrosurgical operational mode.

EXAMPLE 79

The method according to Example 78, wherein said selecting is performed for at least two modular units;

wherein said detecting, said comparing and said enabling is performed for each said modular unit.

EXAMPLE 80

The method according to Example 79, wherein said enabling including enabling electrosurgical power supply to said surgical arms of said at least two modular units if said electrosurgical supply type matches said desired electrosurgical operational mode for each of said at least two modular units.

EXAMPLE 81

The method according to Example 78, comprising displaying an alert if said electrosurgical supply type does not match said desired electrosurgical operational mode.

EXAMPLE 82

The method according to Example 78 or to Example 81, comprising disabling said electrosurgical power supply to said surgical arm if said electrosurgical supply type does not match said desired electrosurgical operational mode.

EXAMPLE 83

The method according to Example 76, comprising attaching coupling at least two of said modular units by connecting motor units of said at least two of said modular units.

EXAMPLE 84

The method according to Example 76, comprising displaying a desired electrosurgical operational mode at a user interface.

EXAMPLE 85

The method according to Example 76, comprising displaying a connected electrosurgical supply type at said user interface.

EXAMPLE 86

The method according to Example 76, comprising displaying a connected electrosurgical supply type at a modular unit user interface.

EXAMPLE 87

The method according to Example 76, or Example 85 comprising displaying a desired electrosurgical operational mode at said user interface.

EXAMPLE 88

The method according to Example 80, comprising:
comparing one or more of:
said desired electrosurgical operational modes for said at least two modular units;
said electrosurgical supply type for said at least two modular units;
enabling said electrosurgical type for said at least two modular units if one or more of:
said desired electrosurgical operational modes for said at least two modular units match; and
said electrosurgical supply type for said at least two modular units match.

EXAMPLE 89

An insulating sheath comprising:
an elongated body, 15-10,000 mm long, with a maximal cross sectional dimension of 2-20 mm, which is elastic at least in directions perpendicular to a long axis of said body;
a bifurcated end including a first and a second part, wherein a ratio of a length of said bifurcated end to a length of said elongated body is 1:2-1:1000.

EXAMPLE 90

The insulating sheath of Example 89, a length of said bifurcated end is 1-100 mm.

EXAMPLE 91

The insulating sheath of Example 89, a length of said bifurcated end is 1-20 mm.

EXAMPLE 92

The insulating sheath of Example 89, wherein said elongated body is 400-500 mm long.

EXAMPLE 93

The insulating sheath of Example 89, wherein said maximal cross sectional dimension is 5-12 mm.

EXAMPLE 94

The insulating sheath of Example 89, wherein said body and said bifurcated end include silicone rubber.

EXAMPLE 95

The insulating sheath of Example 89, wherein said sheath is mounted on a surgical arm, said arm including at least two moving portions.

EXAMPLE 96

The insulating sheath of Example 95, wherein said surgical arm comprises a first moving portion disposed within said first part and a second moving portion disposed within said second part.

EXAMPLE 97

The insulating sheath of Example 89, wherein said sheath is flexible.

EXAMPLE 98

The insulating sheath of Example 89, wherein said body tapers along a length of the sheath towards said first and second parts.

EXAMPLE 99

The insulating sheath of Example 89, wherein said sheath is 0.1-1 mm thick.

EXAMPLE 100

The insulating sheath of Example 89, wherein said sheath is electrically insulating.

EXAMPLE 101

A method of manufacturing an insulating sheath comprising:
providing a jig comprising an elongated body and a bifurcated end;
coating said jig;
removing the coating from said jig in one piece.

EXAMPLE 102

A surgical tool comprising:
a first surface coupled to a pivot;
a second surface in contact with said first surface at a contact point;
an actuator configured to move said first and second surfaces linearly with respect to each other to roll or slide said second surface to change said contact point between said surfaces to generate a moment said pivot;
wherein said surfaces are shaped such that a rate of change of distance between said pivot and said contact point with respect to movement along an axis of the linear movement is higher for a first portion of the surfaces than for a second portion of the surfaces said moment being larger for said first portion than for said second portion.

EXAMPLE 103

The surgical tool of Example 102, wherein said first surface is concave and wherein said second surface is convex.

EXAMPLE 104

The surgical tool according to any one of Examples 102-103, wherein said first surface is an outer surface of an portion of an opposing portion of a tool; wherein Example said moment pivots said opposing portion towards a second tool portion.

EXAMPLE 105

The surgical tool of Example 104, wherein said opposing portion is one of:
a gripper opposing portion where said another tool portion is a second gripper opposing portion;
a scissors blade where said another tool portion is a second scissors blade.

EXAMPLE 106

The surgical tool according to any one of Examples 102-105, wherein said pivot is coupled to a distal end of a surgical arm.

EXAMPLE 107

The surgical tool according to any one of Examples 104, wherein said tool comprises:
a third surface according to said first surface;
and a fourth surface coupled to and according to said second surface;
wherein said third surface is an outer surface of an portion of said second tool portion;
wherein said moment pivots said second tool portion towards said opposing portion.

EXAMPLE 108

A method of actuating a surgical tool comprising:
linearly moving a first tool portion with respect to a second tool portion where a first surface of said first tool portion moves in contact along a second surface of said second tool portion;
wherein said second tool portion is fixed at and pivotable about a pivot;
wherein said movement generates a moment on said second tool portion about said pivot;
wherein a gradient of said first surface with respect to said second surface has a portion of higher gradient and a portion of lower gradient, said portion of higher gradient corresponding to a moment in a first direction about said pivot and said portion of higher gradient corresponding to a moment in a second direction about said pivot.

EXAMPLE 109

The surgical mechanical arm of Example 1, wherein said second elongated element is electrically coupled to said surgical mechanical arm.

EXAMPLE 110

The surgical mechanical arm of Example 109, comprising an electrically insulating sheath covering at least a portion of said arm.

EXAMPLE 111

The surgical mechanical arm of Example 110, wherein said sheath covers a distal portion of said arm excluding said first and second portions.

EXAMPLE 112

The surgical system of Example 29, wherein said tool comprises:
a first surface electrically coupled to said first electrical conduction pathway; and
a second surface electrically isolated from said first surface and electrically coupled to said second electrical conduction pathway.

EXAMPLE 113

The electrosurgical tool of Example 43, wherein said second bipolar surface is configured to be brought into contact with said first bipolar surface.

EXAMPLE 114

The method of Example 76, wherein each said modular unit comprises:
  a motor unit; and
  a surgical arm actuated by, connected to and supplied with electrosurgical power by said motor unit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data.

Optionally, a network connection is provided as well. A display and/or a user input device such as a keyboard or mouse are optionally provided as well.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as providing control signals for actuation of a surgical mechanical arm, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 12A-B are simplified schematics of a surgical arm tool, according to some embodiments of the invention;

FIG. 12C is a top view of holding element of FIG. 12A, according to some embodiments of the invention;

FIG. 14A is a simplified schematic side view of a surgical arm jig, according to some embodiments of the invention;

FIG. 14B is an enlarged side view of a distal end of the jig illustrated in FIG. 14A;

FIG. 14C is a simplified schematic of a distal portion of a jig after covering with a coating 1410, according to some embodiments of the invention;

FIG. 14D is a simplified schematic side view of a distal portion of a jig disassembled for removal of a sheath, according to some embodiments of the invention;

DESCRIPTION OF SPECIFIC EMBODIMENTS OF THE INVENTION

Figure 1A:
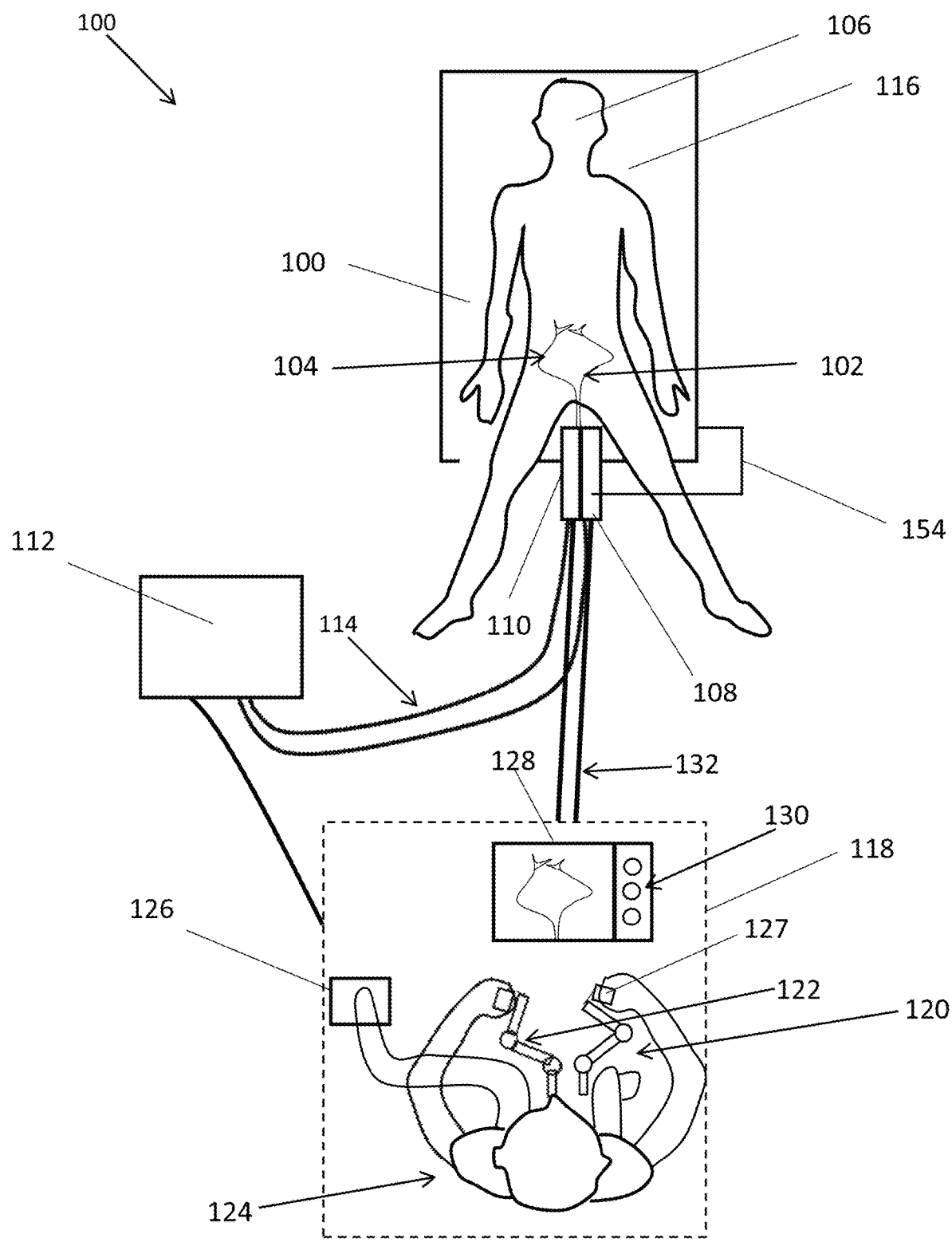
FIGS. 1A-B are simplified schematics of a surgical system, according to some embodiments of the invention.

The present invention, in some embodiments thereof, relates to an electro-surgical system and, more particularly, but not exclusively, to a combined monopolar and bipolar electro-surgical system.

Overview

A broad aspect of some embodiments of the invention relates to an electrosurgical system configured to perform both monopolar and bipolar electro surgery.

An aspect of some embodiments of the invention relates to a modular electrosurgical system capable of performing both monopolar and bipolar electrosurgery. In some embodiments, the system includes a plurality of surgical device modules, each module including a modular surgical arm configured to operate in both monopolar and bipolar operational modes. In some embodiments, a module includes a motor unit module configured to attach to, actuate and provide electrosurgical power to at least one modular surgical arm. In some embodiments, one or more modular unit is configured to attach to another modular unit e.g. in some embodiments, motor units are configured to be attached to each other.

In some embodiments, a surgical arm (e.g. a modular surgical arm) has a modular surgical tool, for example, disposed on a distal end of the surgical arm. In some embodiments, the tool is removed and/or replaced, optionally during use of the arm, for example, without detaching the arm from a motor unit.

In some embodiments, a single module is configured to operate in at least two operational modes, where, in a first mode, an arm tool includes a single charged portion, for monopolar operation, and in a second mode, where the arm tool includes a first charged portion and a second charged portion, for bipolar operation. In some embodiments, a modular unit is configured to operate in a third mode where the surgical arm is not charged and, for example, is used for mechanical manipulation and/or as a mount for a surgical instrument (e.g. for a camera).

In some embodiments, different modules are operated in different electrosurgical operational modes, for example, simultaneously and/or sequentially.

In some embodiments, a user selects an electrosurgical operational mode (e.g. bipolar or monopolar) for a modular unit by connecting a selected electrosurgical power supply to the modular unit and/or inputting a desired electrosurgical operational mode at a user interface e.g. a user interface of a control console and/or a user interface of a modular unit. In some embodiments, the user interface has a data connection with the modular unit (e.g. the motor unit). For example, a direct data connection and/or a connection via an external processor. In some embodiments, a processor, for example at the motor unit (and/or at a control console), checks that electrosurgical power supply to the unit matches an inputted desired operational mode. In some embodiments, if there is a match, power is supplied through the motor unit to the surgical arm.

In some embodiments, a bipolar operational mode includes a single modular unit, where a tool actuated by the unit has two portions each charged with a different polarity electrical charge. In some embodiments, a bipolar operational mode includes two modular units where a tool actuated by a first modular unit is charged with a first polarity and a second modular unit is charged with a different polarity, the two tools (each tool, for example, including an electrosurgical tip) being brought towards each other to apply bipolar electrical charge to tissue therebetween.

In some embodiments, an electrosurgical operational mode is selected and/or is changed when surgical arm/s are at a surgical zone and/or without moving surgical arm/s from a surgical zone within a patient's body.

An aspect of some embodiments of the invention relates to a motor unit which provides electrosurgical power supply to a surgical arm attached and/or actuated by the motor unit. In some embodiments, electrosurgical power supply (e.g. from an electrosurgical generator) passes through the motor unit, extending along the surgical arm to reach an electrosurgical tool.

In some embodiments, a first motor unit receives electrosurgical power from an electrosurgical power generator to which it is attached (e.g. by a cable) and the first motor unit then passes electrosurgical power supply to one or more additional motor units (which, in some embodiments, are not connected to the electrosurgical power generator).

In some embodiments, one or more motor unit includes an electrosurgical power generator e.g. housed within the motor unit.

In some embodiments, an electrosurgical power generator is attached to a control console, the generator, in some embodiments, not being directly to a motor unit. In some embodiments, one or more motor unit receives electrosurgical power supply from the control console.

In some embodiments, the motor unit includes one or more actuator which is coupled to the surgical arm and effects movement of the surgical arm, for example, effecting rotation and/or bending of one or more portion of the surgical arm.

In some embodiments, one or more electrosurgical power connection is coupled to portion/s of the surgical arm which are actuated by the motor unit. For example, in some embodiments, a surgical arm includes one or more gear coupled to one or more electrosurgical contact where the one or more gear is configured to be actuated by the motor unit. In an exemplary embodiment, the surgical arm includes a monopolar and a bipolar slip ring coupled to a gear. In some embodiments, the gear when rotated actuates movement of the surgical arm. In some embodiments, the gear provides electrical insulation between the slip rings, for example, in some embodiments, the gear is electrically insulating and/or has an electrically insulating coating.

An aspect of some embodiments of the invention relates to a surgical mechanical arm (e.g. an articulated surgical mechanical arm) including an electrosurgical tool, where a current path to the tool is provided by a body of the surgical mechanical arm. For example, in some embodiments, a monopolar electrosurgical tool is supplied with electrosurgical power through a body of an electrosurgical arm configured to move and/or actuate the tool. For example, in some embodiments, a portion of a bipolar electrosurgical tool is supplied with electrosurgical power through a body of the surgical arm. In some embodiments, an insulated wire supplies a second polarity of electrosurgical power to a second portion of the tool. In some embodiments, the body of the surgical arm is covered in an insulator (e.g. an insulating sheath), for example, so that electrosurgery occurs between the tool and tissue (e.g. that the tool is contacted to).

An aspect of some embodiments of the invention relates to an electrosurgical tool configured to be used for both monopolar and bipolar electro-surgery where a single portion of the electrosurgical tool is configured to be charged in both monopolar and bipolar operational modes.

In some embodiments, a first portion of the tool is configured to be charged during both monopolar and bipolar operation, and a second portion, configured to be charged only during bipolar operation, of the tool configured to be brought towards (and/or together and/or into contact) with at least part of the first portion is. In embodiments, where the tool is configured for the portions to be moved towards each other and/or together (for example, the tool portions do not contact each other) the minimum separation between the tool portions is small enough to effect bipolar electrosurgical treatment, of tissue placed within in the separation (e.g. cauterizing), when the portions are charged. Where, in some embodiments, the minimal separation is 0.01 mm-5 mm, or 0.1 mm-1 mm, or 0.1-0.5 mm, or about 0.2 mm or lower or higher or intermediate distances or rages.

In some embodiments, the second portion is electrically isolated from the first portion.

In some embodiments, the tool portions (e.g. first portion and the second portions) have a fixed position and/or shape. For example, the first and second portions, for at least a region of the portions, being close enough, to effect bipolar electrosurgical treatment, of tissue placed within in the separation (e.g. cauterizing), when the portions are charged. For example, in some embodiments the first and/or second portions have an elongated shape where tips of the portions have a sufficiently small separation for bipolar electrosurgical treatment. For example, in some embodiments, one or more of the tool portions is claw shaped. Where, in some embodiments, the minimal separation is 0.01 mm-5 mm, or 0.1 mm-1 mm, or 0.1-0.5 mm, or about 0.2 mm or lower or higher or intermediate distances or rages.

For example, in some embodiments, a tool includes a first portion which is charged in both monopolar and bipolar operation and a second portion which is only charged in bipolar operation, where the portions are moveable towards each other, in some embodiments, are moveable to be in close contact with each other. In an exemplary embodiment, the tool is a gripper. In some embodiments, the gripper includes two portions configured to be brought into contact with each other. In some embodiments, the gripper includes more than two portions configured to be brought into contact each other.

In some embodiments, the tool is a scissors where, for example, the first portion is a first blade of the scissors and the second portion is a second blade of the scissors. In some embodiments, the scissor blades are coupled by a pivot joint. In some embodiments, a first bipolar surface is disposed on a face of the first blade and a second bipolar surface is disposed of a face of said second blade, where, when the blades rotate towards each other (e.g. about a pivot connection). In some embodiments, a first bipolar surface is disposed on an edge of the first blade and a second bipolar surface is disposed of an edge of said second blade, where, when the blades rotate towards each other (e.g. about a pivot connection). In some embodiments, a first bipolar surface is disposed on an edge of the first blade and a second bipolar surface is disposed of a face of said second blade, where, when the blades rotate towards each other (e.g. about a pivot connection).

In some embodiments, the first portion includes a monopolar spatula sized and/or shaped for monopolar electrosurgery (e.g. monopolar cutting and/or monopolar coagulation) whilst being small enough and/or blunt enough for bipolar use of the tool.

In some embodiments, a tool includes two jaws (also herein termed "opposing portions") which are configured move towards each other. In some embodiments, the jaws are bipolar electrosurgical contacts, each jaw including a contact, the contacts electrically isolated from each other. In some embodiments, a jaw has a protruding bipolar portion (e.g. a bipolar spatula) which is electrically connected to the jaw on which it is disposed.

An aspect of some embodiments of the invention relates to a surgical tool including at least two portions, where the tool portions are configured to be brought towards and away from each other at different speeds and/or for a different amount of actuation provided by an actuator. In some embodiments, the tool is actuated (the portions moved towards and/or away from each other) by rotation of a portion (e.g. elongated portion) coupled to the tool, where, for example, a different number of rotations and/or angle of rotation for the portion is required to open than is required to close the tool and/or is required to move the tool portion/s during different parts of their movement. In some embodiments, the tool is actuated by an additional or alternative method, for example, in some embodiments, a change in tension on one or more portion coupled to the tool actuates the tool, different changes in tension being required to close the tool and/or is required to move the tool portion/s during different parts of their movement.

In some embodiments, the tool includes a first surface (of a first portion) which moves in contact along a second surface (of a second portion), where, in some embodiments, the movement is due to linear movement of the portions with respect to each other. The movement is, in some embodiments, sliding of the first surface against the second surface, and, in some embodiments, rolling of the first surface along the second surface. In some embodiments, the first surface is convex and the second surface is concave, or vice versa. In some embodiments, one of the surfaces is fixed by a pivot the portion rotating about the pivot as the surfaces are moved along each other. In some embodiments, the first and second surfaces are shaped to generate a moment about the pivot. In some embodiments, a gradient of the surfaces is higher in one portion that the other, the first portion generating a moment in one direction and the second portion generating a moment in a different direction. In an exemplary embodiment, the higher gradient portion generates a moment to close the tool which is, for example, a gripper or scissors. In some embodiments, the tool includes two such pairs of surfaces, for movement of two portions of a tool (e.g. two opposing gripper portions, two scissors blades) towards each other.

In some embodiments, the first surface is fixed about the pivot and/or has a shape which is two overlapping circles with different radii (which in some embodiments, is an outer surface of an opposing portion of a gripper).

In some embodiments, the tool is actuated by linear movement of a holder with respect to the tool portions which move towards and/or away from each other e.g. opposing portions of a gripper tool (and/or blades of a scissor tool). Where, for example, in some, embodiments, relative linear movement between the holder and the tool portion/s generates rotational movement of the portion/s e.g. about a pivot. In some embodiments, the shape of portions of the holder with respect to the tool portions where the holder and tool portions contact each other has different gradients. Each gradient, for example, corresponding to a different rate of opening and/or closing movement of the tool portions for a same amount of linear movement between the holder and the tool portion/s (e.g. actuation applied).

An aspect of some embodiments of the invention relates to one or more tubular portion of a surgical am coupled to an electrosurgical tool providing a current path for the electrosurgical tool. In some embodiments, a portion of an arm which actuates a surgical tool is used to supply electrosurgical power to the tool. In some embodiments, more than one portion of an arm which actuates a surgical tool is used to supply electrosurgical power to the tool.

In some embodiments, an elongated element, the rotation of which (e.g. about an elongated element long axis) actuates the tool (e.g. opens and closes the tool) and forms an electrosurgical power supply path to the tool. In some embodiments, the elongated element is not electrically isolated from other portions of the surgical arm, a body of the arm forming a first electrosurgical path for a first portion of an electrosurgical tool. In some embodiments, the elongated element is capable of transferring torque and in some embodiments is capable of transferring torque when it is bent in one or more place, e.g. by the mechanical surgical arm when the elongated element passes through the arm thereby being bent by bending of the arm. In an exemplary embodiment, the elongated element is a torque cable.

In some embodiments, the first electrosurgical path is live in both monopolar and bipolar operational modes. In some embodiments, in a bipolar electrosurgical mode a second electrosurgical path, which provides power to a second portion of an electrosurgical tool, is electrically isolated (e.g. by an insulating coating and/or sheath) from the first electrosurgical path. In some embodiments, the second portion is electrically isolated from the first portion of the electrosurgical tool. In some embodiments, the second electrosurgical path also includes one or more element which actuates a portion of the arm e.g. the electrosurgical tool.

In some embodiments, the surgical arm has a plurality of joints, for example, which, in some embodiments, include one or more slip rings.

A broad aspect of some embodiments of the invention relates to electrical isolation of a surgical arm (e.g. from patient tissue). In some embodiments, an elastic sheath covers a portion of a surgical mechanical arm. In some embodiments, the sheath is sized to extend from a base of the surgical arm where it abuts a motor unit to an electrosurgical tool at a distal end of the surgical arm. Alternatively or additionally, in some embodiments, the sheath extends to cover a portion of the arm which is inserted into the motor unit. In some embodiments, the sheath covers all of a proximal end of the arm. In some embodiments, the sheath additionally covers at least a portion of the motor unit. In some embodiments, the sheath connects with a surgical drape covering the motor unit. In some embodiments, a sheath also provides a sterile surface and/or fluid sealing and/or sterile separation between the arm and/or motor unit and patient tissue. In some embodiments, an extension of the sheath and/or an additional sheath covers internal portion/s of a surgical arm, e.g. one or more inner tube and/or extension of the surgical, potentially, insulating (e.g. one or more of electrical, fluid, sterile) portions of the arm from each other.

In some embodiments, the sheath is sized to closely fit the surgical arm, for example, having one or more inner dimension which is the same or smaller than an outer dimension of a surgical arm. In some embodiments, the surgical arm includes a tool, which is, for example, coupled to a distal end of the surgical arm. In some embodiments, at least a portion of the tool is covered with a sheath, and, in some embodiments, at least a portion of the tool is covered with an extension of a sheath covering at least a portion of a body of the surgical arm. In some embodiments, the sheath includes more than one portion. In some embodiments, the sheath divides into a plurality of sections, for example, bifurcating into two portions, similar to a pair of trousers, which are sized and shaped to partially cover portions of a tool with two portions coupled to the surgical arm.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Electrosurgical System

Figure 1B:
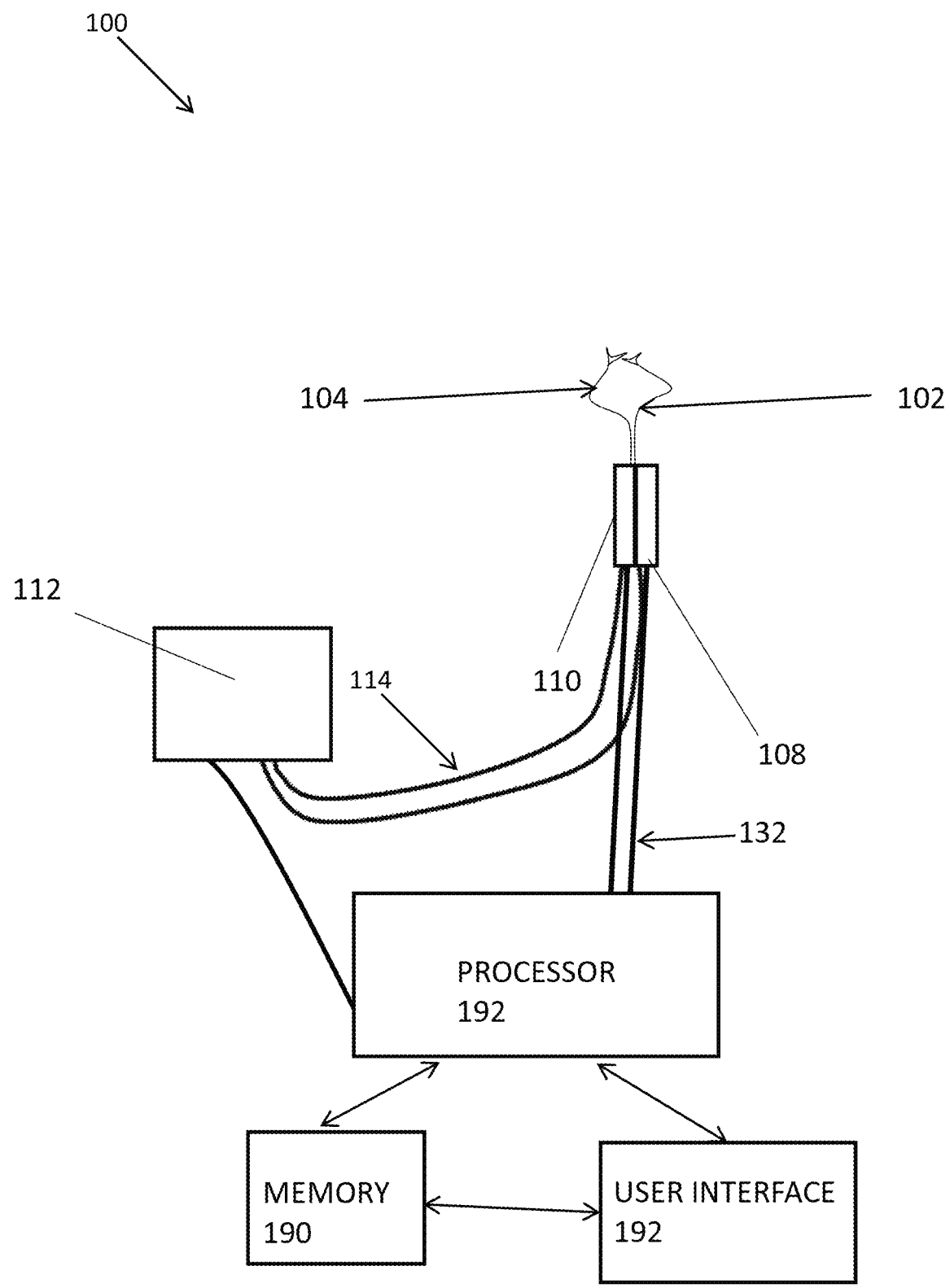

FIGS. 1A-B are simplified schematics of a surgical system 100, according to some embodiments of the invention.

Referring now to FIG. 1A, in some embodiments, surgical system 100 includes at least one surgical mechanical arm, for example, a plurality of surgical mechanical arms 102, 104. In some embodiments, surgical mechanical arms are sized and/or shaped for insertion into a human body 106.

In some embodiments, the system includes at least one motor unit, for example, a plurality of motor units 108, 110, where each of surgical mechanical arms 102, 104 is actuated by a motor unit. For example, where a first surgical arm 102 is actuated by a first motor unit 108 and/or a second arm is actuated by a second motor unit 110.

A potential benefit of the device being coupled to a bed is the ability to move and/or change an angle of the bed, for example, during surgery, while the device remains in the same position relative to the bed and/or patient. Alternatively, or additionally, in some embodiments, a device position with respect to the patient and/or the bed is adjustable, for example, before treatment with the device and/or during surgery.

In the embodiment illustrated by FIG. 1A, support arm 154 and the motor unit housings are located at the foot end of patient support 116. A potential benefit of this location is ease of surgery through a patient's undercarriage, for example, through the vagina.

In FIG. 1A, patient 106 is illustrated in a suitable position for insertion of the device into the vagina, the patient's legs apart (e.g. elevated and held apart e.g. held by stirrups which are not shown).

In some embodiments, the surgical arms and/or motor units are supported by attachment to a patient support 116 (which is, for example, a patient bed).

In some embodiments, a surgical mechanical arm is supplied with power by a motor unit to which it is attached. In some embodiments, surgical arm/s are supplied with power by an electrosurgical generator 112. In some embodiments, for example, as known in the art of electrosurgery, electrosurgical generator supplies high-frequency (e.g. radio frequency) alternating polarity, electrical current. In some embodiments, the electrosurgical generator is configured to supply different frequencies and/or powers, for example, suitable for cutting and/or coagulating and/or desiccating and/or fulgurating tissue. For example, in an exemplary embodiment, electrosurgical generator 112 is a Covidien Force FX ESU Electrosurgical Generator. In some embodiments, supply to the motor units is via cable/s 114 which are, for example, configured to transfer radio frequency electrosurgical power.

In some embodiments, surgical arms 102, 104 are controlled at a control console 118. In some embodiments, movement of surgical arms 102, 104 is controlled. In some embodiments, electrosurgical charging of arms 102, 104 is controlled.

In some embodiments, control console 118 includes a plurality of user interfaces: In some embodiments, control console 118 includes one or more input device arm 120, 122 where the control console is configured to generate control signals upon movement of the arm/s (e.g. in some embodiments, the arms generate control signals when moved). In some embodiments, one or more input device arm includes an additional user interface (not illustrated), for example, one or more button and/or switch.

In some embodiments, control console includes a display 128. In some embodiments, display 128 is configured to display imaging of a surgical zone, for example, to display images collected by a camera inserted into patient 106 with surgical arms 102, 104. In some embodiments, display is a touch screen configured to receive user input, potentially providing an additional user input.

In some embodiments, control console 118 includes one or more additional user interface 130 (e.g. button, switch).

In some embodiments, control console 118 includes a processor configured to receive signals from user input/s and to send control signals to motor units 108, 110 and/or electrosurgical generator 112. In some embodiments, foot pedal 126 and/or electrosurgical generator 112 include a processor configured to receive control signals (e.g. generated by a user pressing on portion/s of the foot pedal) to vary electrical power supplied to motor units 108, 110 based on the control signals. In some embodiments, foot pedal control signals do not pass through a control unit processor.

In some embodiments, the movement of input device arms 120, 122 controls movement of a surgical device arm. In some embodiments, a first input device arm 120 controls movement of first surgical arm 102 and/or a second input device arm controls movement of second surgical arm 104. In some embodiments, a user 124 controls movement of surgical device arms 102, 104 by moving input device arms 120, 122. In some embodiments, a user positions and/or moves an input arm by grasping an input device arm handle 127.

In some embodiments, a system includes an electrosurgical switching unit, for example, connected between electrosurgical generator 112 and motor units 108, 110 which, for example, switches electrosurgical power supply from the electrosurgical generator, for example, upon receiving a signal (e.g. from a electrosurgical switching unit user interface and/or from an external processor).

Referring now to FIG. 1B, in some embodiments, a surgical system includes a plurality of mechanical surgical arms 102, 104, actuated by motor units 108, 110 and supplied with power by an electrosurgical generator 112. In some embodiments, a processor receives an indication of a selection of an electrosurgical operational mode, for example, for each of the surgical arms 102, 104, and/or motor units 108, 110. In some embodiments, the processor receives an indication from a user interface 192 and/or from electrosurgical power generator 112, and/or from the motor units e.g. in some embodiments, the processor receives an indication of an electrosurgical operational mode from more than once source.

In some embodiments, the processor stores the indication/s in a memory 190. In some embodiments, the indication is stored mechanically, for example, by a switch. In some embodiments, an indication from each source is stored separately. In some embodiments, the processor compares indications from different sources, for example, before allowing supply (e.g. by sending a control signal) of electrosurgical power to one or more motor unit.

In some embodiments, functionality of processor 192 as described hereinabove is hosted by more than one processor. In some embodiments, processor/s are located in one or more motor unit and/or the electrosurgical generator, and/or in a control console (e.g. control console 118 FIG. 1A).

In some embodiments, control console 118 is connected to electrosurgical generator 112 and not directly to the motor units 108, 110. Where, for example, in some embodiments, control signals for control of actuation of the surgical arms by the motor units being received by the motor units from the electrosurgical generator (there being, in some embodiments, a data connection between the motor units and the electrosurgical generator).

Exemplary Surgical Mechanical Arm

Figure 2:
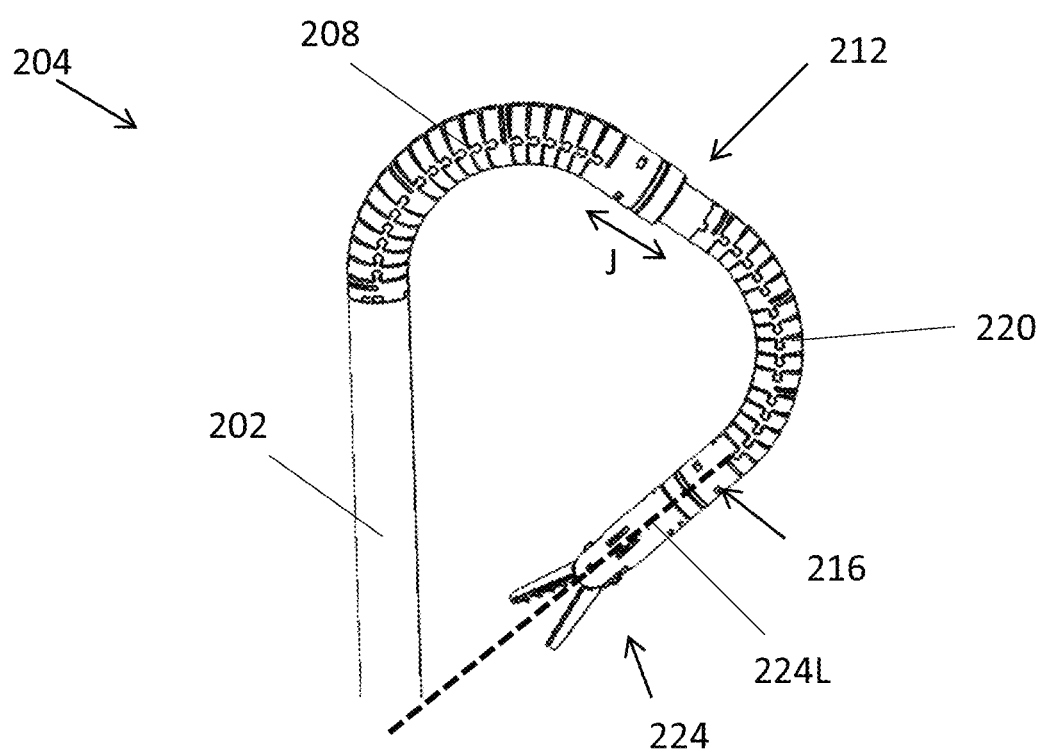
FIG. 2 is a simplified schematic side view of a surgical arm, according to some embodiments of the invention.

FIG. 2 is a simplified schematic side view of a surgical arm, according to some embodiments of the invention.

In some embodiments, a surgical arm is sized and/or shaped for insertion into a human body. For example, sized and/or shaped for insertion through a laparoscopic port and/or for performing laparoscopic surgery. For example, sized and/or shaped for insertion through a natural body orifice, e.g. vagina, anus, trachea, esophagus, ear canal.

In some embodiments, arm 204 includes a proximal and a distal end, a support segment 202 at a proximal end of the arm, coupled to a first segment 212 by a first connecting section 208, where first segment 212, is coupled to a second segment 216, by a second connecting section 220, and a third segment 224, is coupled to second segment 216. In some embodiments, third segment 224, at a distal end of the arm, is coupled to second segment by a third connecting section (not shown).

In some embodiments, segments 202, 212, 216 are rigid. Alternatively, in some embodiments, segments (e.g. support segment 202) are flexible or include a flexible portion.

In some embodiments, a surgical arm has a humanoid like structure. For clarity, in some portions of this document, device segments and connecting sections are referred to by anatomical names: Support segment 202 is also termed torso 202, first connecting section 208 is also termed shoulder joint 208, first segment, 212, is also termed humerus, second connecting section 220 is also termed elbow joint 220, second segment 216 is also termed radius 216 third segment 224 is also termed hand tool 224.

In some embodiments, one or more connecting section includes a hinge. In some embodiments, one or more connecting section is flexible and/or includes a flexible portion. In an exemplary embodiment, a device arm includes an elbow joint and a shoulder joint where bending of the joint is distributed along the joint in a direction of a joint long axis. In some embodiments, one or more connecting portion is long where a long axis length of the connecting portion is at least double a maximal cross sectional dimension of the portion.

In an exemplary embodiment, surgical device segment thickness is 6-8 mm, or 4-8 mm, or 4-6 mm or lower, or higher or intermediate ranges or thicknesses. In some embodiments, surgical device segment thickness is 0.1-5 mm, 0.5-3 mm, or 0.1-1 mm, or lower or higher or intermediate ranges or thicknesses. In some embodiments, a minimum radius of curvature of one or more flexible portion is 1-15 mm, or 3-10 mm, 7-10 mm, or lower or higher or intermediate radius of curvatures or ranges. In some embodiments, a radius of curvature is less than 5 mm, or 3 mm, or 1 mm.

In some embodiments, one or more device segment has a substantially tubular external shape (e.g. radius, humerus). In some embodiments, connecting portions have circular long axis cross-section. Alternatively, in some embodiments, one or more device segment and/or joint has non-circular cross section external shape, for example, oval, square, rectangular, irregular shapes.

In some embodiments, flexible portions are directly connected.

In some embodiments, a flexible portion comprises a plurality of stacked links.

In some embodiments, a user selects arm/s including desired size/s and/or segment lengths, where for example, selection is based on patient anatomy and/or a procedure to be performed. For example, when treating a child a user, in some embodiments, selects one or more arm with one or more short segment. For example, when treating an obese patient, a user, in some embodiments, selects an arm with one or more a long segment. In some embodiments, a device includes a kit with different structured arms (e.g. different segment lengths, e.g. different arm sizes).

Alternatively or additionally, in some embodiments, one or more segment length is adjustable, e.g. during a treatment and/or during set-up of the device. For example, in some embodiments, a length "J" (see FIG. 2) is adjustable.

In some embodiments, a device arm has at least the freedom of movement of human arms.

In some embodiments, one or more flexible portion is bendable and extendable in a single bending plane. In some embodiments, one or more flexible portion is bendable in one direction in the first bending plane, from a straight configuration. In some embodiments, flexible portion/s are separably bendable and/or rotatable.

In some embodiments, an orientation of portions of the arm distal of a flexible portion is changed by rotating the flexible portion around a flexible portion long axis.

Generally, human freedom of movement for arms includes limits to the angles of rotation and flexion. Optionally, in some embodiments, the device is restricted to human freedom of movements. Alternatively, the device is configured to allow movement having additional degrees of freedom relative to human arm movement. For example, in some embodiments, flexible portions are rotatable by more than 180°, for example are infinitely rotatable.

Figures 3A, 3B:
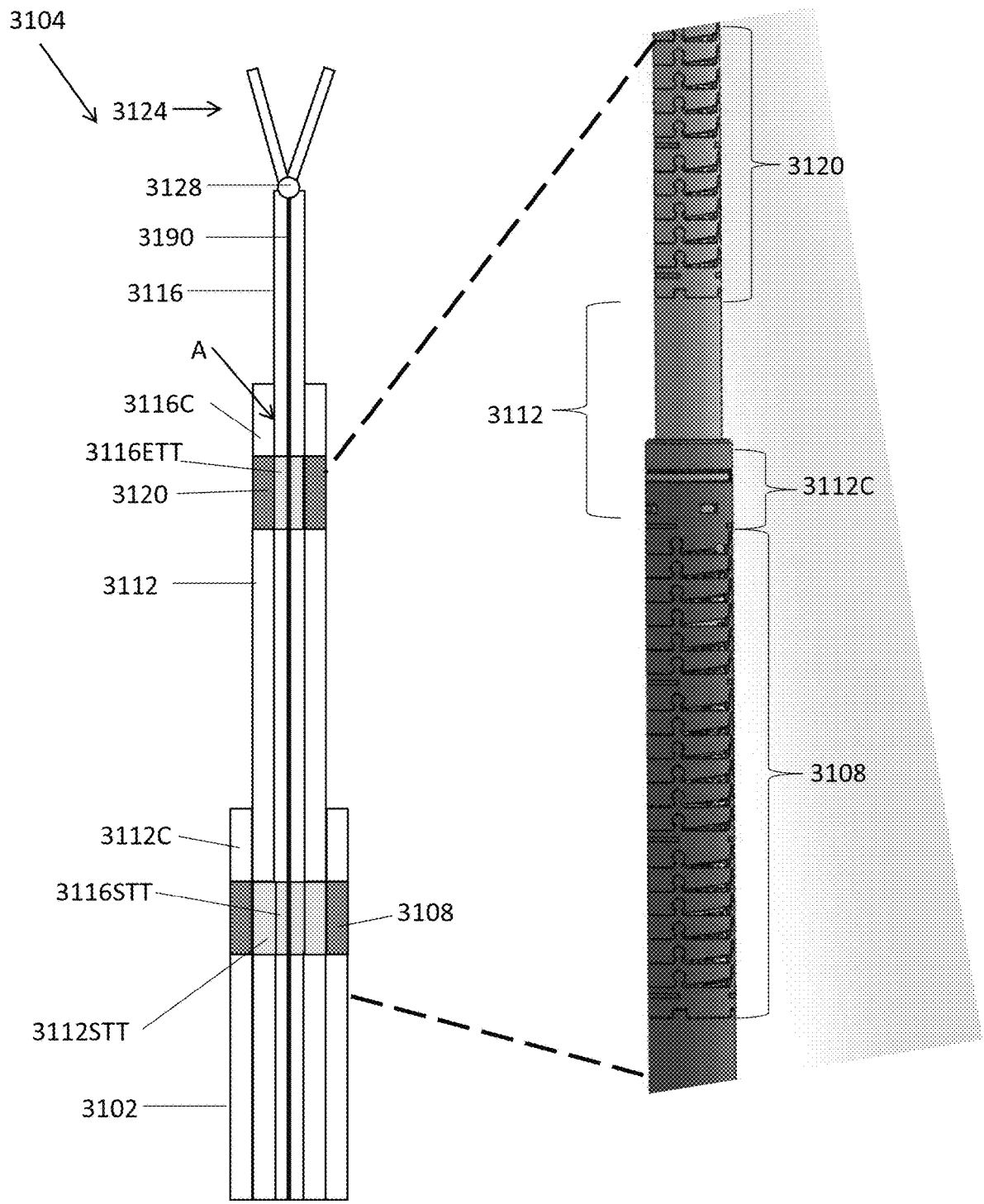
FIG. 3A is a simplified schematic cross sectional view of an arm with nested segment extensions, according to some embodiments of the invention.
FIG. 3B is a simplified schematic of a side view of a portion of an arm, according to some embodiments of the invention.

FIG. 3A is a simplified schematic cross sectional view of an arm 3104 with nested segment extensions, according to some embodiments of the invention. FIG. 3B is a simplified schematic of a side view of a portion of an arm, according to some embodiments of the invention. Dashed lines illustrate the portion of the arm in FIG. 3A illustrated by FIG. 3B.

In some embodiments, arm 3104 includes a hand tool 3124 coupled to a radius 3116 at a wrist joint 3128.

In some embodiments, radius 3116 is coupled to a radius extension including two torque transfer portions; an elbow torque transfer portion 3116ETT disposed inside an elbow joint 3120 and a shoulder torque transfer portion 3116STT disposed inside a shoulder joint 3108. In some embodiments, radius 3116 is coupled to a humerus 3112 by a connector 3116C. In some embodiments, portion 3116C connects radius 3116 to humerus 3112 whilst allowing free rotation of humerus 3112. In some embodiments, at region A of FIG. 3A, protrusion/s on radius portion 3116 fit into indentation/s on portion 3116C. In an exemplary embodiment, a ring shaped protrusion on radius portion 3116 (e.g. a ring of material connected (e.g. welded) to radius portion 3116) fits into an indentation on portion 3116C. Similarly, in some embodiments, portions 3112C and 3112 are connected by matching protrusion/s and indentation/s (e.g. a ring protrusion on portion 3112 fitting into a matching indention in portion 3112C).

In some embodiments, a "connecting section" includes a connector and a joint, for example shoulder joint 3108 and connector 3112C, for example elbow joint 3120 and connector 3116C.

Figure 3C:
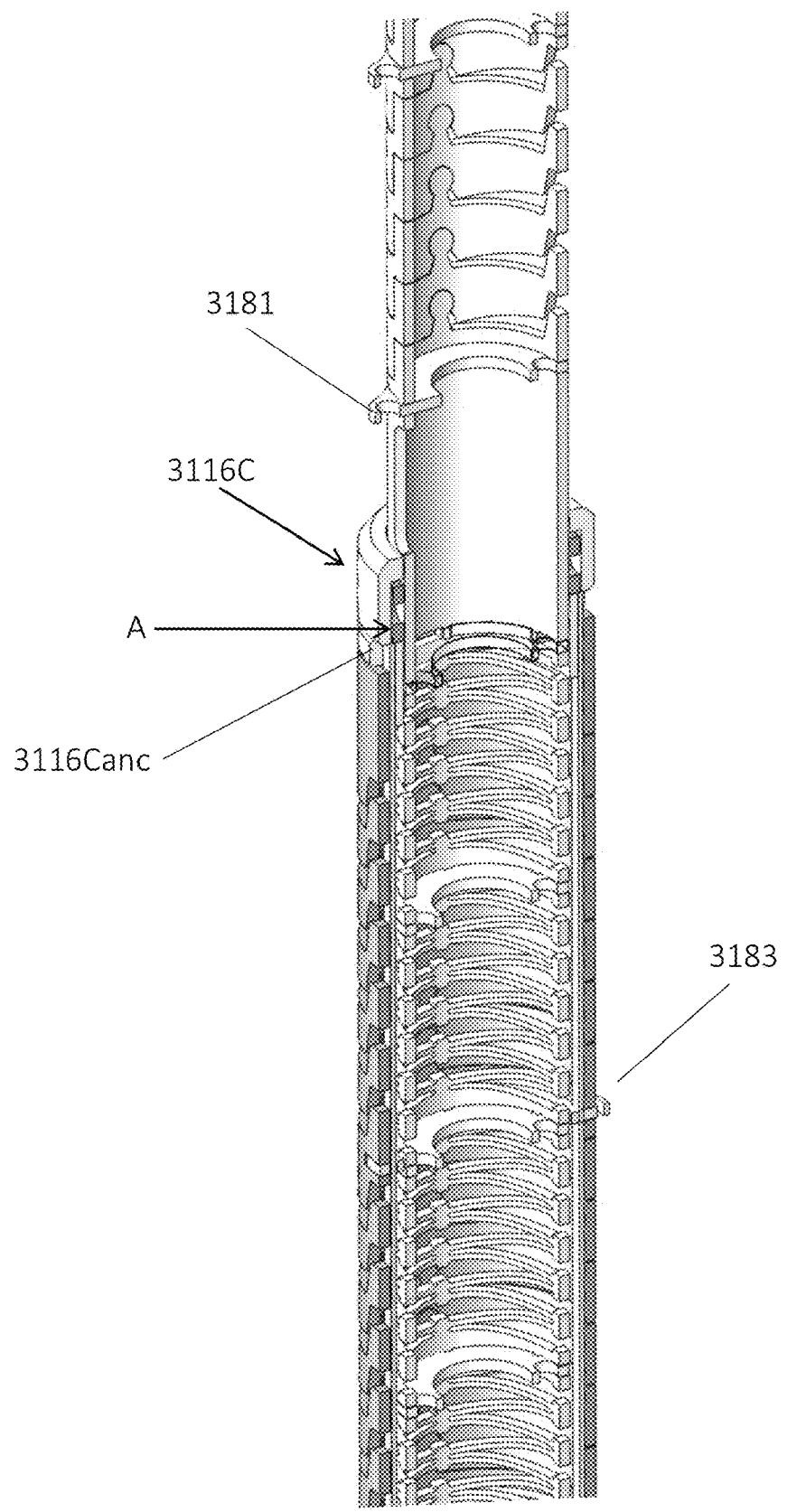
FIG. 3C is a simplified schematic cross sectional view of a portion of an arm, according to some embodiments of the invention.

FIG. 3C is a simplified schematic cross sectional view of a portion of an arm, according to some embodiments of the invention. In some embodiments, for example, a portion includes a ring protrusion which fits into an indentation on portion 3116C.

In some embodiments, portion 3116C provides anchoring to one or more elongated element: for example, where elongated element/s (e.g. a cable, a wire, a tape) are connected/coupled to portion 3116Canc.

In some embodiments, one or more connector couples portions whilst allowing one portion to rotate within the connector about the portion's long axis. For example connecting portion 3116C allows radius 3116 to rotate within connecting portion 3116C about a radius long axis.

In some embodiments, humerus 3112 is coupled to a humerus extension including one torque transfer portion, a shoulder torque transfer portion 3112STT disposed inside shoulder joint 3108. In some embodiments, the humerus is coupled to a torso 3102 by a connector 3112C.

In some embodiments, a surgical arm includes a first and a section flexible portion (e.g. elbow joint and shoulder joint) which are coupled together with a short connecting segment (e.g. a humerus section coupling a shoulder and elbow joint is short). In some embodiments, coupling between the flexible portions is a point connection (e.g. a shoulder and elbow joint are directly connected).

In some embodiments, a rigid anchoring portion (e.g. portion 3116C) connects two flexible portions, where the anchoring portion provides anchoring of elongated elements which control flexion and extension of the joint which is, for example, proximal to the elongated element. In some embodiments, anchoring is provided by a portion of one of the joints, e.g. a distal portion of the proximal joint.

In some embodiments, one or more shafts (or portions thereof) of the surgical arm are rigid. In some embodiments, a flexible shaft is nested within a rigid outer shaft. In some embodiments, the outer shaft is flexible to a lower extent than the inner shaft.

In some embodiments, actuation of hand tool 3124 (e.g. opening and/or closing of the hand tool) is by rotation of a hand tool extension 3190 (e.g. as described below, e.g. with reference to FIG. 3A). In some embodiments hand tool extension 3190 extends through the arm and is able to transfer torque applied along its length (e.g. at a proximal base of the hand tool extension). In some embodiments, had tool extension 3190 is a torque cable and in an exemplary embodiment as a 1 mm torque cable (e.g. as supplied by Fort Wayne Metals).

In some embodiments, tools and/or electrosurgical connections and/or the system (e.g. as described in FIG. 1A) are suitable for use and/or combination with other surgical mechanical arms of the art (e.g. suitable for use with robotic arms of the art).

In some embodiments, a surgical mechanical arm includes a plurality of sequentially coupled segments coupled by joints where flexion of one or more segment about one or more joint and/or rotation of a segment is actuated by actuation elements located at the segments and/or at the joints. For example, in some embodiments, actuation element/s, including, for example, gear/s and/or motors. In some embodiments, actuation elements are located within (e.g. a hollow portion thereof) segment/s and/or joint/s. In some embodiments, e.g. as described elsewhere in this document, the surgical arm supplies electrosurgical power to an electrosurgical tool disposed on the arm using a first current path which includes portion/s of the arm (e.g. a body of the arm and/or one or more part of the arm which actuates one or more other part of the arm). In some embodiments, a second current path to the tool is an electrically isolated wire, which for example, runs through hollow portions of the arm.

In some embodiments, where portions of the arm form an electrical path (e.g. portion/s of the body of the arm including one or more segment) actuation element/s are electrically insulated from the current path.

In some embodiments, a surgical mechanical arm includes a plurality of sequentially coupled segments coupled by joints where flexion of one or more segment about one or more joint and/or rotation of a segment is controlled by controlling tension (e.g. using one or more actuator e.g. located within a motor unit) on one or more elongated portion attached to the segment/s and/or joint/s. In some embodiments, changes in tension on elongated elements are actuated by actuators (e.g. motors) located at a base or proximal end of the surgical arm, where, in some embodiments, arm tool/s are located at a distal end of the surgical arm. In some embodiments, e.g. as described elsewhere in this document, the surgical arm supplies electrosurgical power to an electrosurgical tool disposed on the arm using a first current path which includes portion/s of the arm (e.g. a body of the arm and/or one or more part of the arm which actuates one or more other part of the arm e.g. one or more the elongated portions which are tensioned by the motor unit). In some embodiments, a second current path to the tool is an electrically isolated wire, which for example, runs through hollow portions of the arm. In some embodiments, electrosurgical power supply is supplied through contacts in the motor unit.

In some embodiments, a surgical arm is an elongate rigid element with a surgical (e.g. electrosurgical) tool located at a distal end of the arm. In some embodiments, position of the tool is controlled by changing a position of a proximal end of the arm, the arm, in some embodiments, pivoting around a point between the distal and proximal ends (in some embodiments, the pivot point is a port into a patient's body). In some embodiments, actuator/s (e.g. located within a motor unit to which the arm is attached) are configured (e.g. automatic actuation controlled by a processor which, for example, receives control signals from a user input) to change a position of the proximal end of the surgical arm. In some embodiments, e.g. as described elsewhere in this document, the surgical arm supplies electrosurgical power to an electrosurgical tool disposed on the arm using a first current path which includes portion/s of the arm (e.g. a body of the arm). In some embodiments, a second current path to the tool is an electrically isolated wire, which for example, runs through hollow portions of the arm. In some embodiments, electrosurgical power supply is supplied through contacts in the motor unit.

Exemplary Support

Figure 4:
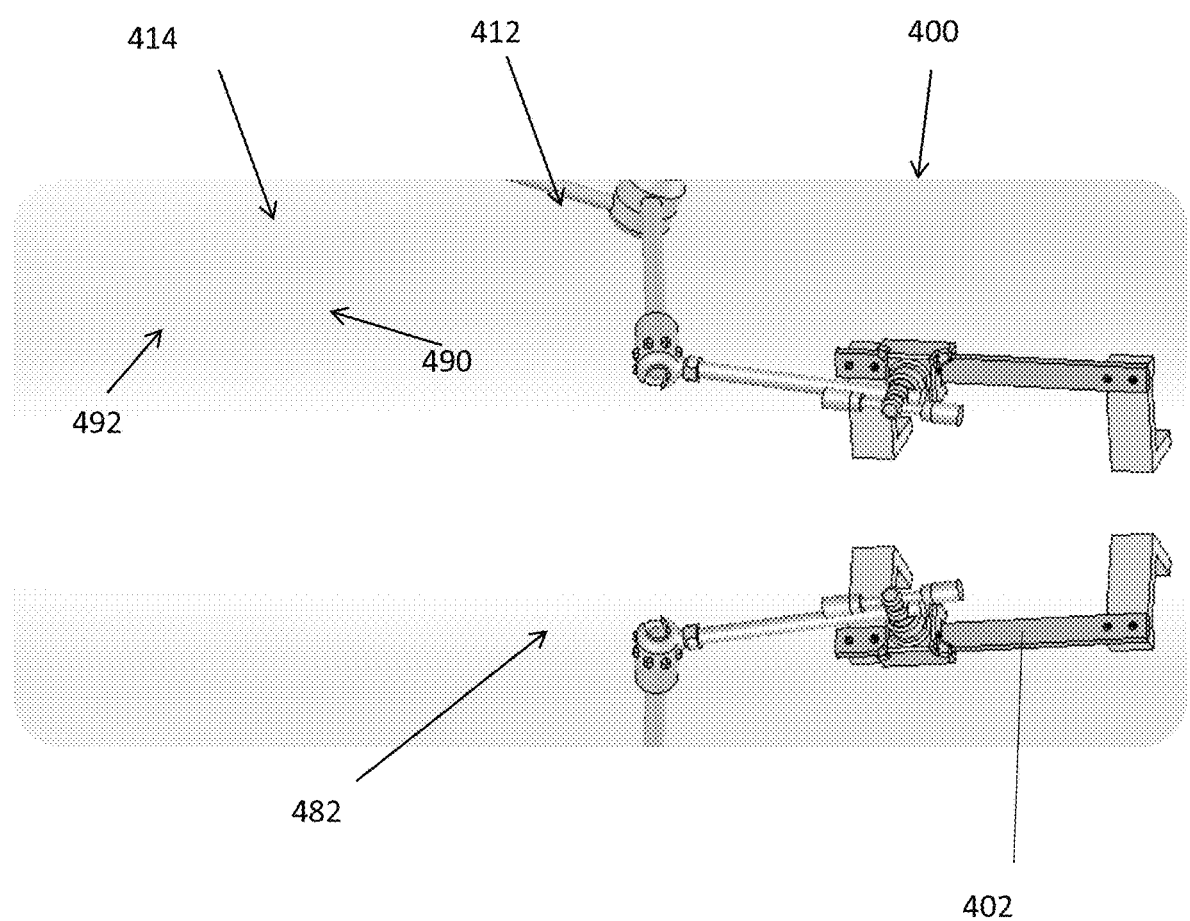
FIG. 4 is a simplified schematic of a surgical device, held by a support, according to some embodiments of the invention.

FIG. 4 is a simplified schematic of a surgical device 400, held by a support 482, according to some embodiments of the invention.

In some embodiments, support 482 attaches to a portion of a patient operating surface, e.g. rail 402. In some embodiments, position of attachment of support 482 on rail 402 is adjustable, for example enabling linear adjustment of position of attachment of the support to the patient operating surface.

In some embodiments, support 482 is attached to port 412 of a motor construct 414, device 400 being supported by attachment to motor construct 414. In this example, motor construct 414 comprises two motor units configured for actuating two arms of device 400, according to some embodiments. It is noted that in some embodiments, the device comprises a different number of arms such as 1, 3, 4, 6, 8 arms or intermediate, higher or lower number. Optionally, each arm is actuated by a respective motor unit.

In some embodiments, port 412 is placed at an opening to the patient's body, for example at an incision and/or at a natural body orifice such as the vagina and/or anus and/or mouth. In some embodiments, port 412 is attached to the patient's body using sutures and/or other attachment means. Additionally or alternatively, port 412 is fixated to the operating surface 402.

In some embodiments, support 482 includes a plurality of articulations where angles between segments and/or segment lengths are adjustable, for example, enabling adjustment of position and/or angle of a device 400 including surgical arms and/or a port 412 and/or motor construct or construct 414 (e.g. which actuate device 400 arm/s).

In some embodiments, one or more motor is used to move device 400, with respect to one or more portion of the system (e.g. with respect to port 412 and/or motor construct 414), for example, into and/or out of a patient. In some embodiments, motor construct 414 includes one or more motor for movement of one or more device arm with respect to the motor construct, where, for example, one or more support segment position is changed with respect to the motor construct.

In some embodiments, support 482 is configured to move motor construct 414 linearly, for example to advance device 400 into and/or out of the patient's body. In some embodiments, linear movement is obtained by a linear unit 490.

In some embodiments, movement of device 400 is controlled by a user, optionally using input object control and/or a user interface.

In some embodiments, the motor unit includes one or more position sensor. In some embodiments, a position sensor is placed adjacent the motor for sensing a current rotation angle of the motor. In some embodiments, the position sensor is magnetically operated, using a magnet placed on the motor gear and sensing the magnetic flux to determine a current position of the motor gear.

In some embodiments, the motor unit is controlled by a processor including a memory which stores commands. In some embodiments, data from position sensor/s and/or from control memory is used to infer a position of device portion/ s. In some embodiments, the motor unit is controlled by a processor configured in the user's input device.

In some embodiments, motor unit includes structure (e.g. including electrical contact/s), for example, for delivery of monopolar and/or bipolar energy to the device (e.g. to a device end effecter).

Exemplary Actuation of Exemplary Surgical Arm

Figure 5:
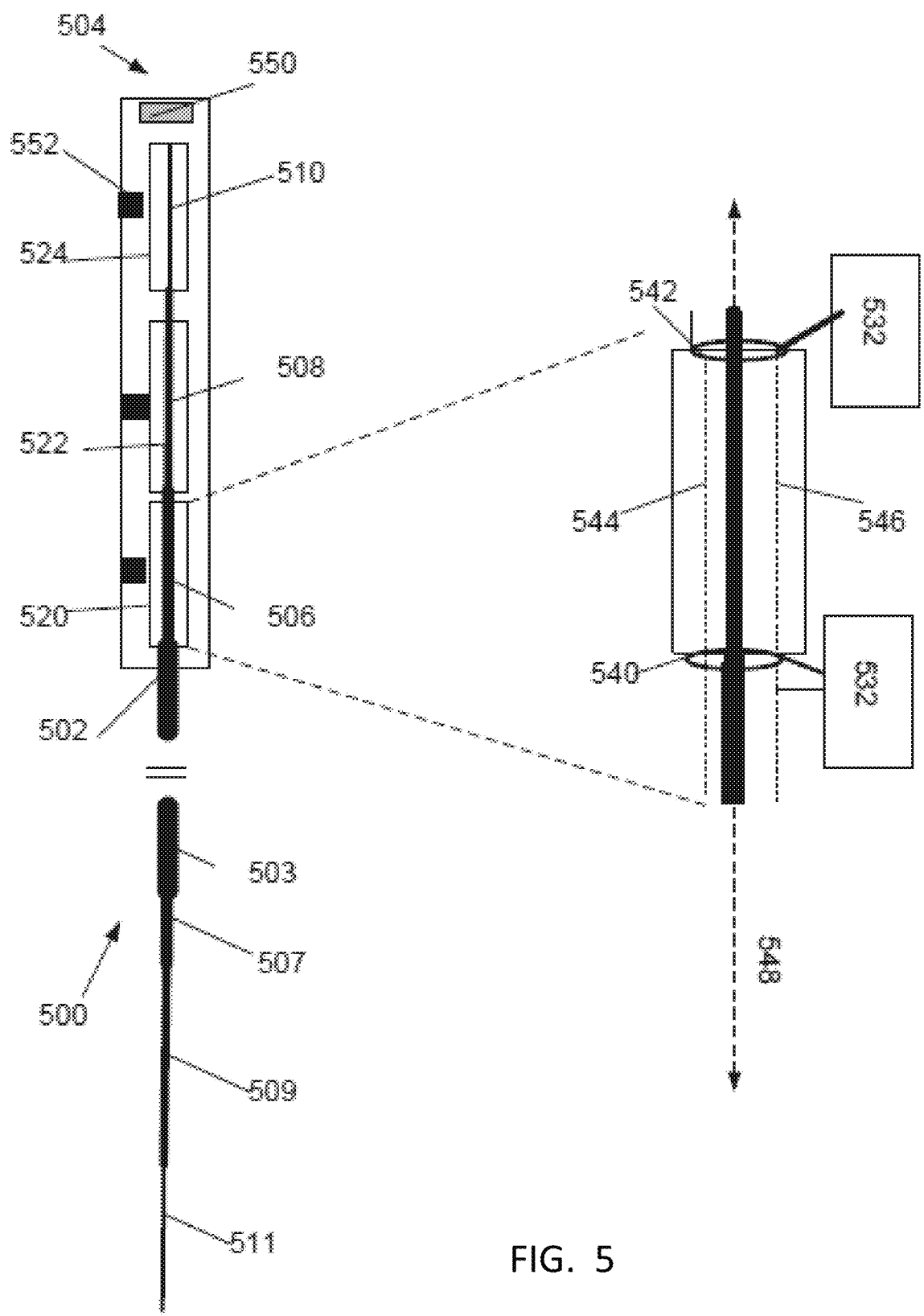
FIG. 5 schematically illustrates actuation of a surgical arm, according to some embodiments of the invention.

FIG. 5 schematically illustrates actuation of a surgical arm 500, according to some embodiments of the invention.

In some embodiments, a proximally extending shaft extension 502 (e.g. an extension of a torso 503) of arm 500 is attached to a motor unit 504. In some embodiments, proximal shaft extensions of arm segments that are nested within extension 502 (e.g. a proximal shaft extension 506 of humerus 507, a proximal shaft extension 508 of radius 509 that is nested within humerus extension 506, a proximal shaft extension 510 of a hand portion 511 that is nested within radius extension 508, and so forth) are actuated by a plurality of actuation mechanisms of the motor unit, such as 3 actuation mechanisms 520, 522 and 524. In some embodiments, the number of actuation mechanisms is set in accordance with the number of joints of the arm, for example, as shown herein, an arm including 3 joints (e.g. shoulder, elbow and wrist joints) is actuated by 3 actuation mechanisms, an arm including 4 joints is actuated by 4 actuation mechanisms, an arm including 2 joints is actuated by 2 actuation mechanisms, an arm including 1 joint is actuated by a single actuation mechanism.

In some embodiments, an actuation mechanism 520 (shown in the enlarged view) is configured to move at least a segment of arm 500, for example rotate the segment and/or bend the segment and/or otherwise move the segment. In some embodiments, an actuation mechanism comprises one or more actuators, for example 1, 2, 3, 4, 5 and/or 6 actuators. In some embodiments, the actuators are independently operable, yet, in some embodiments, a shaft manipulation (e.g. rotation, bending) obtained by a first actuator effects control of one or more other actuators.

In some embodiments, actuators of the same actuation mechanism are actuated together. Additionally or alternatively, actuators of different actuation mechanisms are actuated together, for example to provide for articulation of a proximal arm segment, a distal arm segment (which is at least partially nested within the proximal arm segment) needs to be moved as well. In an example, to provide for flexion of the shoulder, a bending actuator of an elbow is actuated as well.

In some embodiments, for example as shown herein, shaft extensions 502 and 506 (which is nested, in part, within shaft extension 502) are received within actuation mechanism 520. In some embodiments, actuation mechanism 520 comprises a first actuator 540, and a second actuator 542. In some embodiments, first actuator 540 is configured to rotate an arm portion, such as rotate the torso by rotating shaft extension 502 around its axis. In some embodiments, second actuator 542 is configured to bend an arm portion, such as bend a shoulder joint at a distal end of the torso (not shown herein). Optionally, bending is achieved by respective linear movement of elongate elements 544 and 546, which extend from actuator 542 and are connected distally to the joint.

In some embodiments, a prime mover of an actuator such as 540 and/or 542 comprises a motor 532. In some embodiments, a speed of motor 532 ranges between, for example, 10-100 rpm, such as 20 rpm, 50 rpm, 70 rpm, 80 rpm or intermediate, higher or lower speeds. In some embodiments, motor 532 is configured to apply a torque between 0.5 N*M to 3 N*m, such as 1 N*m, 1.5 N*m, 2 N*m or intermediate, higher or lower values. In some embodiments, motor 532 is a continuous rotation motor.

Additionally or alternatively, a prime mover of an actuator comprises a linear motor. Additionally or alternatively, a prime mover of an actuator comprises a pulley. In some embodiments, the prime mover of an actuator is manually operated, for example comprising one or more cables that are pulled on to actuate movement of the gear.

In some embodiments, a single motor is configured to move more than one actuator (e.g. rotate both the bending and rotation gears). In some embodiments, dual-actuation is enabled by use of a locking mechanism and another motor configured for switching between the actuators, based on the selected articulation (e.g. bending or rotation).

In some embodiments, motor 532 is positioned parallel to the shaft extension, for example underlying the shaft extension, overlying the extension and/or positioned beside the extension. Alternatively, motor 532 is disposed within an internal lumen of the shaft extension. Alternatively, the shaft extension is configured as a part of the motor, for example contained within an external housing of motor 532.

In some embodiments, an actuator comprises a single gear or a gear train. In some embodiments, the gear train is configured to amplify the input torque generated by motor 532. Alternatively, the gear train is configured to reduce the input torque generated by motor 532. In some embodiments, the gear train is configured to reduce the rotation speed generated by the motor. In an example, the motor speed is 12,000 RPM, and the gear or gear train reduce the speed by a ratio of, for example, 134:1, 43:1, 9:1 and/or intermediate, higher or lower ratios. In an example, a gear or gear train actuating movement of an end-effecter of the arm such as grippers is configured to reduce the speed by a ratio of 9:1, enabling fast opening and closure of the gripper. This may be advantageous, for example, when dissecting tissue using the gripper.

Alternatively, in some embodiments, the gear train is configured to increase the output speed generated by the motor. In an example, the output speed of the motor is increased for autonomous electrical ablation of tissue.

In some embodiments, actuators of an actuation mechanism comprise gears or gear trains that are different from each other. In some embodiments, the motors of the two actuators are rotated at similar speeds, but the "final" movement manipulating gears of each actuator are rotated at different speeds. In an example, actuator 542 comprises a gear transmission while actuator 540 is driven directly by the motor. In another example, the actuators each comprise a single gear, but the gears are of different sizes and/or shapes (e.g. comprising different number of teeth).

In an example, actuator 540 comprises a gear that is configured to rotate shaft extension 502 directly, rotating at a speed, of, for example, 2000 RPM; actuator 542 comprises a gear that is configured to actuate bending by linearly moving elongated elements 544 and 546, optionally by rotation of a threaded screw coupled to the elements for example as described hereinbelow, and due to this additional transmission the gear of actuator 542 needs to rotated faster than gear 540, for example rotated at a speed of 4000 RPM.

In another example, an actuator that actuates an end-effecter such as a gripper is configured to rotate at a relatively fast speed, for example 9000 RPM for enabling fast movement.

Alternatively, in some embodiments, it is desired to actuate an end-effecter at a relatively low speed, for example for action requiring applying of relatively large force via the end-effector, such as separating tissue, stapling tissue, and/or other actions.

In some embodiments, actuators 540 and 542 are rotated on a single rotational axis 548. In some embodiments, axis 548 is also the rotational axis of shaft extensions 502 and 506.

In some embodiments, actuation mechanisms 520, 522, 524 of the motor unit are collinear.

In some embodiments, the motor unit includes one or more position sensor 552.

In some embodiments, position sensor 552 is placed adjacent the motor for sensing a current rotation angle of the motor.

In some embodiments, the position sensor is magnetically operated, using a magnet placed on the motor gear and sensing the magnetic flux to determine a current position of the motor gear.

In some embodiments, the motor unit is controlled by a processor 550 including a memory which stores commands.

In some embodiments, data from position sensor/s and/or from control memory is used to infer a position of device portion/s.

In some embodiments, the motor unit is controlled by a processor configured in the user's input device.

Figure 6:
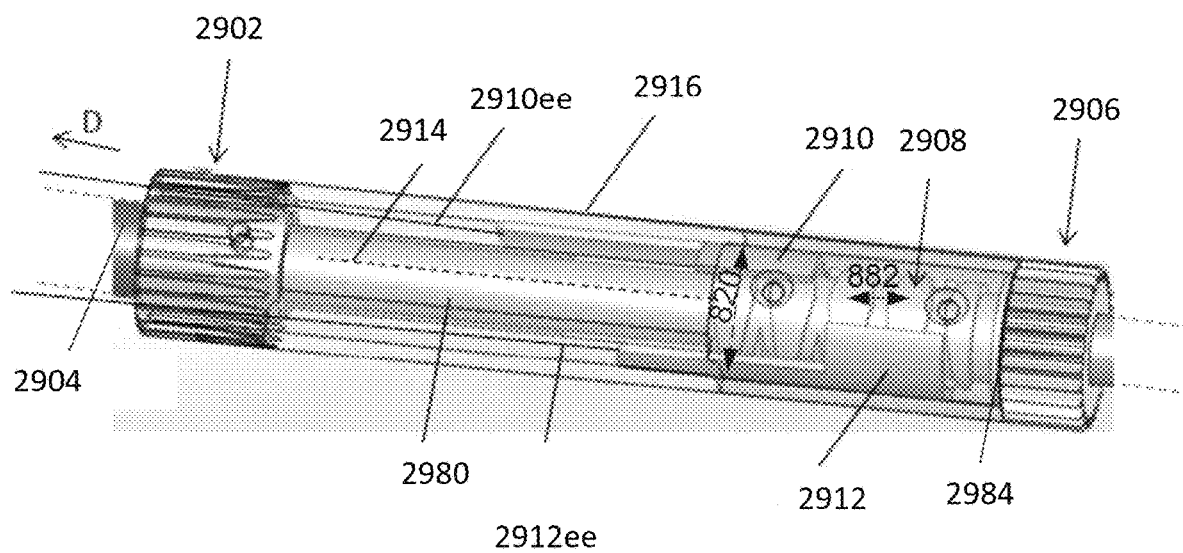
FIG. 6 is a simplified schematic side view of an actuation mechanism for control of a surgical arm joint, according to some embodiments of the invention.

FIG. 6 is a simplified schematic side view of an actuation mechanism for control of a surgical arm joint, according to some embodiments of the invention.

In some embodiments, a rotation gear 2902 is coupled to a shaft 2904, where shaft 2904 is coupled to an extension (e.g. to torso 3102, FIG. 3A). In some embodiments, rotation of rotation gear 2902 causes rotation of shaft 2904 which in turn rotates the distal extension coupled to the shaft.

In some embodiments, a shaft 2980 which is nested, at least in part, within shaft 2904 extends in the proximal direction to a bending gear 2906.

In some embodiments, bending gear 2906 is coupled to a portion including screw threading, referred to herein as threaded screw 2908. In some embodiments, a threading on screw 808 comprises a double thread. In some embodiments, rotation of the double thread in one direction achieves bidirectional lateral movement of one or more rider elements, such as half-nuts referred to elsewhere in this document, coupled to the screw.

In some embodiments, a pitch 882 of the screw thread is selected according to the use of the arm. For example, a small thread pitch is more advantageous when the arm is configured to operate large loads, for example a load of 2000 grams, 1500 grams, 3000 grams or intermediate, larger or smaller loads at a low speed (e.g. 0.5 rounds per second, 1 round per second, 0.2 rounds per second). Alternatively, a large thread pitch is more advantageous when the arm is configured to operate small loads, for example 100 grams, 50 grams, 300 grams or intermediate, larger or smaller loads at a higher speed (e.g. 2.5 rounds per second, 4 rounds per second, 5 rounds per second).

In some embodiments, rotation of the bending gear 2906 causes rotation of threaded screw 2908. In some embodiments, a first half nut 2910 and a second half nut 2912 are coupled to screw threaded screw 2908 such that rotation of the screw threading generates linear movement of half-nuts parallel to a long axis 2914 of central shaft 2904, where first half-nut 2910 and second half-nut 2912 move in different directions.

In some embodiments, each of the half-nuts is limited to movement in a single direction, for example a right handed half-nut and a left handed half-nut. In some embodiments, movement of the half-nuts is limited by one or more protrusions, for example protrusions extending radially inward from an inner wall of housing 2916, for example as further described herein.

In some embodiments, first half nut 2910 and second half nut 2912 are connected to elongated elements 2910ee and 2912ee respectively, where linear movement of the nuts pulls one elongated element whilst releasing and/or pushing on the other, generating flexion/extension of the joint. In some embodiments, a distance 820 between the half-nuts, measured along an axis perpendicular to the long axis, defines the distance between the elongated elements. In some embodiments, distance 820 between the elongated elements remains constant. In some embodiments, first nut 2910 is configured remain in line with elongated element 2910ee, and second nut 2912 is configured to remain in line with elongated element 2912ee.

In some embodiments, an elongated element such as 2910ee and/or 2912ee comprises a wire, cable, ribbon, tape and/or any other element which can be tensioned and released to provide for bending of the joint.

It is noted that in some embodiments, only one elongated element is used. In an example, the mechanism comprises one elongated element and an elastic element such as a spring. Optionally, the spring is configured to move relatively to the elongated element, for example if the elongated element is flexed, the spring is extended and vice versa. It is also noted that in some embodiments, more than two elongated elements (e.g. 3, 4, 6, 8) may be used.

In some embodiments, actuation of the rotation gear rotates the arm segment and thereby pulls on the elongated elements, moving the half-nuts. If the bending gear is held stationary (e.g. by the motor gear), the threaded screw will not rotate, generating simultaneous rotation and bending of the arm segment. If the bending gear is free to rotate, pulling on the elongated elements will in turn move the half-nuts, rotating the threaded screw. Friction at interface 2984 between a head of the threaded screw and bending gear 2906 will in turn rotate the bending gear, generating rotation of the arm segment as one piece.

In some embodiments, one or both of the elongated elements is coupled to an elastic element such as a spring. Optionally, the spring is configured to limit tensioning of the elongated element(s), yielding in response to a force (e.g. torque and/or pulling force) above a certain threshold.

Exemplary Modular System

In some embodiments, an electrosurgical system (e.g. system 100, FIG. 1A) comprises one or more modular units, where each modular unit (also herein termed "surgical modular unit") comprises a surgical arm and a motor unit configured for actuating movement of the surgical arm.

In some embodiments, a system includes a plurality of modular units where each modular unit is configured to be operated separately, when the modular units are connected and when the modular units are not connected. For example, in some embodiments, the same surgical system is used to perform single port laparoscopic surgery (e.g. where all modular units being used in the surgery are attached and surgical arms inserted through a single port) and multiple port laparoscopic surgery (e.g. where modular units, in some embodiments, are detached, the surgical arms being inserted through a plurality of ports). In an exemplary embodiment, a surgical system includes two modular units, configured for surgical operation when attached and inserted into a body through a single port and when detached and inserted through multiple ports.

In some embodiments of the invention a surgical system includes a modular surgical arm configured to be attached to a modular motor unit which is configured to actuate the surgical arm.

For example, in some embodiments, a system includes a plurality of arms and a plurality of motor units where: One or more of the arms are compatible with more than one of the plurality of motor units and/or a plurality of the arms are compatible with one or more of the motor units. In some embodiments, modularity of surgical arms and/or motor units potentially enables, for example replacement of a surgical arm is replaced, for example, moving a surgical arm from one motor unit to another motor unit. In some embodiments, a system includes a plurality of arms and a plurality of motor units where each arm is compatible with more than one motor unit (e.g. each arm is compatible with each motor unit).

In some embodiments, a kit provided to a user includes separate motor unit/s and surgical arm/s which are then assembled before use of the system. In some embodiments, surgical arm/s in the kit are provided sterile.

In some embodiments, one or more surgical arm is configured to operate using a plurality of tools (e.g. different tool types), where the tools, in some embodiments, are configured to be removably attached to a surgical arm.

In some embodiments, motor units are configured to be in parallel alignment, where, for example, a longitudinal face of a housing of one motor unit comprises a geometry suitable for engaging a longitudinal face of a housing of the second motor unit. In some embodiments, the geometry comprises one or more elements for achieving an interference fit between the housings of the motor unit, such as respective protrusions and indentations.

In some embodiments, a longitudinal face of a motor unit housing is a portion of the housing where 90-99%, or 90-99.5%, or 95-99% of a surface area of the housing varies by at most 0.1-2 mm, or 0.1-1 mm, or lower or higher or intermediate ranges or values from a plane of the longitudinal face, where the plane is a tangential plane which contacts the largest surface area of the housing face. In some embodiments, the planar tangent is 0-5°, or 0-1°, from parallel to a central long axis of the housing.

In some embodiments, a plurality (e.g. two) surgical arms are held close to each other such that a lateral distance between the arms (e.g. a lateral distance between longitudinal axes of the arms) is less than 10 mm, less than 5 mm, less than 1 mm or intermediate, longer or shorter distances. In some embodiments, each motor unit is collinear with the surgical arm actuated by the motor unit, so that when the arms are connected to the motor units they are held in a parallel position with respect to each other. In some embodiments, a motor unit is an elongate element, at least a portion of the surgical arm extending out of the motor unit is elongate. In some embodiments, a long axis of the elongate motor unit is parallel to a long axis of the elongate portion of the surgical arm extending out of the motor unit.

In some embodiments, the surgical arm extends distally from the motor unit at a lateral distance smaller than 5 mm, smaller than 3 mm, smaller than 1 mm from a longitudinal face of the motor unit which engages a respective longitudinal face of the second motor unit holding the second arm. In some embodiments, more than two arms are held close to each other such that the lateral distance between the arms is less than 10 mm, less than 5 mm, less than 1 mm or intermediate, longer or shorter distances. For example, in some embodiments, 3 or 4 or 5 or 3-10 surgical arms are held close to each other.

Figure 7A:
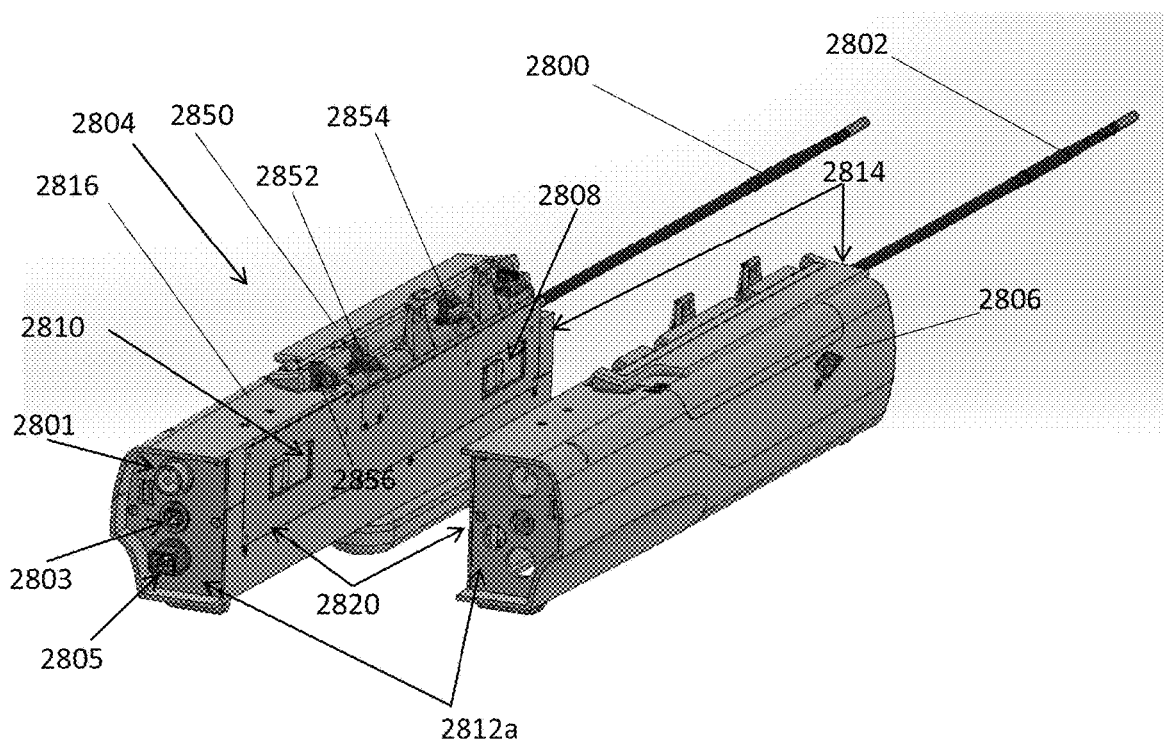
FIG. 7A illustrates an exemplary configuration of a system including two separate modular units configured to be attached to each other, according to some embodiments of the invention.

FIG. 7A illustrates an exemplary configuration of a system including two separate modular units configured to be attached to each other, according to some embodiments of the invention. In some embodiments, a first modular unit includes a first surgical arm 2800 and a first motor unit 2804 and a second modular unit includes a second surgical arm 2802 and a second motor unit 2806. In some embodiments, the units are attached using more than one attachment, for example, more than one slide attachment 2810, 2808.

Figure 7B:
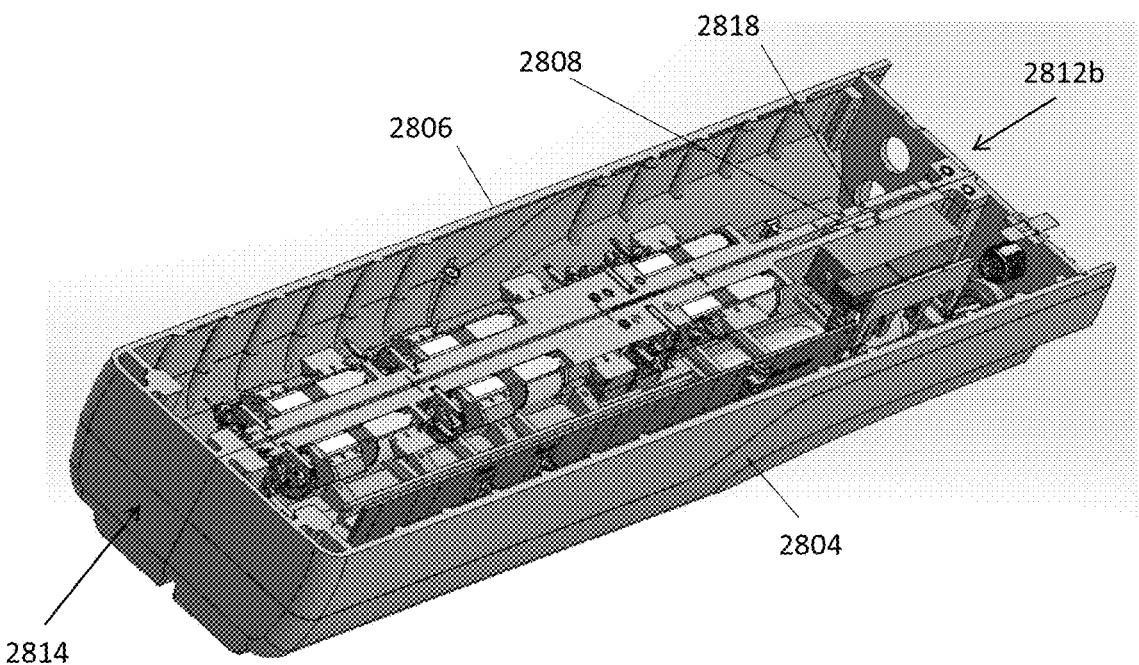
FIG. 7B is a simplified schematic cross section of a motor construct, showing attachment between motor units, according to some embodiments of the invention.

FIG. 7B is a simplified schematic cross section of a motor construct, showing attachment 2808, 2818 between motor units, according to some embodiments of the invention.

In some embodiments, a protrusion 2808 on motor unit 2804 fits into an indentation 2818 on second motor unit 2806. In some embodiments, motor units are held together and slid past each other thereby protrusion 2808 into indentation 2818.

In some embodiments, protrusion 2808 is held under a lip 2820 surrounding indentation 2818, where the lip (or lips if there are a plurality of such attachments, e.g. as illustrated in FIG. 7A) are sufficiently strong to hold the motor units together.

In some embodiments, a first end of protrusion 2808 is tapered, potentially easing alignment and/or insertion of the protrusion into the indentation.

In some embodiments, a plurality of attachments are not aligned on a motor unit longitudinal face. For example, as illustrated in FIG. 7A, attachment 2810 is closer to a top face 2816 of motor unit 2804 than a second attachment 2808. Potentially, having a plurality of attachments with different positions both parallel to a long axis and perpendicular to a long axis of the motor unit longitudinal face on which they are located increases attachment strength under loading from directions including a components perpendicular to a plane of the longitudinal face and a component parallel to a plane of the longitudinal face.

In some embodiments, surgical arms and/or motor units are modular. In some embodiments, one or more surgical arm is configured to be removably attached to a motor unit.

Referring to FIG. 7B, in some embodiments surgical arm 2800 fits into an indentation within motor unit 2804 such that gears of the surgical arm contact gears of motor unit 2804 (gears not visible in FIG. 7A).

In some embodiments, surgical arm 2800 is mechanically held in position by one or more component. In some embodiments, motor unit 2804 includes one or more clamping hammer 2852, 2854 which contact and/or apply pressure to the surgical arm. In some embodiments, clamping hammers 2852, 2854 are brought into contact and apply pressure to surgical arm 2800 when a flap 2850 is rotated about a hinge attachment to motor unit 2804 to a closed position illustrated in FIG. 7A.

In some embodiments, motor unit 2804 includes a sensor detecting whether a surgical arm has been attached. In some embodiments, motor unit 2804 includes a lock clamping hammer 2856 which, by movement of flap 2850, is brought into contact with a sensor (e.g. a microswitch). In some embodiments, this sensor provides a signal to a processor (e.g. located within a motor unit and/or located within a control console e.g. control console 118 illustrated in FIG. 1A) indicating that flap 2850 is in a closed position holding the arm onto the motor unit.

In some embodiments, the system will issue an alert to a user and/or stop use of the surgical arm/s if the sensor indicates that flap 2850 is open. In some embodiments, surgical arms are only enabled for use (movement and/or electrosurgery is enabled) upon a processor receiving a signal that the flap is closed.

In some embodiments, lock clamping hammer 2856 is configured to be held in position by a component inserted through a hole within it. In some embodiments, locking of lock clamping hammer 2856 holds the flap and/or surgical arm in position.

In some embodiments, each motor unit receives electrical power from and/or control signals at one or more connection point, for example, connection points 2801, 2803, 2805, where, in some embodiments, each connection point is configured to be connected to a cable. In an exemplary embodiment, first connection point 2801 is configured to be connected to a monopolar power supply, second connection point 2805 is configured to be connected to a bipolar power supply and third connection point 2803 is configured to receive power and/or control signals. In some embodiments, power and/or control signals received at the third connection point are delivered (e.g. by connections within the motor unit) to motors within the motor unit.

Figure 8:
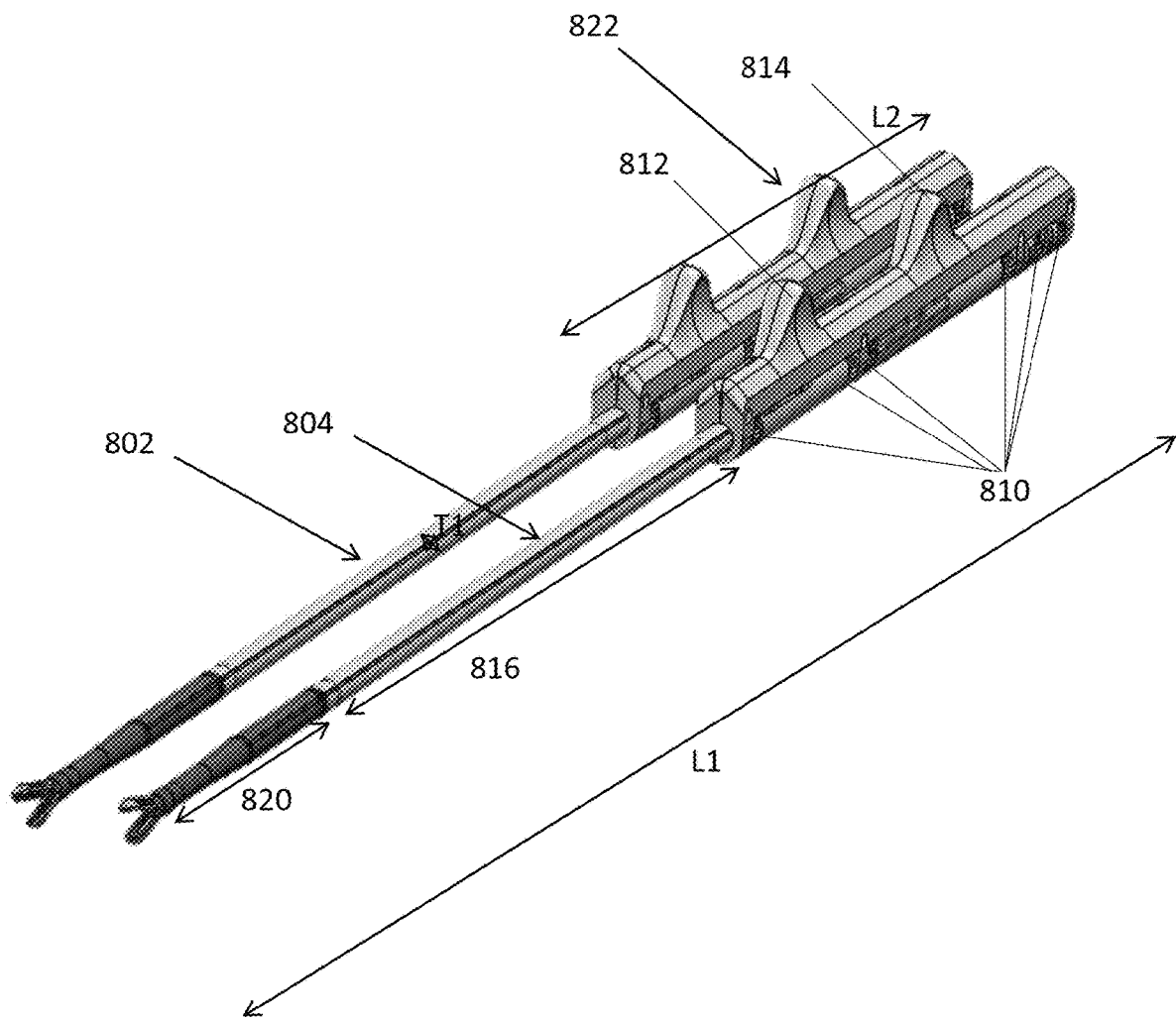
FIG. 8 is a simplified schematic of a plurality of modular surgical arms, according to some embodiments of the invention.

FIG. 8 is a simplified schematic of a plurality of modular surgical arms 802, 804, according to some embodiments of the invention. In some embodiments, a surgical arm 804 includes a gear unit 822 which includes surgical arm gears 810. In some embodiments, surgical arm gears 810, when arm 804 is connected to a motor unit, actuate the arm (e.g. as described with reference to FIG. 5 and FIG. 6). In some embodiments, arm 804 includes one or more handle, for example, two handles 812, 814 e.g. configured for grasping by a user, one in each hand. In some embodiments, handles 812, 814 and/or a side of the arm opposing exposed portions of arm gears 810 has an outer surface which is an insulating material. For example, meaning that, when arm 804 is inserted into a motor unit (e.g. as illustrated in FIGS. 7A-B) electrically live portions of the device are not at a surface of the device.

In an exemplary embodiment, a long axis length, L1, of the surgical arm is 500-1000 mm, or 650-800 mm or about 728 mm or lower or higher or intermediate ranges or lengths, a length, L2, of a surgical arm gear unit 822 is 150-350 mm, or 200-300 mm or about 260 mm or lower or higher or intermediate ranges or lengths, and a thickness, T1, of a body of surgical arms is 5-12 mm or 7-9 mm or about 8.2 mm or lower or higher or intermediate ranges or thicknesses. In an exemplary embodiment, a long axis length of a body of a surgical arm (e.g. excluding a surgical arm gear unit) is 100-700 m, or 300-600 mm, or 400-500 mm, or about 468 mm long, or lower or higher or intermediate lengths or ranges.

In some embodiments, an elastic sheath configured to cover a surgical arm, when in a relaxed state, includes about the same length and/or thicknesses, for example, so that the sheath closely fits the surgical arm. In some embodiments, the sheath is smaller in one or more dimension than the surgical arm, for example, potentially enabling a tight fit between the surgical arm and the sheath. In some embodiments, the sheath is attached to the surgical arm by pushing the arm through the sheath.

Exemplary Electrosurgical Method

Figure 9:
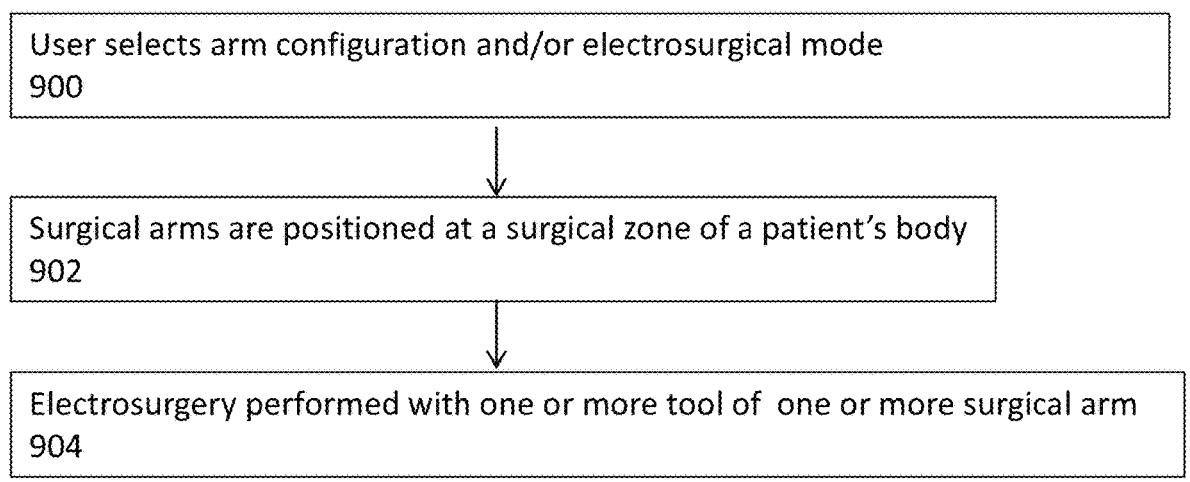
FIG. 9 is a flow chart of an electrosurgical method, according to some embodiments of the invention.

FIG. 9 is a flow chart of an electrosurgical method, according to some embodiments of the invention.

At 900 a user selects an arm configuration (e.g. including one or more of a number of surgical arms, a spatial configuration of arms) and/or an electrosurgical mode (e.g. as described regarding FIG. 10 hereinbelow).

At 902 the surgical arms are positioned at a surgical zone in a patient's body. For example, inserted into a patient's body through one or more port and/or placed in a surgical zone of a patient's body (e.g. in the case of open surgery).

At 904, the user performs electrosurgery and/or manual manipulation of tissue, using surgical arm tools and/or additional surgical tools at the surgical site. In some embodiments, one or more monopolar tip is used to cut tissue. In some embodiments, bipolar tools are used to seal and/or coagulate tissue. In some embodiments, a gripper tool (e.g. as described elsewhere in this document) is able to provide sealing for blood vessels of up to 5 mm in maximal cross sectional extent (e.g. diameter). In some embodiments, a monopolar tip, for example, when uncharged is used to perform blunt dissection and/or separation of tissue from other tissue. In some embodiments, gripper tools are used, for example, when uncharged to hold and/or pull and/or manipulate tissue.

Exemplary Electrosurgery Mode Selection

In some embodiments, each surgical arm has a plurality of operational modes, where operational modes include, for example, bipolar operation, monopolar operation and uncharged operation. In some embodiments, operational modes include sub-modes, for example, including different powers and/or frequencies for bipolar and/or monopolar operation. For example, e.g. as is known in the art of electrosurgery, in some embodiments, different power and/or frequency is used for monopolar cutting and coagulating.

In an exemplary embodiment, a surgical system includes two surgical arms, each arm connected to a motor unit. The surgical system includes eight combinations of operational mode. For example:

Combination 1=Monopolar for first arm, bipolar for second arm

Combination 2=Monopolar for second arm, bipolar for first arm

Combination 3=Monopolar for first arm, bipolar for first arm

Combination 4=Monopolar for second arm, bipolar for second arm

Combination 5=Monopolar for first arm, uncharged second arm

Combination 6=Bipolar for first arm, uncharged second arm

Combination 7=Uncharged first arm, monopolar for second arm

Combination 8=Uncharged first arm, bipolar for second arm

Additional modes include those where the first and second arms are bipolar where the first arm includes a first polarity, the second a second polarity and bipolar electrosurgery occurring when a portion of the arms (e.g. arm tools e.g. arm electrosurgical tips) are brought towards each other, e.g. into contact with each other.

Figure 10:
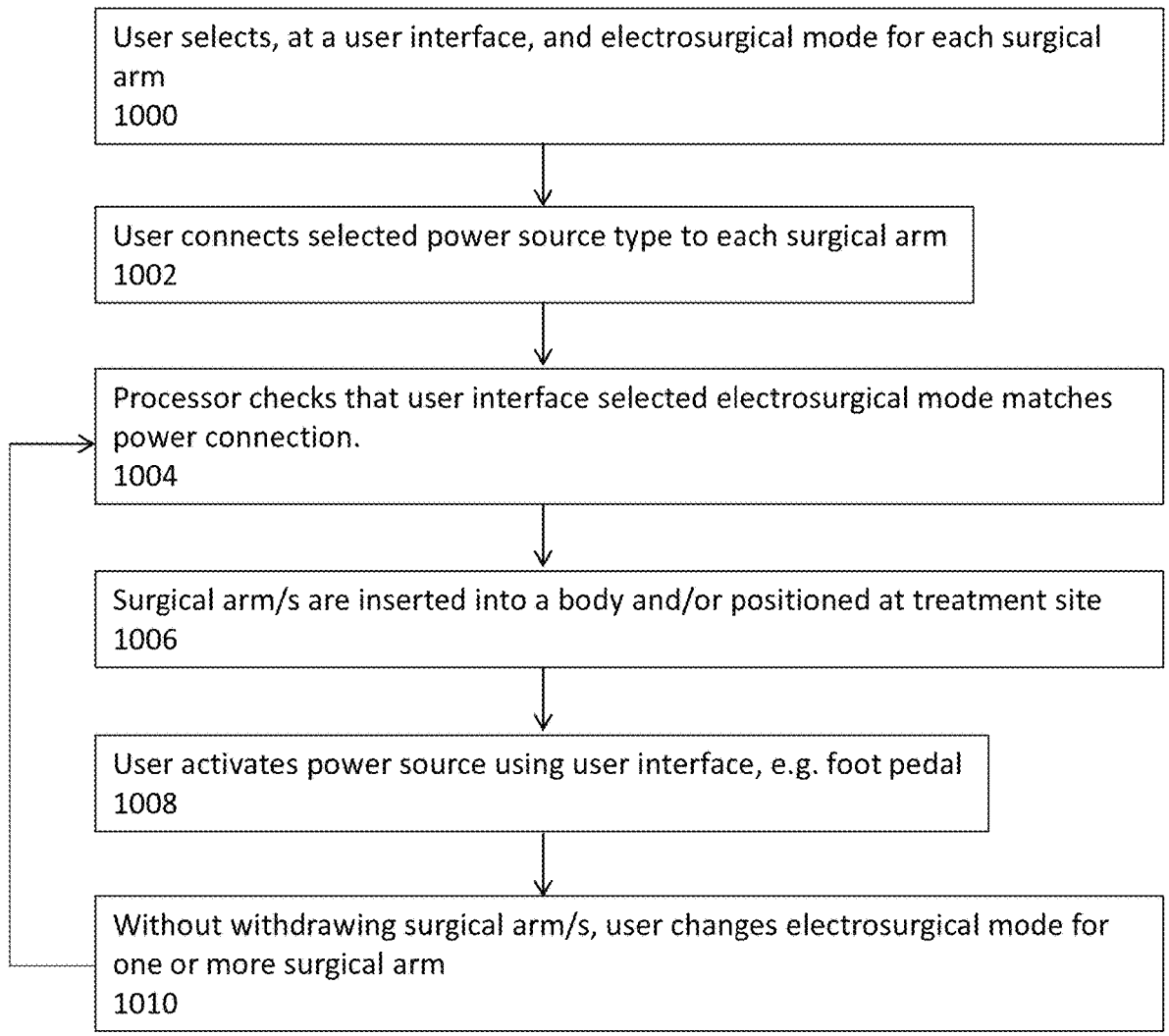
FIG. 10 is a flow chart of electrosurgical mode selection and/or switching, according to some embodiments of the invention.

FIG. 10 is a flow chart of electrosurgical mode selection and/or switching, according to some embodiments of the invention.

At 1000, in some embodiments, at a user interface (e.g. at one or more of user interfaces 128, 130, FIG. 1A) a user selects an operational mode, for example, for each arm. In an exemplary embodiment, an operational mode (e.g. for each arm) is selected using a graphical user interface (GUI) displayed on a display 128 (e.g. display 128 FIG. 1A which, in some embodiments, is a touch screen). In some embodiments, the selection is stored in a memory. In some embodiments, the selection is displayed to a user, for example, on a display (e.g. display 128).

Alternatively or additionally, in some embodiments, an operational mode, for example, for each arm and/or each motor unit, is inputted at a user interface of an electrosurgical generator (e.g. 112 FIG. 1A).

Alternatively, or additionally, in some embodiments, an operational mode, for example, for each arm and/or motor unit, in inputted at a motor unit interface e.g. where one or more motor units include a user interface.

In some embodiments, selection is mechanical, for example, pressing of a switch.

In some embodiments, the system is configured to allow selection of a different electrosurgical mode for each arm. Alternatively, in some embodiments, the system is configured to allow arms with only one type of electrosurgical power, for example enabling selection of a single type of electrosurgical power (monopolar or bipolar) and non-powered options only. For example, where a user interface does not allow disallowed selections and/or where a switch prevents two types of electrosurgical power from being supplied to the motor units.

In some embodiments, a user interface displays an indication of a selected electrosurgical mode, for example, for each motor unit. In some embodiments, a motor unit includes a user interface which displays an indication of a selected electrosurgical mode, for example a light (e.g. LED) which when lit indicates which mode has been selected. In an exemplary embodiment, each motor unit includes a light next one or more power connector (e.g. next to connector 2801 and/or next to connector 2805) which is lit once the electrosurgical mode is selected (e.g. at a user interface and/or by connecting a power cable to the connector).

At 1002, a user connects an electrosurgical generator (e.g. 112 FIG. 1A) such that the electrosurgical generator provides each arm with the selected operational mode power type. In some embodiments, connection includes electrosurgical power cables, for example, attaches an electrosurgical power cable between the electrosurgical generator and a surgical arm (e.g. arms 102, 104 FIG. 1A, e.g. arm 204 FIG. 2), for example making an connection using a cable (e.g. cables 114 FIG. 1A) for each surgical arm in the case where each surgical arm is to be electrosurgically charged. In an exemplary embodiment, for each surgical arm operating in a powered mode (e.g. monopolar or bipolar modes) an electrosurgical power cable is connected between the electrosurgical generator and a motor unit attached to the surgical arm (e.g. as illustrated by cables 114 in FIG. 1A).

In some embodiments, at an electrosurgical generator user interface and/or at a different user interface, a user selects power and/or frequency. In some embodiments, user selection during set up of the system (e.g. before insertion of the surgical arm/s) and/or during treatment with the surgical arm/s.

In some embodiments, the order of steps 1000 and 1002 is reversed, where a user first connects an electrosurgical generator to surgical arm/s and then selects operational mode/s through a user interface.

In some embodiments, connecting a desired electrosurgical supply type to a motor unit generates a signal which is then stored in a memory, the memory, for example, storing an indication of a selected electrosurgical operational mode, optionally for each motor unit and/or surgical arm. In some embodiments, a processor sends the indication for display by a user interface.

Optionally, in some embodiments, at 1004, a processor (e.g. within control console 118 FIG. 1A) checks that one or more stored electrosurgical mode selection (e.g. stored in a memory) that was made at the user interface match the power cable connection. In some embodiments, the processor checks by comparing stored memory values for user selection with received sensor signal/s, where the sensor/s providing the signal/s are located at the electrosurgical generator and/or at the motor unit/s.

In an exemplary embodiment, a user selects type of power at the user interface for each arm, information as to the type of power is sent to a processor within each motor unit. In some embodiments, each motor unit processor sends information to a relay within each motor unit which controls transfer of power from power input cables to the slip rings. In some embodiments, if there is a mismatch, the relay does not activate an energy path between the electrosurgical generator and the surgical arm/s and/or an alert is displayed to the user (for example, through a user interface e.g. a control console user interface). In some embodiments, a motor unit includes a plurality of relays, one for each electrosurgical power type. In some embodiments, a system includes one or more relay which is not located inside a motor unit for example, one or more relay (with functionality, e.g. as described above) is located within an electrosurgical power generator and/or one or more unit connected between an electrosurgical power generator and one or more motor units.

In some embodiments, at 1006, surgical arm/s are inserted into a patient (e.g. 106 FIG. 1A) and/or positioned such that the surgical arm/s reach a treatment site within a patient.

In some embodiments, at 1008, during treatment (e.g. surgery) with the surgical arms, a user activates power to one or more surgical arms. For example, in some embodiments, an arm operating in a charged mode (e.g. monopolar or bipolar) is not charged until the arm is actuated by a user interface (e.g. by pressing on a foot pedal user interface e.g. foot pedal 126 FIG. 1A). In some embodiments, a user switches between operational sub-modes during treatment, for example, switching between a coagulation bipolar mode and a sealing bipolar mode. In some embodiments, the user performs the switching at a user interface. In an exemplary embodiment, switching between sub-modes is by pressing different pedals of a foot pedal user interface (e.g. foot pedal 126 FIG. 1A).

In some embodiments, at 1000 and optionally during treatment and/or surgery (e.g. without withdrawing the surgical arms) while the arms are inserted into a patient and/or accessing a treatment zone within a patient, a user changes electrosurgical mode for one or more surgical arm e.g. performing steps 1000 and 1002 e.g. as described above.

In some embodiments, a user selects an electrosurgical operational mode at an electrosurgical supply unit (e.g. an electrosurgical generator). For example, in some embodiments, electrosurgical supply cables between a motor unit and an electrosurgical generator are not disconnected and/or reattached when changing electrosurgical operational mode. In some embodiments, an electrosurgical switching unit, placed between an electrosurgical generator and one or more a motor unit switches power supply to the motor unit, for example, without disconnecting and/or reconnecting power supply cables.

Exemplary Electrosurgery Tool

In some embodiments, an electrosurgery tool of a surgical arm (e.g. surgical arm as described elsewhere in this document, e.g. surgical arms 104, 102 FIG. 1A, 204 FIG. 2, 3104 FIGS. 3A-B) is configured to be used for both monopolar electrosurgery and bipolar operational modes (monopolar is where a single portion of the tool is charged, bipolar where two portions of the tool are oppositely charged). In some embodiments, a same portion of the electrosurgical tool is charged in both monopolar and bipolar operational modes.

Figure 11A:
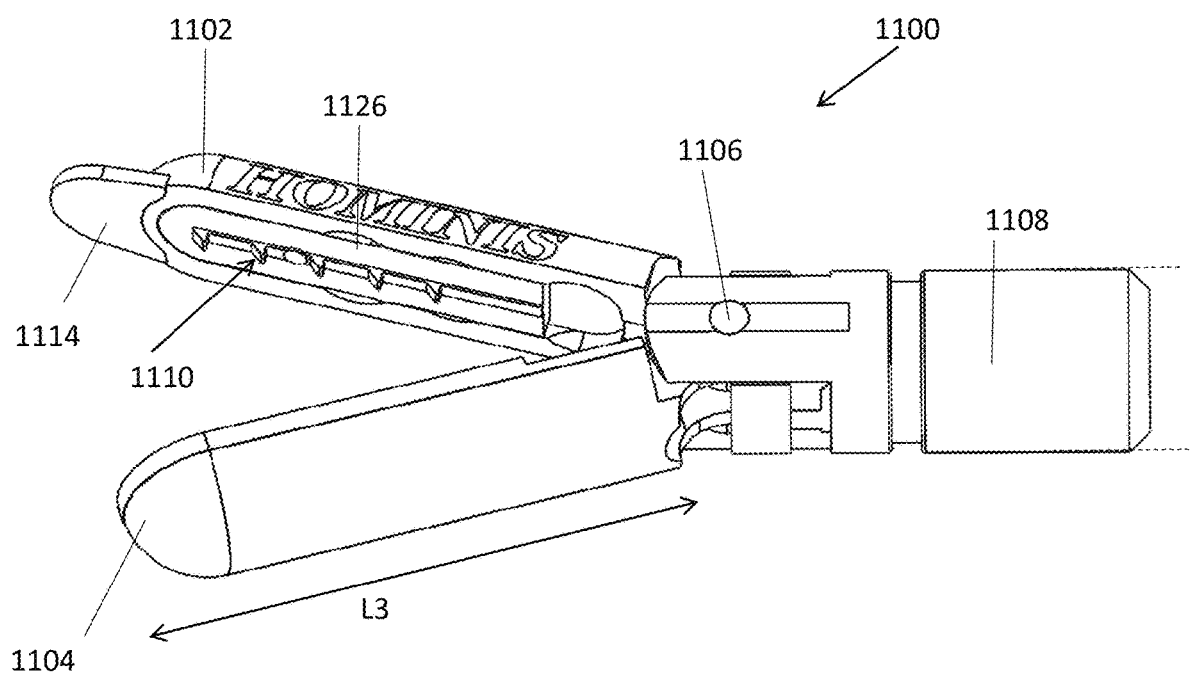
FIGS. 11A-E are simplified schematics of an electrosurgical tool, according to some embodiments of the invention.
Figure 11B:
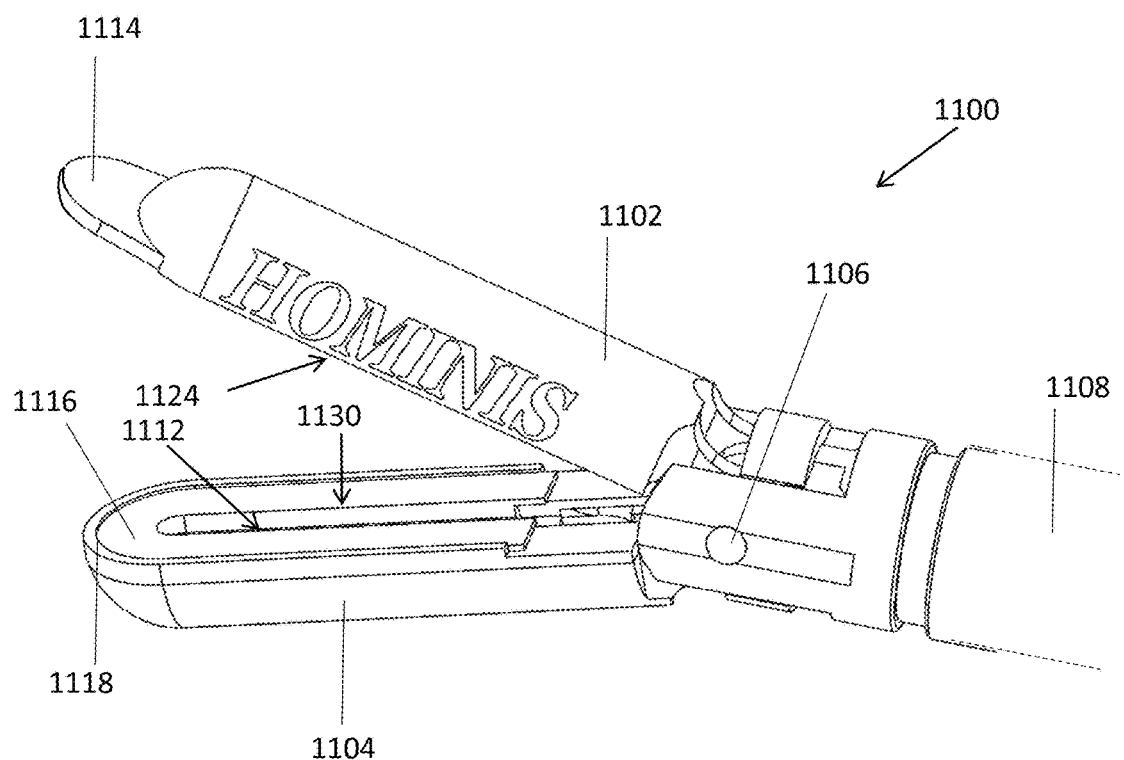
Figure 11C:
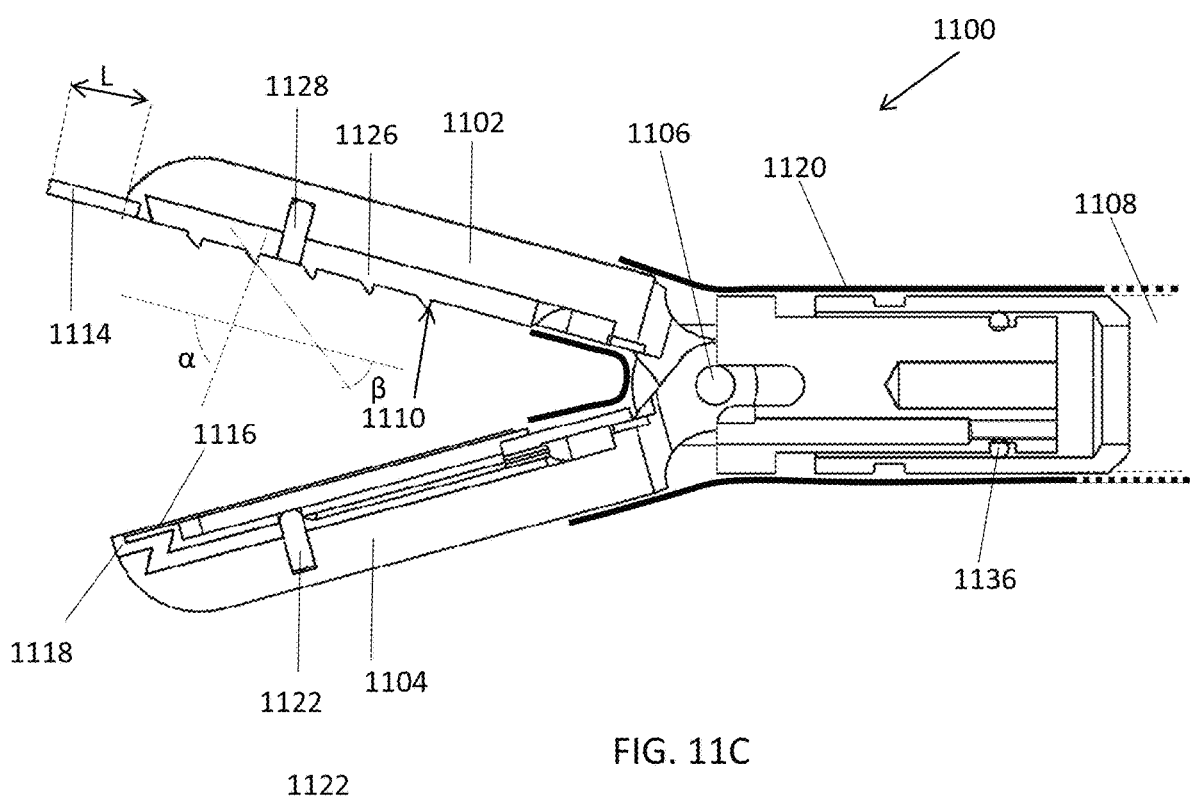
Figure 11D:
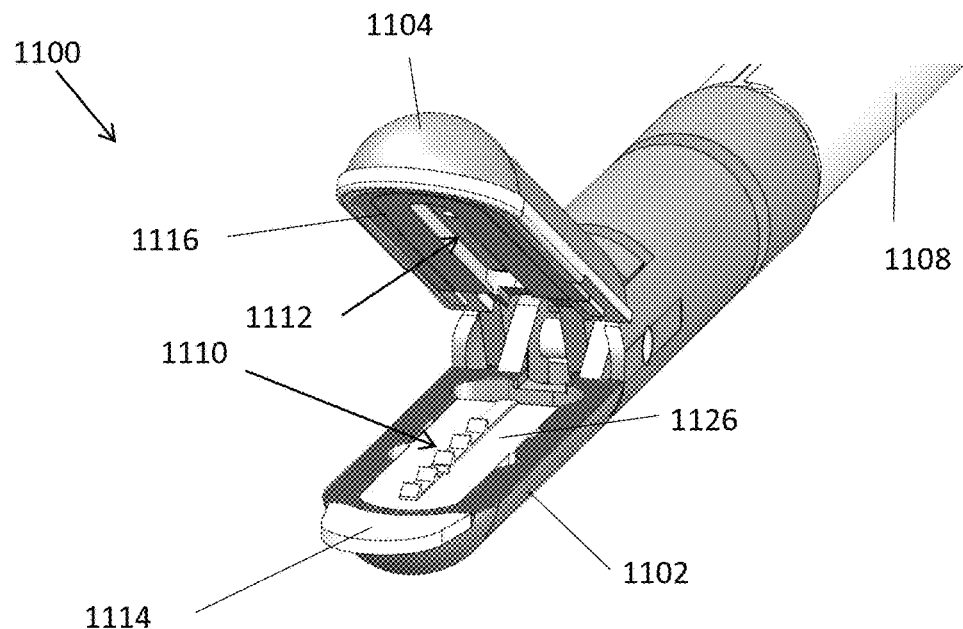

FIGS. 11A-E are simplified schematics of an electrosurgical tool 1100, according to some embodiments of the invention. FIG. 11C shows a cross sectional view of electrosurgical tool, according to some embodiments of the invention.

In some embodiments, an electrosurgical tool includes a first opposing portion 1102 and a second opposing portion 1104. In some embodiments, opposing portions 1102, 1104 are configured to be brought towards each other, for example, by rotating towards each other about a hinge 1106. In some embodiments, hinge 1106 is a pivot connection.

In some embodiments, a length, L3 of opposing side 1104 is 5-35 mm, or 15-25 mm, or 20-25 mm or about 23 mm or lower or higher or intermediate ranges or lengths.

Figure 11E:
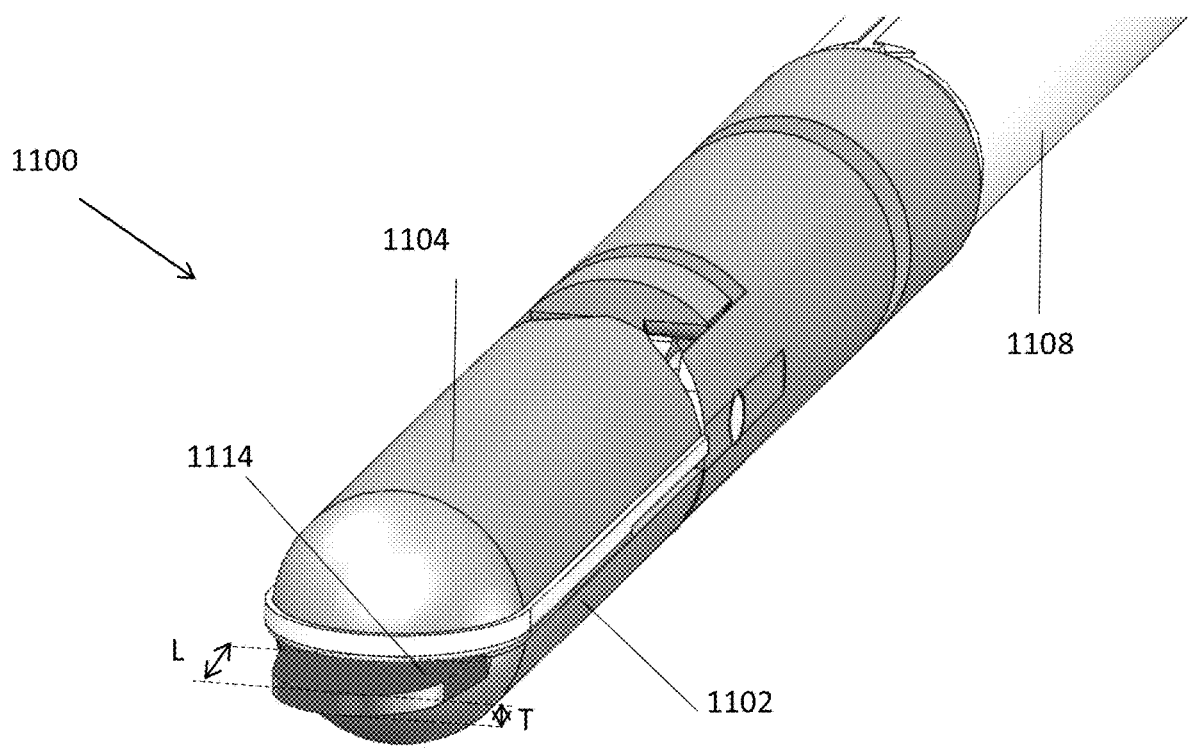

FIGS. 11A-D show electrosurgical tool 1100 in an open configuration, where faces 1124, 1130 (FIG. 11B) are apart. FIG. 11E shows electrosurgical tool 1100 in a closed configuration where opposing portions 1102, 1104 are in contact with each other and/or are at a small separation from each other (e.g. less than 2 mm or 1 mm or 0.5 mm between the faces).

In an exemplary embodiment, for example, as illustrated in FIGS. 11A-C and FIGS. 12A-C an electrosurgical tool includes two opposing portions. In some embodiments, the tool includes one or more additional opposing portion, for example, in some embodiments, a tool is a gripper or grasper including 3, or 4, or 3-7, or 3-5 opposing portions configured to approach each other.

In some embodiments, in both operational modes, a surgical arm 1108 (which comprises, in some embodiments, electrically conductive material e.g. stainless steel) of which tool 1100 forms a distal part, is charged, forming a first electrode.

In some embodiments, in monopolar operation, the second electrode is the patient's body, in some embodiments, for example, as known in the art of monopolar electrosurgery, a conducting return plate is placed in contact with the patient's body (e.g. an outer skin surface, e.g. skin of a buttock), where, in some embodiments, the return plate is connected to an electrosurgical generator providing a return electrode.

Referring now to FIG. 11C, in some embodiments, in bipolar operation, a second electrode is a conductive plate 1116 disposed on second opposing portion 1104 which is electrically isolated from the charged tool 1100 and arm 1108.

In some embodiments, conductive plate 1116 is electrically isolated by being mounted on an insulating plate 1118. In an exemplary embodiment, insulating plate 1118 includes and/or is constructed from polysulfone. In some embodiments, plates 1116, 1118 are both mounted on second opposing portion 1104 where attachment, for example, is by a screw 1122 made of (and/or coated in) insulating material.

In some embodiments, power is delivered to conductive plate 1116 vial a conducting wire which is covered in an insulating sheath. In some embodiments, the wire is held between insulating plate 1118 and conductive plate 1116, a portion of the wire (e.g. a distal end) protruding from the sheath between the plates. In some embodiments, the wire passes through an inside of surgical arm 1108, extending distally, towards the motor unit to which the arm is attached. In some embodiments the wire is a litz wire. In an exemplary embodiment, the wire is a 7 strand 34 AWG litz wire insulated with heavy polyurethane.

In some embodiments, in bipolar operation, a current path is between conductive plate 1116 and a face 1124 of first opposing portion 1102. In some embodiments, a second conductive plate 1126 is mounted on first opposing portion 1102 and, in some embodiments, is attached to first opposing portion 1102 by a screw 1128.

In some embodiments, during bipolar operation, tool 1100 is closed onto tissue to seal and/or coagulate the tissue. In some embodiments, opposing portions are configured such that a surface area of 5-50 $mm^2$, or 10-30 $mm^2$ or about 19 $mm^2$ of one opposing portions is able to be brought into close contact with the other opposing portion, for example within 1-200 μm or 20-100μ or about 50μ, or less than 100μ or less than 0.5 mm, or lower or higher or intermediate distances or ranges separation of the other opposing portion for at least 90% or 95% or 80% of a surface area of the faces of the opposing portions.

In embodiments, where a tool has more than two opposing portions, in bipolar operation, only two of the opposing portions are charged and/or one or more portion is charged with a first polarity and one or more portion is charged with a second polarity. For example, in some embodiments, a tool includes three opposing portions, where a first and a second opposing portion are charged with a first polarity and a third portion is charged with a second polarity.

Referring now to FIG. 11E, in some embodiments, in monopolar operation, the tool is used in a closed configuration illustrated in FIG. 11E, where opposing portions 1102, 1104 are in contact with each other. In some embodiments, an edge or tip of the charged (in monopolar operation) opposing portion 1102 is contacted to user tissue to cut the tissue. In some embodiments, first opposing portion 1102 includes a spatula 1114 (also herein termed "monopolar spatula") which, in some embodiments, e.g. in monopolar operation, is contacted to tissue e.g. to cut the tissue.

In some embodiments, spatula 1114 is configured to protrude from the opposing portions enough to provide a useful point for monopolar electrosurgery. In some embodiments, spatula 1114 is small enough so that it does not interfere with the ability of the tool to select and grasp (e.g. hold between the opposing portions) desired portions of tissue.

In some embodiments, when the tool is in a closed configuration, spatula 1114 length, L which is an extent of spatula protrusion from a body of first opposing portion and/or a tip of second opposing portion 1104, is 0.5-10 mm, or 1-5 mm or 2-3 mm about 2.5 mm or lower or higher or intermediate lengths or ranges.

In some embodiments, spatula 1114 is sufficiently thin and/or pointed so that a user can accurately contact a desired portion of tissue in monopolar operation, but sufficiently thick that the spatula does not mechanically cut tissue which it contacts (e.g. when the tool is used in bipolar operation and/or non-charged operation e.g. in some embodiments, the spatula is used for blunt dissection and/or separation of tissue). In some embodiments, a thickness, T (FIG. 11E) of spatula is 0.1-2 mm, or 0.10-1 mm or about 0.5 mm, or lower or higher or intermediate thicknesses or ranges.

In some embodiments, spatula has a thin, rounded shape. In some embodiments, a radius of curvature of a spatula, perpendicular to a long axis of the spatula and/or perpendicular to a long axis of the opposing portion on which the spatula is disposed is, 0.5-10 mm, or 2-8 mm, or about 2.5 mm or lower or higher or intermediate radiuses or ranges.

In some embodiments one or more of the opposing portions faces includes protrusion/s and/or indentation/s, where a topography of the face of the opposing portion deviates by at least 0.1 mm from a plane which contacts at least 80% of the face.

In an exemplary embodiment, first opposing portion 1102 includes a plurality protrusions 1110. In some embodiments, protrusions 1110 are sized and/or shaped to increase friction between opposing portion 1110 and tissue held between the opposing portions 1102, 1104. In some embodiments, protrusions 1110 protrude by 0.1-2 mm or 0.1-1 mm or lower or higher or intermediate lengths or ranges.

Referring to FIG. 11C, in some embodiments, are shaped to resist movement of tissue out from between the opposing portions in a distal direction, for example, having a sawtooth shape, for example having a shape where an angle of the protrusion to the opposing portion face at a proximal side β is smaller than the angle of the protrusion to the opposing portion face at a distal side of the protrusion α, for example. In some embodiments, protrusion/s have a pointed shape, potentially enabling penetration of the protrusions into tissue held between the opposing portions.

In some embodiments, both opposing portions faces include protrusions. In some embodiments, for example, as illustrated in FIGS. 11A-E only one opposing portion includes protrusion/s. Alternatively, in some embodiments, more than one (e.g. both opposing portions where a tool has two opposing portions) opposing portion has protrusion/s.

In some embodiments, an opposing portion face includes one or more indentation 1112. In some embodiments, an indentation on a first opposing portion (e.g. indentation 1112) is sized and/or shaped to accommodate protrusion/s (e.g. protrusions 1110) on another opposing portion configured to come into contact with the first opposing portion. In an exemplary embodiment, first opposing portion 1102 includes a plurality of protrusions 1110 and second opposing portion 1104 includes a single indentation 1112 sized and shaped to receive protrusions 1110.

Alternatively, in some embodiments, parts of opposing portions which are configured to be brought into close contact with each other are planar.

In some embodiments, tool 1100 is attached to a distal end of a surgical arm 1108.

FIGS. 12A-B are simplified schematics of a surgical arm tool 1200, according to some embodiments of the invention. FIG. 12A shows a cross sectional view of tool 1200, according to some embodiments of the invention.

In some embodiments, tool 1200 includes a first opposing side 1202 to which, in some embodiments is attached a first plate 12, where in some embodiments, first plate includes protrusions 1210. In some embodiments, tool 1200 includes a second opposing side 1204, to which, in some embodiments, is attached an insulating plate 12 and a conducting plate 12. In some embodiments, opposing portions 1202, 1204 are configured to rotate towards each other about a pivot 1206.

In some embodiments, a tool 1200 does not include a spatula. In some embodiments, both opposing portions have a pointed tip 1214a, 1214b which is contacted to tissue during monopolar cutting of the tissue. 1234. In some embodiments, during monopolar operational modes, both tips 1214a, 1214b are charged.

In some embodiments, power is delivered to conductive plate 1216 via a conducting wire 1232 which is covered in an insulating sheath. In some embodiments, the wire is held between insulating plate 1218 and conductive plate 1216, a portion of the wire (e.g. a distal end) protruding from the sheath between the plates. In an exemplary embodiment, wire 1232 is a litz wire. In some embodiments, the wire passes through an inside of surgical arm 1208, wire 1232a being an extension of (and/or electrically connected to) wire 1232. In some embodiments, wire 1232a extend distally through the surgical arm, towards the motor unit to which the arm is attached.

In some embodiments, wire 1232 is not held tightly between the tool and/or the arm, for example, allowing the wire to remain at low tension during movements of the opposing portions about the pivot and/or associated linear movement of the pivot. For example, as, in some embodiments, a length between the pivot point and a point of connection between the wire and plate 1216 changes with opening and/or closing of the tool.

In some embodiments, the surgical arm is configured so that charged portions of the surgical arm which come in contact with tissue only include the opposing portions (e.g. opposing portions 1102, 1104 FIGS. 11A-E, 1202, 1204 FIGS. 12A-B).

In some embodiments, one or more other portion of an electrosurgical mechanical arm has an insulating cover. For example, referring back to FIG. 8 in some embodiments, a support segment of a surgical arm is covered with a sheath using plastic shrink wrapping 816 (e.g. where a plastic sheath which reduces in size upon heating is fitted to the arm by placing the sheath over the arm and heating it). In an exemplary embodiments, the sheath is PET (Polyethylene terephthalate), e.g. PET shrink wrap.

Referring back to FIG. 11C, in some embodiments, portion of a surgical arm including flexible portion/s is covered by an elastic sleeve 1120 (referring to FIG. 8, arm 804 includes an elastic sleeve 820). In some embodiments, elastic sleeve 1120 leaves exposed at least a portion of the surgical arm which is configured to be electrically charged (e.g. the sleeve does not cover the entirety of opposing portions e.g. opposing portions 1102, 1104). In some embodiments, an elastic sheath extends over sheath 816, for example, providing a double insulation layer to proximal portions of the surgical arm.

In some embodiments, a dielectric strength of the elastic sheath is 1.14-118 kV/mm. In some embodiments, an elastic sleeve thickness 0.1-2 mm, or 0.1-1 mm or about 0.5 mm. In an exemplary embodiment, an elastic sleeve thickness is 0.5 mm with an engineering tolerance of ±0.05 mm. Alternatively, for example, in embodiments, where two insulated wires supply electricity to the electrosurgical tool (e.g. instead a first insulated wire and charging the arm), in some embodiments, a sleeve thickness is 5-50 μm or about 15 μm or lower or higher or intermediate ranges or thicknesses.

In some embodiments, the sleeve includes a sleeve body and a bifurcated end. In some embodiments, a length of the body is 15-10,000 mm long, or 100-2,000 mm long or 400-500 mm long or lower or higher or intermediate lengths or ranges. In some embodiments, a length of the bifurcated end is 0.1-100 mm or 1-100 mm, or 0.5-20 mm, or 1-20 mm or 1-5 mm or lower or higher or intermediate lengths or ranges.

In some embodiments, a ratio of the bifurcated end to a length of the sheath body is 1:2-1:1000, or 1:10-1:100, or lower or higher ratios or ranges.

In some embodiments, the sheath changes in cross section along the sheath, for example tapering, in some embodiments, uniformly, and/or in some embodiments, tapering in steps, for example, to match a geometry of a surgical arm with a nested structure (e.g. as described elsewhere in this document). In some embodiments, a maximal cross sectional dimension of the sleeve is 1-30 mm, or 2-20 mm, or 5-12 mm, or lower or higher or intermediate distances or ranges.

In some embodiments, sleeve 1120 is constructed from silicone rubber. In an exemplary embodiment, sleeve 1120 has 0.1-1 mm, or 0.3-0.7 mm or about 0.5 mm thickness, or lower or higher or intermediate ranges or thicknesses. In an exemplary embodiment, sleeve 1120 is 0.5 mm thick with an accuracy of ±0.05 mm. In some embodiments, sleeve 1120 allows rotation of arm 1108 within the sleeve. In some embodiments, the sleeve surrounds a portion of the surgical arm starting from distal of a first flexible portion until connection of gripper opposing portions with a body of the surgical arm. In some embodiments, the sleeve bifurcates, at a junction between the opposing portions and the body of the surgical arm, two sleeves covering the junction. A potential benefit of a bifurcated sleeve is fixation of the sleeve at the tool, potentially preventing movement of the sleeve distally, for example under friction against patient tissue when the surgical arm is moved in a distal direction. In some embodiments, bifurcation of the sleeve, in bipolar operational mode, potentially prevents electrical arching between the first and second electrodes. In some embodiments, covering of the tool at a junction between the opposing portions (e.g. the bifurcation of the sleeve) potentially prevents lodging of tissue at the inner junction between the opposing portions and/or within the hinge and/or connections.

In some embodiments, parts of the opposing portions are coated in an insulating coating. For example, in some embodiments, parts of the opposing portions not coated in insulation include the monopolar spatula or monopolar tips (e.g. spatula 1114 FIGS. 11A-E, e.g. tips 1214a, 1214b FIGS. 12A-B), and portion/s of a face of each opposing portion. In an exemplary embodiment, part/s are coated with parylen which, in some embodiments, is applied using vapor disposition to the tool where portions that are not to be coated (e.g. the monopolar spatula or tip/s) are protected with a buffer which is then removed after parylen coating.

In some embodiments, a torque cable 1290 and/or a wire 1232a rotate with the arm radius portion 1296. In some embodiments, the surgical arm includes one or more holding element 1240 which holds, for example, the torque cable 1290 and/or wire 1232a within the radius portion and/or radius extension, for example, so that all rotate together.

FIG. 12C is a top view of holding element 1240 of FIG. 12A, according to some embodiments of the invention. In some embodiments, for example, to prevent wearing of the wire and/or torque cable at points of coupling with holding elements with rotational movement, in some embodiments, holding elements are elongated elements e.g. with cross section as illustrated in FIG. 12C which extend through the arm.

Figure 13:
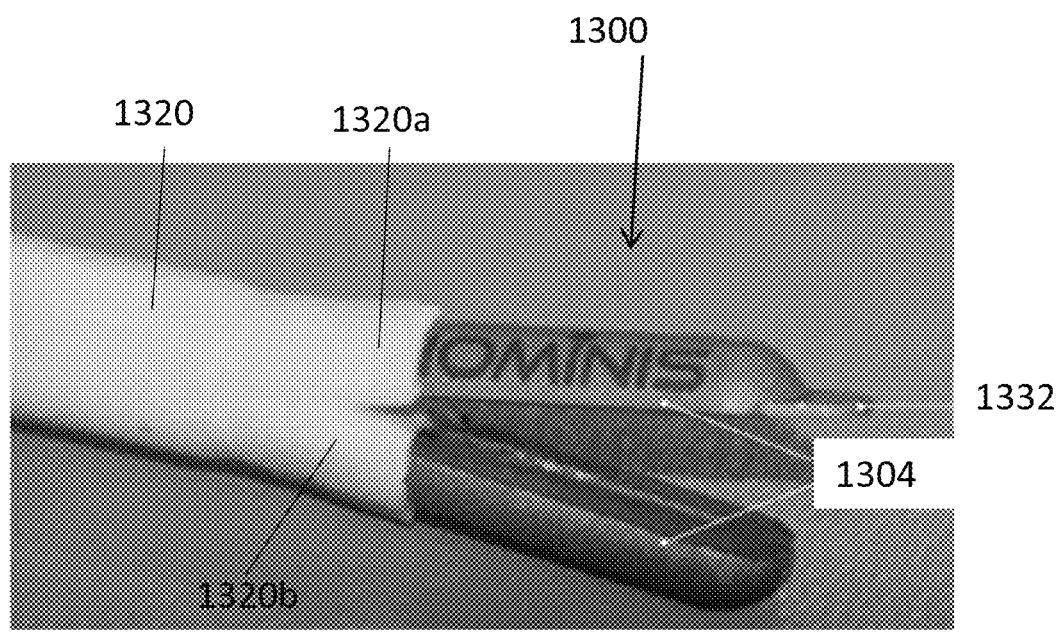
FIG. 13 is a photograph of an exemplary distal portion of a surgical arm including a tool, according to some embodiments of the invention.

FIG. 13 is a photograph of an exemplary distal portion of a surgical arm 1302 including a tool 1300, according to some embodiments of the invention. In some embodiments, a distal portion of a surgical arm including flexible portion/s is covered in an elastic sheath 1320, which is, for example, made of electrically insulating material (e.g. silicone rubber). In some embodiments, sheath 1320 extends along a distal portion of the surgical arm (and in some embodiments, the entire arm). In some embodiments, the sheath extends, covering at least a portion of a tool 1300 which is, in some embodiments, an electrosurgical tool. Including, for example, a monopolar spatula 1332 and two opposing sides 1304 (operation of which, in some embodiments, is described elsewhere in this document, e.g. spatula 1132 FIGS. 11A-E, e.g. spatula 1232 FIGS. 12A-B, e.g. opposing portions 1102, 1104 FIGS. 11A-E e.g. opposing portions 1202, 1204 FIGS. 12A-B) In some embodiments, elastic sheath 1320 bifurcates, a portion of the sheath splitting into two sheathes 1320a, 1320b, covering a base of each of two opposing portions 1304.

In embodiments including more than two opposing portions, in some embodiments, a sheath (e.g. elastic and/or electrically insulating) divides into more than two portions, e.g. into a same number of portions as opposing portions. In some embodiments, the sheath is non elastic and/or includes non-elastic portions.

Referring now to FIG. 12A, in some embodiments, an elastic sleeve 1220 mechanically protects and/or provides additional electrical isolation to wire 1232. In some embodiments, surgical arm sleeves (e.g. sleeves 816 820 FIG. 8, 1120 FIG. 11C, 1220 FIG. 12A) provide sealing and/or protection to the surgical device arm from, for example from fluid e.g. bodily fluids. Additionally or alternatively, in some embodiments, surgical arm sleeves provide a sterile cover to surgical arm.

In some embodiments, a sleeve (e.g. sleeves 816 820 FIG. 8, 1120 FIG. 11C, 1220 FIG. 12A) is constructed by coating a mold (e.g. dip coating). FIG. 14A is a simplified schematic side view of a surgical arm jig 1400, according to some embodiments of the invention. FIG. 14B is an enlarged side view of a distal end of the jig illustrated in FIG. 14B.

In some embodiments, jig 1400 includes an arm 1402 which bifurcates into a first portion 1404 and a second portion 1406, where portions 1404, 1406, in some embodiments, are attached to a terminating portion 1408. In some embodiments, jig 1400 includes a base 1412.

In some embodiments, arm 1402 is sized and/or shaped to be sufficiently long so that a coating manufactured by dipping the jig is long enough to cover a desired portion of a surgical arm (e.g. surgical arms as described elsewhere in this document). In some embodiments, first and second portions 1404, 1406 are sized and/or shaped such that a coating manufactured by dipping the portions is sized and/or shaped to cover a portion of opposing portions of a tool (e.g. opposing portions 1102, 1104 FIGS. 11A-E e.g. opposing portions 1202, 1204 FIG. 12A). In some embodiments, jig portions have smaller cross sectional (cross section taken perpendicular to their long axes) than that of surgical arms and/or opposing portions (e.g. as described elsewhere in this document). For example, so that a sheath manufactured by dipping the portions is sized to fit the surgical arm and/or opposing portion/s, for example, stretching to fit the surgical arm and/or opposing portions tightly. In some embodiments, a sleeve is put onto a surgical arm using one or more actuated tool. In some embodiments, suction is applied and/or a vacuum, for example, to enlarge the sleeve potentially easing fitting of the sleeve onto the surgical arm.

In some embodiments, jig 1400 is dipped into a liquid coating solution, then the coating covering the jig is allowed to dry. FIG. 14C is a simplified schematic of a distal portion of a jig after covering with a coating 1410, according to some embodiments of the invention.

In some embodiments, coating 1410 is further treated, e.g. heated, chemically treated, for example after dipping while the coating is on the jig and/or at a different point in the manufacture process, e.g. after the coating has been removed (e.g. in one piece) from the jig.

In some embodiments, the jig is disassembled into two or more parts, for example, to enable removal of the sheath from the jig in one piece. FIG. 14D is a simplified schematic side view of a distal portion of a jig disassembled for removal of a sheath, according to some embodiments of the invention. In some embodiments, e.g. to remove the coating sleeve from the jig, terminating portion 1408 is removed from the first and second portions 1404, 1406, for example, by unscrewing screw attachments. In some embodiments, the sleeve coating is then trimmed and/or shaped, before and/or after being placed onto a surgical arm.

In some embodiments, terminating portion 1408 has a shape which forms an extension of portions 1404, 1406, potentially providing a smooth distal end to a sleeve. For example, in some embodiments, terminating portion 1408 has a disk shape with tapering sides.

In some embodiments, first and second portion 1404, 1406 are angled to match a geometrical configuration of tool opposing portions when the opposing portions are fully open, for example, with an angle between the facing sides of the first and second portion 1404, 1406 at 30-70°, or 40-60° or about 50°, or lower or higher or intermediate ranges or angles.

Exemplary Power Supply

Figure 18:
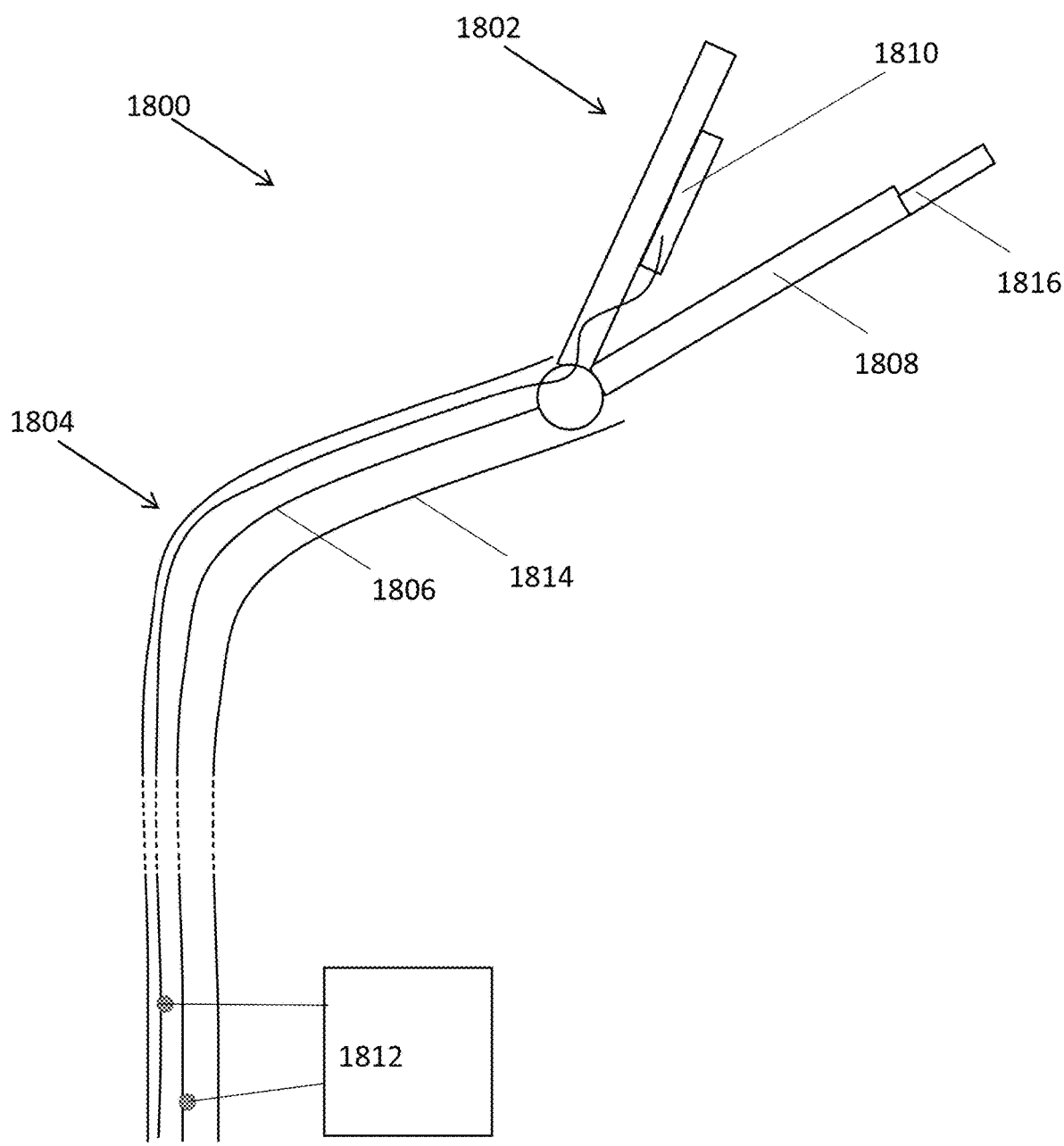
FIG. 18 is a simplified schematic cross sectional view of a portion of a surgical arm connected to an electrosurgical tool, according to some embodiments of the invention.

FIG. 18 is a simplified schematic cross sectional view of a portion of a surgical arm 1800 connected to an electrosurgical tool 1802, according to some embodiments of the invention. In some embodiments, surgical arm includes one or more flexible portion 1804.

In some embodiments, (e.g. for bipolar and monopolar operational modes) an elongated element 1806 supplies a first electrosurgical supply path, where, in some embodiments, the path extends from a power source 1812 (e.g. located at a proximal end of the surgical arm) to tool 1802. In some embodiments, the first electrical supply path extends through a space defined by the surgical arm, for example, through a lumen of a tubular portion 1814.

In some embodiments, tool includes a monopolar spatula 1816.

Additionally or alternatively, in some embodiments, electrosurgical tool 1802 is actuated by the elongated element 1806, where actuation moves a first tool portion 1808 into and out of contact with a second tool portion 1810.

In some embodiments, elongated element 1806 is not electrically isolated from the surgical arm and the first electrical supply path includes one or more additional portion of the surgical arm. For example, a tubular portion of the arm 1814, which, in some embodiments, is configured to rotate about a tubular portion long axis and, in some embodiments, is coupled to tool 1802, the rotation of the tubular portion rotating the tool about the tubular portion long axis. A potential benefit of an electrical path including a body of a surgical arm e.g. including elongated element 1806 and tubular portion 1814 is reduced impedance of the electrical path.

In some embodiments (e.g. in a bipolar operational mode) the arm includes a second electrosurgical path, in some embodiments, extending from power supply 1812, through a volume defined by the surgical arm e.g. a through a lumen of tubular portion 1814. In some embodiments, the second electrosurgical supply path is connected to a portion of the tool 1810, which is, in some embodiments, insulated from the rest of the tool.

In some embodiments, a surgical arm is includes portions which are rotatable about a portion long axis, for example, as describe regarding surgical arm 204 FIG. 2, 3104 FIG. 3A.

In some embodiments, for example, as described with reference to FIGS. 11A-E and 12A-B, an electrosurgical tool of a surgical arm is configured to be supplied with electrical power of different polarities. In some embodiments, electrical supply to the electrosurgical tool extends from the tool, through hollow portions of the surgical arm to the motor unit where, in some embodiments, the motor unit receives electrosurgical power e.g. from an electrosurgical generator.

Referring back now to FIG. 12A, in some embodiments, wire 1232a passes through an inside of surgical arm 1208, extending distally, towards the motor unit to which the arm is attached.

Figure 15A:
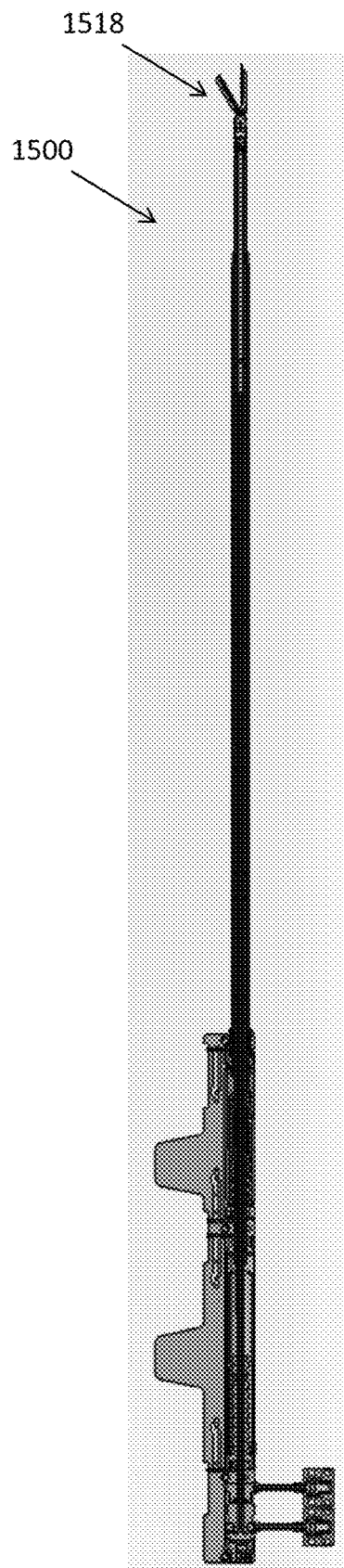
FIG. 15A is a simplified schematic cross sectional view of a surgical arm, according to some embodiments of the invention.
Figure 15B:
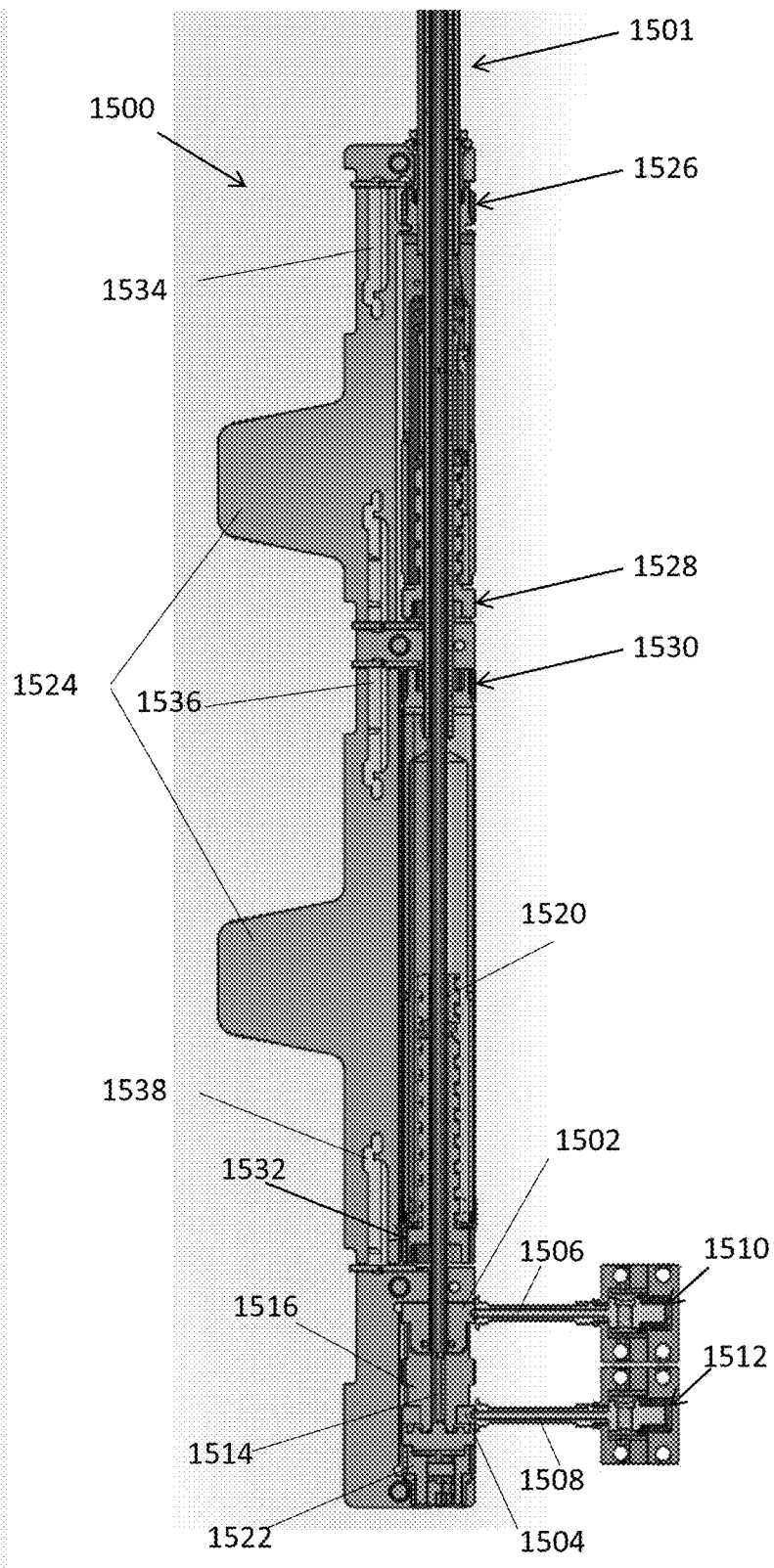
FIG. 15B is simplified schematic cross sectional view of a portion of a base of the surgical arm illustrated in FIG. 15A, according to some embodiments of the invention.

FIG. 15A is a simplified schematic cross sectional view of a surgical arm, according to some embodiments of the invention. FIG. 15B is simplified schematic cross sectional view of a portion of a base of the surgical arm illustrated in FIG. 15A, according to some embodiments of the invention.

In some embodiments, surgical arm 1500 includes a first slip ring 1502 and a second slip ring 1504 where power is supplied to the slip rings by a first brush 1506 and a second brush 1508 respectively.

In some embodiments, brushes 1506, 1508 are spring loaded (e.g. including springs 1510, 1512) which urge the brushes into contact potentially maintaining a good electrical contact between each brush and the slip ring which it contacts.

In some embodiments, first slip ring 1502 is electrically and mechanically coupled to a radius extension 1520 where first slip ring 1502 and radius extension 1520 rotate together about a radius extension long axis. In some embodiments, radius actuation gear 1520 actuates rotation of the wrist extension and first slip ring. In some embodiments, radius extension includes one or more torque transfer portion, for example, as in the description of radius extension in the description of FIG. 3A.

In some embodiments a tool extension 1514 is coupled to tool actuation gear 1522 the rotation of which rotates tool extension 1514 around a tool extension long axis. In some embodiments, tool extension is configured to transfer torque along a tool extension length, e.g. without twisting. In an exemplary embodiment, tool extension is a torque cable. In some embodiments, (e.g. as described hereinbelow with regards to FIG. 12A where tool extension is 1290) rotation of tool extension 1514 actuates a surgical arm tool 1518 which is, in some embodiments, disposed at a distal end of the surgical arm. In some embodiments, tool extension 1514 passes through a length of the surgical arm, extending from tool actuation gear 1522 to the tool e.g. as described regarding hand tool extension 3190, FIG. 3A.

In some embodiments, first slip ring 1502 is electrically connected to a hand tool extension 1514 (which e.g. has functionality as described regarding hand tool extension 3190 FIG. 3A). In some embodiments, first slip ring 1502 is mounted on radius extension 1520 rotation of the extension thereby rotating first slip ring. In some embodiments, nested structure of surgical arm 1500 (where nested structure is, for example, as described regarding FIGS. 3A-C) is, in some embodiments, where structures of the nested structure are in sufficiently close contact and/or interconnected such that a body 1501 of the surgical arm is charged by applying charge to first slip ring 1502. Alternatively, in some embodiments, radius extension 1520 and/or torque cable 1514 are electrically isolated (e.g. by a sheath and/or coating) from each other and/or from other portions of the arm (e.g. other nested tubular part/s).

Alternatively and/or additionally, in some embodiments, first slip ring is connected to an opposing portion (e.g. first opposing portion 1102 FIGS. 11A-E, 1202 FIGS. 12A-B) by a wire which is, in some embodiments, electrically isolated (e.g. by a insulating coating). In some embodiments, both first opposing portion and/or second opposing portion receive electrical power supply (e.g. electrosurgical power supply) through insulated wires.

In some embodiments, surgical arm includes one or more handle 1524 where the handle/s are, for example, as described regarding handles 812, 814 FIG. 8.

In some embodiments, surgical arm includes one or more clamping and/or locking element 1534, 1526, 1538, the operation of which, is, in some embodiments, as described regarding elements 2854, 2852, FIG. 7A.

In some embodiments, the surgical arm includes a plurality of surgical arm gears 1526, 1528, 1530, 1532, configured to actuate surgical arm 1500, the operation of which gears is, for example, as described in FIG. 5 and/or FIG. 6 and/or in International Patent Application No. IL2016/050976 which is herein incorporated by reference in its entirety.

Figure 16:
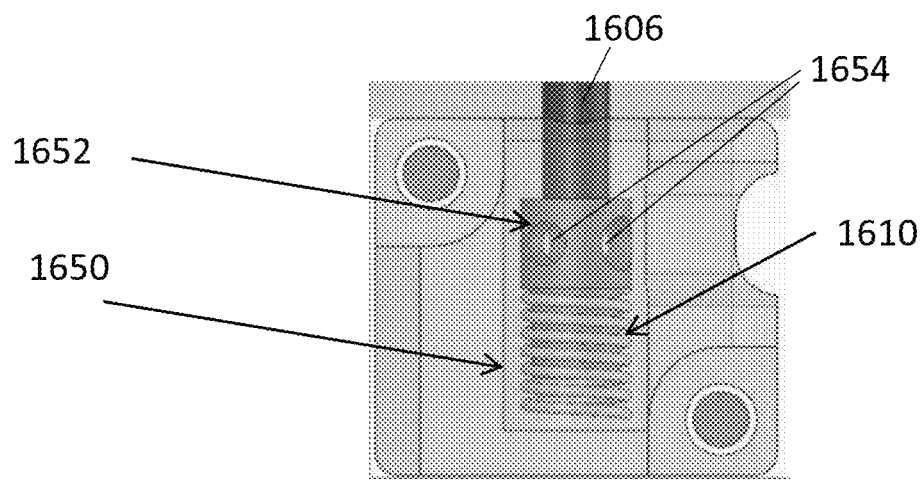
FIG. 16 is a simplified schematic of a portion of a contact, according to some embodiments of the invention.

FIG. 16 is a simplified schematic of a portion of a contact, according to some embodiments of the invention. In some embodiments, a contact includes a brush portion 1506 which, for example, contacts a slip ring (e.g. one of slip rings 1510, 1512 FIG. 15A-B). In some embodiments, brush portion 1506 is urged into contact with the slip ring by one or more spring 1610. In some embodiments, brush portion 1606 fits into a lumen 1650 sized and/or shaped and/or positioned to hold the brush portion and/or spring 1610. In some embodiments, brush portion 1606 is capped with a head portion 1652 which is sized and/or shaped to hold spring 1606 between the head portion and the brush within lumen 1650. In some embodiments, spring 1610 surrounds at least a portion of head portion 1652. In some embodiments, head portion 1652 includes one or more hollow 1654, for attachment of electrical supply wires, for example, into which electrical supply wires are disposed and/or attached.

Figure 17A:
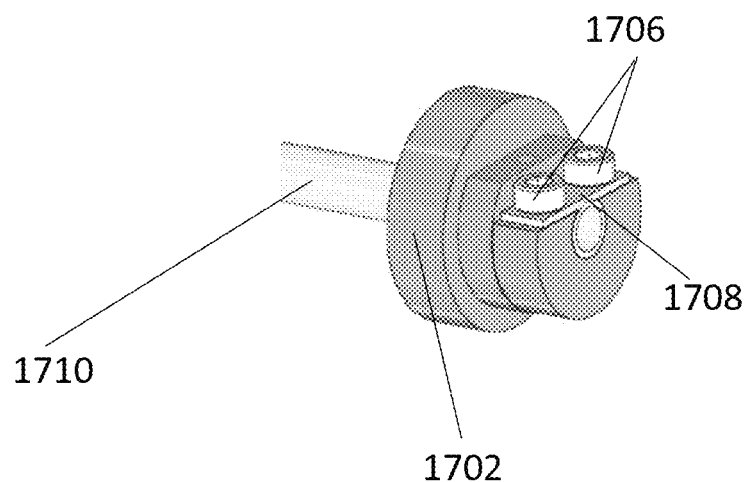
FIGS. 17A-C show simplified schematic sectional views showing connection between slip rings and other components, according to some embodiments of the invention.
Figure 17B:
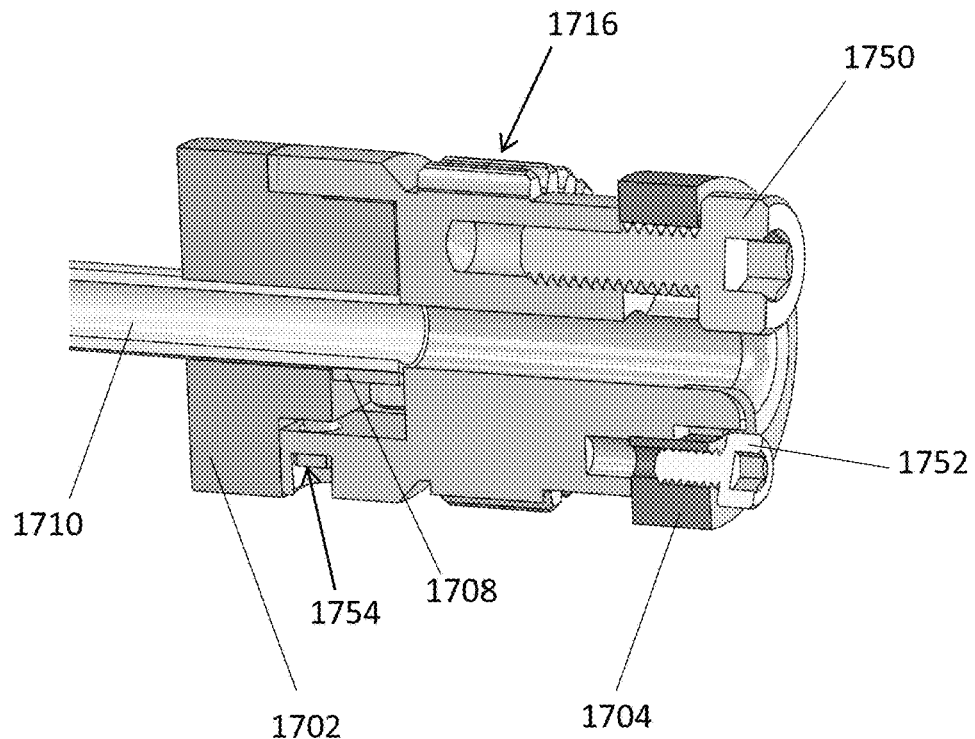
Figure 17C:
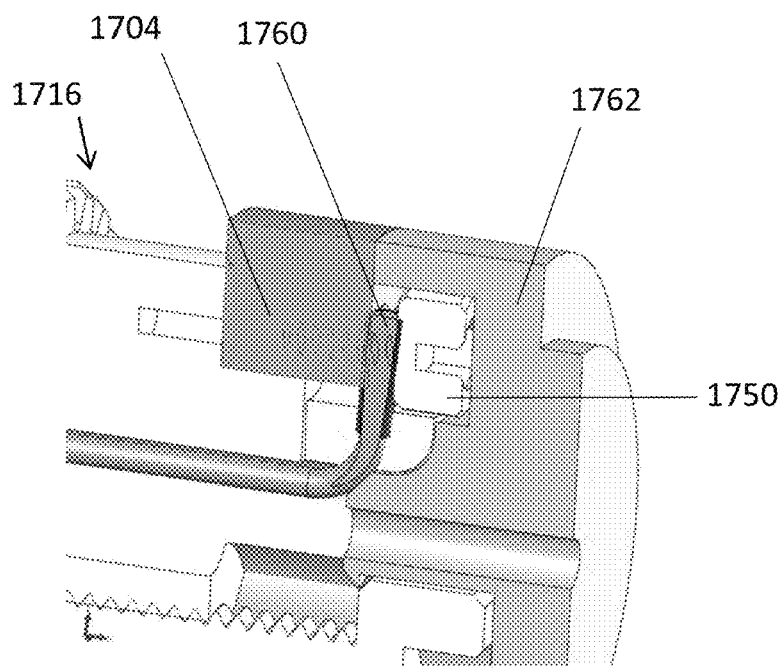

FIGS. 17A-C show simplified schematic sectional views showing connection between slip rings and other components, according to some embodiments of the invention.

FIG. 17A is a simplified schematic sectional view showing connection between a first slip ring 1702 and a wrist extension 1710 (e.g. radius extension as described regarding FIG. 3A), according to some embodiments of the invention. In some embodiments, wrist extension 1710 is connected to first slip ring 1702 at a proximal end of the wrist extension. In some embodiments, wrist extension 1710 is secured to first slip ring, for example, by a plate 1706 which clamps the wrist extension to the slip ring. In some embodiments, plate 1706 is held in position by screws 1706, which in an exemplary embodiment include or are constructed with polyether ether ketone (PEEK).

Returning now to FIGS. 15A-B, in some embodiments, second slip ring 1504 is electrically isolated from first slip ring 1502. In an exemplary embodiments, isolation is by a gear 1516 including insulating material. In an exemplary embodiment, gear 1516 includes (e.g. is constructed of) a high stiffness and strength polymer optionally not including glass reinforcement, for example, polyoxymethylene (e.g. DuPont™ Delrin® acetal homopolymer resin).

In some embodiments, second slip ring 1504 is attached to a wire which passes through the surgical arm to a surgical arm tool 1518. In some embodiments, the wire is connected to an electrosurgical contact on tool 1518. For example, the wire is an extension of (and/or is electrically connected to) wires 1232a and/or wire 1232 FIG. 12A.

FIG. 17B is a simplified schematic sectional view of a first slip ring 1702 and a second slip ring 1704 electrically isolated by a gear 1716, according to some embodiments of the invention. In some embodiments, gear 1716 electrically isolates the two slip rings e.g. is constructed from and/or is coated in an electrically insulating material (e.g. as described above regarding FIGS. 15A-B). In some embodiments, for example, as described regarding FIG. 17A, first slip ring 1702 is attached to wrist extension 1710. In some embodiments, gear 1716 is coupled to first slip ring 1702, for example, by one or more screw 1754. In some embodiments, a second slip ring 1704 is attached to gear 1716 by one or more screw 1750, 1752. In some embodiments, screw 1750 attaches second slip ring 1704 to gear 1716 and attaches a wire to second slip ring 1704 (wire not illustrated).

FIG. 17C is a simplified schematic sectional view of attachment of a wire 1760 to a second slip ring 1704, according to some embodiments of the invention. In some embodiments wire 1760 is held in electrical contact with second slip ring 1704 by a screw 1750. In some embodiments, wire 1760 is a litz wire. In an exemplary embodiment, the wire is a 7 strand 34 AWG litz wire insulated with heavy polyurethane. In some embodiments, wire 1760 extends through the surgical arm to be connected to a conducting plate (e.g. conducting plate 1216, FIGS. 12A-B e.g. conducting plate 1116 FIG. 11B). In some embodiments, an insulating cover 1762 is coupled distally to second slip ring 1704.

In some embodiments, for example, the embodiments illustrated, of FIGS. 15A-B and FIGS. 17A-C first slip ring (e.g. 1502, 1702) is powered in both monopolar and bipolar operational modes, and second slip ring (e.g. 1504, 1704) is powered only in bipolar operational modes. First slip ring is also herein termed "monopolar slip ring" and second slip ring is also herein termed "bipolar slip ring".

Exemplary Tool Actuation

In some embodiments a surgical tool is actuated where actuation, for example, includes bringing a portion of the tool towards and, in some embodiments, into contact (e.g. close contact) with another portion of the tool. In some embodiments, a tool is actuated by rotation of element/s coupled to the tool, e.g. as described hereinbelow, e.g. as described regarding FIGS. 36A-B of PCT Patent Application No. PCT/IL2015/050893.

Referring back now to FIG. 12A, in some embodiments, rotation of a torque cable 1290 actuates tool 1200 coupled to the torque cable, where actuation includes, for example, opening and closing of tool 1200 about pivot 1206. In some embodiments, rotation of torque cable 1202 rotates a screw 1292. In some embodiments, slider 1294, (which includes an inlet with threading suitable for receiving screw 1292), is prevented from rotating with screw (e.g. by one or more of housings 1226, 1238). In some embodiments, screw is prevented from linear movement e.g. by a coupling with radius extension 1296, rotation of screw 1292 thereby moving slider 1294 e.g. 7 linearly, e.g. in and/or out.

In some embodiments, linear movement of slider 1294 moves pivot 1206.

Pivot 1206 then moves with respect to holder 1236. In some embodiments, movement of portions of opposing portions 1202, 1204 against holder 1236, as pivot 1206 moves within the holder, causes the opposing portions to rotate about the pivot. In some embodiments, a portion of holder 1295 is sized and/or shaped to generate this movement.

In some embodiments, screw and/or slider are configured so that continuous rotation of the screw generates cyclical movement of the screw in and out of slider 1294 (e.g. and corresponding continuous opening and closing of the tool).

Figures 19A, 19B, 19C:
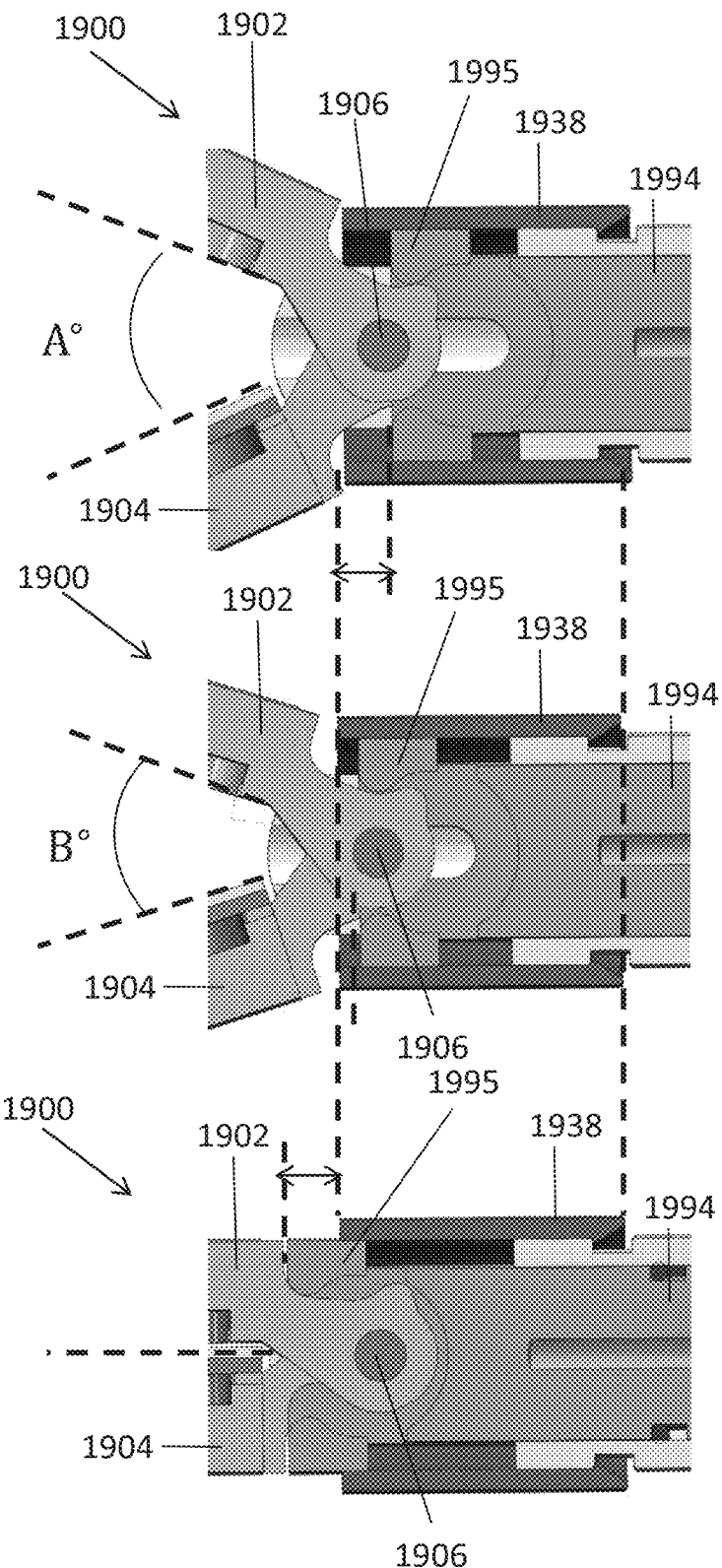
FIGS. 19A-C are simplified schematic cross sectional views of a portion of an electrosurgical tool at degrees of opening, according to some embodiments of the invention.

FIGS. 19A-C are simplified schematic cross sectional views of a portion of an electrosurgical tool 1900 at degrees of opening, according to some embodiments of the invention. In some embodiments, FIGS. 19A-C illustrate the tool of FIGS. 12A-C.

In some embodiments, pivot 1906 does not move with respect to the arm e.g. with respect to housing 1938, when tool opposing portions 1902, 1904 open and/or close.

Referring back now to FIG. 12A, in some embodiments, rotation of torque cable 1290 moves screw 1292 which thereby moves slider 1294 with respect to housing 1236.

Referring now to FIGS. 19A-C, in some embodiments, movement of a slider 1924 moves with respect to housing 1938 (which include one or more feature as described and/or illustrated regarding slider 1294 and/or housing 1238, FIGS. 12A-B).

In some embodiments, FIG. 19A illustrates tool 1900 where a first opposing portion 1902 and a second opposing portion 1904 are separated to a maximal extent, angle A° which is about 90°, or about 70°, or, in an exemplary embodiment, about 50°, or 20-130°, or 30-70°, or 40-60°, or lower or higher or intermediate ranges or angles.

In some embodiments, when tool 1900 is opened to a maximal extent, slider 1994 is retracted into housing 1938 to a maximal extent. In some embodiments, as slider 1994 is extended outwards from housing 1994 and/or with respect to fixed pivot 1906, movement of the opposing portions 1902, 1904 against holder 1995 generates a moment which rotates the opposing portions 1902, 1904 about pivot joint 1906, closing the opposing portions. Conversely, in some embodiments, as the slider is retracted into housing 1938 and/or with respect to holder 1995, movement of the opposing portions 1902, 1904 against holder 1995 generates a moment which rotates the opposing portions 1902, 1904 about pivot joint 1906, opening the opposing portions.

In some embodiments, slider 1994 e.g. as described with respect to FIGS. 19A-C is configured to be moved with respect to holder 1995. Alternatively or additionally, in some embodiments, holder 1995 is configured to be moved (e.g. linearly) with respect to slider. In some embodiments, both the holder and slider are configured to be moved. Relative motion between the slider and holder, in some embodiments, actuating (e.g. opening and/or closing) the tool.

In some embodiments, both opposing portions move, for example, both opposing portions shaped and/or the slider shaped to generate a moment about pivot 1906 for both opposing portions when there is relative motion between the slider and the holder. For example, in some embodiments, opposing portion 1904 has the same shape which contacts holder 1995 as opposing portion 1902. Alternatively, in some embodiments, only one of the opposing portions 1902, 1904 is rotated about pivot 1906.

In some embodiments, (e.g. including one or more feature as described and/or illustrated with respect to tool 1200 FIGS. 12A-C) a tool (e.g. tool 1900) is actuated by rotation of a portion (e.g. an elongated element which in an exemplary embodiment is a torque cable). Alternatively or additionally, in some embodiments, the tool is actuated by a different mechanism. For example, by changing tension on one or more elongated element (e.g. cable). For example, in some embodiments, relative movement between slider 1994 and holder 19995 is controlled by changing tension on one or more cable.

In some embodiments, the portions of the opposing portions which move against portion of a holder (e.g. holder 1295 FIGS. 12A-B, e.g. holder 1995 FIGS. 19A-C) (e.g. opposing portion cams) are sized and/or shaped so that more movement of the slider with respect to the holder (e.g. more rotations of the torque cable are needed) to effect closing of the tool than opening of the tool. A potential benefit being quick release of the gripper tool and/or slow closing for increased control of electrosurgery using the tool. A further potential benefit being that slower closing increases a load on the actuator and/or tool (e.g. of tissue on the tool) gradually potentially reducing forces and/or wear on the actuator and/or tool part/s. In an exemplary embodiment, closing time of the tool (e.g. the tool and/or motors and/or torque cable are configured so that the closing time) is about 0.5 seconds, or is at least 0.5 seconds, or is 0.1-1 seconds or lower or higher or intermediate times or ranges.

In some embodiments, a gradient of a surface of a first portion 1901 of opposing portion 1902 which contacts holder 1995 is lower than a gradient of a surface of a second proximal portion 1903 of opposing portion 1902. In some embodiments, the higher gradient portion results in an increased pivoting moment for a given amount of linear movement of holder 1995 with respect to the slider (e.g. slider 1994 FIGS. 17A-C). In some embodiments, the higher gradient surface is proximal to the lower gradient surface. In some embodiments, the higher gradient surface is traversed by holder 1995 during opening of the tool and the lower gradient surface is traversed by holder 1995 during closing of the tool, which, in some embodiments, means that the tool opens for a reduced actuation input (e.g. number of revolutions of torque cable 1290 FIG. 12A e.g. reduced tension on a cable actuator) than that required to close the tool.

Figure 19D:
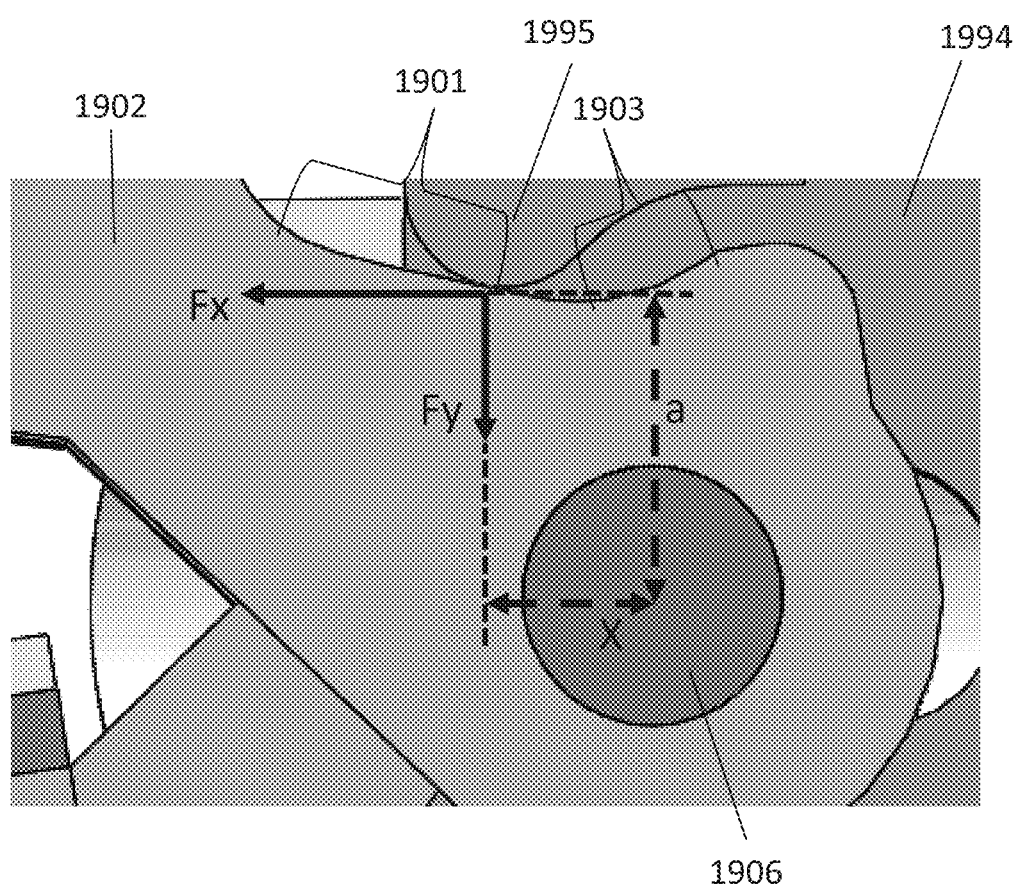
FIG. 19D is a simplified schematic cross section of a portion of a tool at a tool pivot, according to some embodiments of the invention.

In some embodiments, the surface 1901, 1903 which contact holder 1995 have a smooth change in gradient, e.g. as illustrated in FIG. 19D. Alternatively, in some embodiments, there is an abrupt change in gradient, for example, the two portions having a straight cross section perpendicular to an axis of pivot 1906. In some embodiments, the cross section of surfaces 1901, 1903 are sections of a circle (or cylinder, in some embodiments, for the whole surface) with different dimension radii. In some embodiments, the higher gradient section has at least 1.1 or 2, or 5 times the gradient of the lower gradient section.

FIG. 19D is a simplified schematic cross section of a portion of a tool 1900 at a tool pivot 1906, according to some embodiments of the invention.

In some embodiments, the turning moment generated by moving slider 1994 with respect to holder 1995 is equal to the sum of x, a moments:

$$\Sigma M = F_x * a + F_y * x$$

Where, in some embodiments, a sizes of forces Fx and Fy are due to the shape of holder 1995 and opposing portion 1902 and the coefficient of friction between the holder 1995 and opposing portion 1902. In some embodiments, the coefficient of friction between the holder and the opposing portion is low (e.g. materials of the opposing portion/s and/or holder are selected to move against each other with low friction). A potential benefit of low friction between the moving portions (opposing portion/s and the holder being reduction of sticking and/or smooth movement of the parts, for example, in some embodiments, increasing accuracy of control of actuation of the tool. For example, in some embodiments, if sticking is prevented, the number of rotations of the torque cable for a degree of opening and/or closing is known to a better accuracy. In some embodiments, the opposing portions and holder are constructed from stainless steel (a potential benefit being biocompatibility and/or ability to sterilize). In some embodiments, one or more surface of the holder and/or of one or more of the opposing portions is coated in a low friction coating. For example where surface/s of the holder and opposing portion/s which contact each other in actuation of the tool.

In some embodiments, closing pressure of the tool (e.g. one or more of tool 1100 FIGS. 11A-E, 1200 FIGS. 12A-B, 1900 FIGS. 19A-C is 50-150 PSI or 80-120 PSI or lower or higher or intermediate pressures or ranges. In some embodiments, a gripper is configured to be in configurations ranging from where the opposing portions are in close contact to where the opposing portions are at an angle of up to about 90°, or 70°, or, in an exemplary embodiment, about 50° or 20-130°, or 30-70°, or 40-60°, or lower or higher or intermediate ranges or angles.

General

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A surgical system comprising:

a plurality of modular units, each unit comprising:

a motor unit;

a surgical mechanical arm actuated by, connected to and supplied with electrosurgical power by said motor unit; and a memory storing electrosurgical operational modes including a monopolar operational mode and a bipolar operational mode, said memory configured to store a selected electrosurgical operational mode for each of said plurality of modular units; and switching circuitry which switches electrosurgical power supply from an electrosurgical generator to selectively deliver via said motor unit and to said surgical mechanical arm bipolar energy, monopolar energy, or no energy supply in accordance with said selected operational mode; wherein said switching circuitry comprises a first slip ring which is powered in both monopolar and bipolar modes, and a second slip ring which is powered only in bipolar operational mode;

wherein said first slip ring and said second slip ring are coupled to each other and are electrically isolated from each other by a gear configured to rotate said slip rings; wherein rotation of said gear drives rotation of a distal segment of said surgical mechanical arm to which said gear is attached by an extension passing inside a tubular body of said surgical mechanical arm.

2. The surgical system according to claim 1, wherein possible operational modes include said monopolar operational mode, said bipolar operational mode and an uncharged mode.

3. The surgical system of claim 1, wherein said motor unit comprises circuitry configured to:
recognize said selected electrosurgical operational mode;
send, to a processor, an indication of said selected operational mode, where said processor is configured to store said indication in said memory.

4. The surgical system of claim 1, comprising a user interface configured to:
receive said selected electrosurgical operational mode from a user, for one or more of said modular units;
send an indication of said selected electrosurgical operational mode to a processor, where said processor is configured to store said indication in said memory.

5. The surgical system of claim 1, comprising one or more displays configured to display an indication of said selected electrosurgical operational mode for one or more of said modular units.

6. The surgical system of claim 4, wherein said user interface is a touch screen display.

7. The surgical system of claim 6, wherein said touch screen display is configured to display an indication of said selected electrosurgical operational mode for one or more of said modular units.

8. The surgical system of claim 5, wherein said one or more displays comprises one or more lights on each of said motor units.

9. The surgical system of claim 1, comprising a processor connected to said memory, wherein one or more of said motor units comprises circuitry is configured to:
receive electrosurgical power supply;
receive a user selection of said electrosurgical mode from said processor;
check that said user selection matches said received electrosurgical power supply; and
enable said electrosurgical power supply to said surgical arm if said user selection matches said electrosurgical power supply.

10. The surgical system according to claim 9, wherein said circuitry is configured to disable said electrosurgical power supply to said surgical arm if said user selection does not match said electrosurgical power supply.

11. The surgical system of claim 9, wherein said circuitry is configured to generate a warning if said user selection does not match said electrosurgical power supply.

12. The surgical system according to claim 1, wherein said surgical mechanical arm includes a tool configured to operate in said operational modes.

13. The surgical system of claim 12, wherein said tool comprises:
a monopolar tip;
a first portion comprising a first bipolar surface;
a second portion comprising a second bipolar surface configured to be in brought into contact with said first bipolar surface.

14. The surgical system of claim 13, wherein said monopolar tip is attached to said first portion, where monopolar tip and said first bipolar surface are electrically connected;
wherein said second bipolar surface is electrically isolated from said first bipolar surface and said second portion.

15. A method of use of an electrosurgical system:
providing a plurality of modular units, each unit comprising a motor unit and a surgical mechanical arm actuated by, connected to and supplied with electrosurgical power by said motor unit;
selecting a desired electrosurgical operational mode for at least one of said modular units by one or more of:
connecting an electrosurgical supply to said at least one modular unit;
inputting a desired electrosurgical operational mode for said at least one modular unit at a user interface; and
providing to said surgical arm, via switching circuitry which switches electrosurgical power supply, either bipolar energy, monopolar energy, or no energy supply in accordance with said selected operational mode;
wherein said switching circuitry comprises a first slip ring which is powered in both monopolar and bipolar modes, and a second slip ring which is powered only in bipolar operational mode;
wherein said first slip ring and said second slip ring are coupled to each other and are electrically isolated from each other by a gear configured to rotate said slip rings;
wherein rotation of said gear drives rotation of a distal segment of said surgical mechanical arm to which said gear is attached by an extension passing inside a tubular body of said surgical mechanical arm.

16. The method of claim 15, comprising: detecting an electrosurgical supply type of said electrosurgical supply connected to said at least one modular unit;
comparing, using a processor, said electrosurgical supply type with said desired electrosurgical operational mode; and
enabling electrosurgical power supply to said surgical arm of said at least one modular unit if said electrosurgical supply type matches said desired electrosurgical operational mode.

17. The method according to claim 16, wherein said selecting is performed for at least two modular units;
wherein said detecting, said comparing and said enabling is performed for each said modular unit.

18. The method according to claim 17, wherein said enabling including enabling electrosurgical power supply to said surgical arms of said at least two modular units if said electrosurgical supply type matches said desired electrosurgical operational mode for each of said at least two modular units.

19. The method according to claim 16, comprising displaying an alert if said electrosurgical supply type does not match said desired electrosurgical operational mode.

20. The method according to claim 16, comprising disabling said electrosurgical power supply to said surgical arm if said electrosurgical supply type does not match said desired electrosurgical operational mode.

21. The method according to claim 15, comprising coupling at least two of said modular units by connecting motor units of said at least two of said modular units.

22. The method according to claim 15, comprising displaying one or more of:
a desired electrosurgical operational mode at a user interface, a connected electrosurgical supply type at said user interface; a connected electrosurgical supply type at a modular unit user interface;
displaying a desired electrosurgical operational mode at said user interface.

23. The method according to claim 18, comprising:
comparing one or more of:
said desired electrosurgical operational modes for said at least two modular units;
said electrosurgical supply type for said at least two modular units;
enabling said electrosurgical supply type for said at least two modular units if one or more of:
said desired electrosurgical operational modes for said at least two modular units match; and said electrosurgical supply type for said at least two modular units match.

24. The system according to claim 1, wherein said motor unit includes at least two connection points, one connection configured to be connected to monopolar power supply and the other connection point configured to be connected to bipolar power supply.

25. The system according to claim 4, wherein said switching circuitry switches said electrosurgical power supply upon receiving a signal indicative of said selected electrosurgical operational mode from said user interface.

26. The system according to claim 1, wherein said first slip ring and said second slip ring are a part of said surgical mechanical arm.

27. The system according to claim 1, wherein said slip rings and said gear have a coaxial axes of rotation.

28. The system according to claim 1, wherein said first slip ring and said second slip ring transfer electrical current via first and second electrical conduction pathways extending from said motor unit to a distal surgical arm tool respectively.

29. The system according to claim 28, wherein said first electrical conduction pathway comprises a tubular body of said surgical arm, and said second electrical conduction pathway comprises wiring which passes inside a volume of said surgical arm.

30. The system according to claim 1, wherein rotation of said gear drives rotation of a joint portion acting as a wrist of said surgical arm.

31. The system according to claim 29, wherein in bipolar mode, said wiring and said tubular body of said surgical mechanical arm each conducts a different polarity.

32. The system according to claim 26, wherein said first slip ring and said second slip ring are located at a proximal portion of said surgical mechanical arm, said proximal portion configured to be received inside said motor unit.

33. The system according to claim 32, wherein said motor unit comprises a first brush and a second brush which supply power to said first and second slip rings respectively.

34. The system according to claim 32, wherein said surgical mechanical arm comprises a plurality of flexible segments and said first and second slip rings are positioned proximally to said plurality of flexible segments.

35. The surgical system of claim 2, wherein in said bipolar energy mode and in said monopolar energy mode a tubular body of said surgical mechanical arm is electrically charged for delivering electrical current to a distal end tool.

36. The surgical system of claim 1, wherein said distal segment is coupled to a distal end tool, rotation of said gear thereby rotating said distal end tool about the distal segment long axis.

* * * * *